United States Patent [19]
Wilde et al.

[11] Patent Number: 5,310,748
[45] Date of Patent: May 10, 1994

[54] IMIDAZOLES FOR THE TREATMENT OF ATHEROSCLEROSIS

[75] Inventors: Richard G. Wilde, New Castle; C. Anne Higley, Newark, both of Del.; Jeffrey T. Billheimer, West Chester, Pa.; Ruth R. Wexler, Wilmington, Del.

[73] Assignee: The Du Pont Merck Pharmaceutical Company, Wilmington, Del.

[21] Appl. No.: 881,034

[22] Filed: May 11, 1992

[51] Int. Cl.$^5$ ................. C07D 403/12; A61K 31/415
[52] U.S. Cl. .................................... 514/397; 548/313.7
[58] Field of Search ........................ 548/337, 313.7; 514/397

[56] References Cited

U.S. PATENT DOCUMENTS

| | | | |
|---|---|---|---|
| 4,228,291 | 10/1980 | Durant et al. | 548/138 |
| 4,413,130 | 10/1983 | White | 548/340.1 |
| 4,460,598 | 7/1984 | Lautenschlager et al. | 424/273 |
| 4,623,662 | 11/1986 | DeVries | 514/596 |
| 4,654,358 | 3/1976 | Lautenschlager et al. | 514/398 |
| 4,722,927 | 2/1988 | Holmes | 514/256 |
| 4,824,843 | 4/1989 | Hoefle et al. | 514/364 X |
| 4,868,210 | 9/1989 | Trivedi | 514/539 |
| 4,882,357 | 11/1989 | Creger et al. | 514/622 |
| 4,900,744 | 2/1990 | Billheimer et al. | 514/398 |

FOREIGN PATENT DOCUMENTS

| | | |
|---|---|---|
| 335374 | 3/1988 | European Pat. Off. . |
| 0274867 | 7/1988 | European Pat. Off. ........ C07D 2/60 |
| 370740 | 11/1988 | European Pat. Off. . |
| 386487 | 2/1989 | European Pat. Off. . |
| 325397 | 7/1989 | European Pat. Off. . |
| 372445 | 12/1989 | European Pat. Off. . |
| 354994 | 2/1990 | European Pat. Off. . |
| 3504679 | 8/1986 | Fed. Rep. of Germany . |
| 3504680 | 8/1986 | Fed. Rep. of Germany . |
| 9109021 | 6/1991 | PCT Int'l Appl. . |
| 9109030 | 6/1991 | PCT Int'l Appl. . |
| 9110662 | 7/1991 | PCT Int'l Appl. . |
| 9113876 | 9/1991 | PCT Int'l Appl. . |
| 9118885 | 12/1991 | PCT Int'l Appl. ............ C07D 2/22 |
| 2038825 | 7/1980 | United Kingdom .......... C07D 4/12 |

*Primary Examiner*—David B. Springer
*Attorney, Agent, or Firm*—Blair Q. Ferguson

[57] ABSTRACT

Disclosed are imidazoles as inhibitors of acylCoA:-cholesterol acyltransferase (ACAT), processes for their preparation, pharmaceutical compositions, and their use as antihypercholesterolemics and/or antiatherosclerotics.

9 Claims, No Drawings

IMIDAZOLES FOR THE TREATMENT OF ATHEROSCLEROSIS

FIELD OF THE INVENTION

This invention relates to imidazoles as inhibitors of acyl-CoA: cholesterol acyltransferase (ACAT), pharmaceutical compositions containing them, processes for their preparation, and their use as antihypercholesterolemic and/or antiatherosclerotic agents.

BACKGROUND OF THE INVENTION

Hypercholesterolemia is an established risk factor in the development of atherosclerosis. Therapeutic agents which control the level of serum cholesterol have proven to be effective in the treatment of coronary artery disease. While agents exist that can modulate circulating levels of cholesterol-carrying lipoproteins, these agents have little or no effect on the intestinal absorption of cholesterol. Dietary cholesterol can increase the level of serum cholesterol to levels which place an individual at increased risk for the development or exacerbation of atherosclerosis. Since much of the free or unesterified cholesterol that is absorbed by intestinal mucosal cells must first be esterified by ACAT prior to its incorporation and secretion into the bloodstream in large lipoprotein particles called chylomicrons, inhibition of ACAT can reduce the absorption of dietary cholesterol. In addition, the accumulation and storage of cholesteryl esters in the arterial wall is associated with increased activity of ACAT. Inhibition of the enzyme is expected to inhibit the formation or progression of atherosclerotic lesions in mammals.

There are an increasing number of patents in the literature disclosing compounds which are useful as ACAT inhibitors in particular and antiatherosclerotic agents in general. For example, U.S. Pat. No. 4,623,662, issued to DeVries on Nov. 18, 1986, discloses ureas and thioureas as ACAT inhibitors useful for reducing the cholesterol ester content of an arterial wall, inhibiting atherosclerotic lesion development, and/or treatment of mammalian hyperlipidemia. U.S. Pat. No. 4,722,927, issued to Holmes on Feb. 2, 1988, discloses disubstituted pyrimidineamides of oleic and linoleic acids as ACAT inhibitors useful for inhibiting intestinal absorption of cholesterol. U.S. Pat. No. 4,824,843, issued to Hoefle et al. on Apr. 25, 1989, and the related U.S. Pat. No. 4,882,357, issued to Creger et al. on Nov. 21, 1989, disclose a series of substituted N-phenyl-2,2-dimethyl-5-aryloxypentanamides, which prevent the intestinal absorption of cholesterol in mammals by inhibiting ACAT. European Patent Application 325,397, filed by Ito on Jul. 26, 1989, discloses a series of compounds consisting of two N-cycloalkyl-N'-arylurea units linked at nitrogen by a dialkylphenyl unit, which are inhibitors of the ACAT enzyme. U.S. Pat. No. 4,868,210, issued to Trivedi on Sep. 19, 1989, and the related European Patent Applications 335,374 filed by Trivedi on Mar. 30, 1988, and 386,487, filed by Trivedi on Feb. 9, 1989, disclose certain N-2,6-dialkyl- or N-2,6-dialkoxypheny-N'arylalkyl ureas as potent inhibitors of ACAT. European Patent Application 354,994, filed by Meguro and Ikeda on Feb. 21, 1990, discloses certain N-aryl-N'-quinolin-4-yl ureas as ACAT inhibitors. European Patent Application 370,740, filed by Jackson et al. on Nov. 21, 1988, discloses ACAT inhibitors similar in composition to those of DeVries (supra).

U.S. Pat. No. 4,900,744, issued to Billheimer, et al. on Feb. 13, 1990, discloses antihypercholesterolemic thioimidazoles of the formula

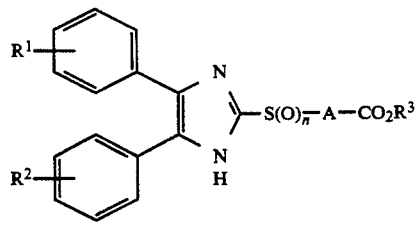

or a pharmaceutically acceptable salt thereof, wherein
$R^1$ and $R^2$ independently are H, F, Cl, $CF_3$, alkyl of 1 to 4 carbon atoms, or alkoxy of 1 to 4 carbon atoms;
A is alkylene of 7-20 carbon atoms or an alkenyl residue thereof with no more than 2 double bonds;
$R^3$ is H, $CH_3$ OR $C_2H_5$; and
n is 0, 1 or 2, such as 8-(4,5-diphenyl-1H-imidazol-2-ylthio)octanoic acid ethyl ester.

European Patent Application EP-A-372,445, filed by Billheimer et al. on Dec. 3, 1989, discloses compounds of formulae

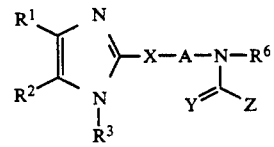

$R^1$ and $R^2$ are selected independently from H, $C_1$–$C_8$ alkyl, $C_3$–$C_8$ branched alkyl, $C_3$–$C_7$ cycloalkyl, $C_4$–$C_{10}$ cycloalkylalkyl, $C_7$–$C_{14}$ araalkyl, 2-, 3- or 4-pyridinyl, 2-thienyl, 2-furanyl, phenyl optionally substituted with 1 to 3 groups selected from F, Cl, Br, OH, $C_1$–$C_4$ alkoxy, $C_1$–$C_4$ alkyl, $C_3$–$C_8$ branched alkyl, $CH_3S(O)_n$, $NO_2$, $CF_3$, or $NR^7R^8$; or
$R^1$ and $R^2$ can also be taken together as

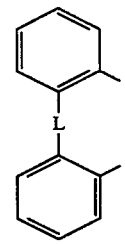

where L is O, $O(CH_2)_{m+1}O$, or $(CH_2)_m$ where m is 0–4;
$R^3$ is H, $C_1$–$C_6$ alkyl, allyl, benzyl, or phenyl optionally substituted with F, Cl, $CH_3$, $CH_3O$, or $CF_3$;
$R^4$ is straight chain $C_1$–$C_8$ alkyl optionally substituted with F; $C_3$–$C_8$ branched alkyl, $C_3$–$C_7$ cycloalkyl, $C_4$–$C_{10}$ cycloalkylalkyl, $C_7$–$C_{14}$ araalkyl where the aryl group is optionally substituted with 1 to 3 groups selected from $C_1$–$C_4$ alkyl or alkoxy, F, Br, Cl, $NH_2$, OH, CN, $CO_2H$, $CF_3$, $NO_2$, $C_1$–$C_4$ carboalkoxy, $NR^7R^8$, or $NCOR^7$; $C_3$–$C_6$ alkenyl or alkynyl, $C_1$–$C_3$ perfluoroalkyl, phenyl optionally substituted with 1 to 3 groups selected from $C_1$–$C_4$ alkyl, $C_3$–$C_8$ branched alkyl, $C_1$-$C_4$ alkoxy, F, Br, Cl, $NH_2$, OH, CN, $CO_2H$, $CF_3$, $NO_2$, $C_1$-$C_4$ carboalkoxy, $NR_7R_8$ or $NCOR_7$; pentafluorophenyl, benzyl optionally substituted with 1 to 3 groups selected from $C_1$-$C_4$ alkyl or alkoxy, F, Br, Cl, $NH_2$, OH, CN, $CO_2H$, $CF_3$, $NO_2$, $C_1$-$C_4$ carboalkoxy, $NR_7R_8$ or $NCOR_7$; 2-, 3- or 4-pyridinyl, pyrimidinyl, or biphenyl;

$R^5$ is H, $C_1$-$C_6$ alkyl, or benzyl;

$R^6$ is $C_1$-$C_8$ alkyl, $C_3$-$C_8$ branched alkyl, $C_3$-$C_7$ cycloalkyl, $C_3$-$C_8$ alkenyl or alkynyl, phenyl optionally substituted with 1 to 3 groups selected from $C_1$-$C_4$ alkyl or alkoxy, F, Br, Cl, $NH_2$, OH, CN, $CO_2H$, $CF_3$, $NO_2$, $C_1$-$C_4$ carboalkoxy, $NR^7R^8$ or $NCOR^7$; pentafluorophenyl, benzyl optionally substituted with 1 to 3 groups selected from $C_1$-$C_4$ alkyl or alkoxy, F, Br, Cl, $NH_2$, OH, CN, $CO_2H$, $CF_3$, $NO_2$, $C_1$-$C_4$ carboalkoxy, $NR^8R^9$ or $NCOR^7$;

$R^7$ and $R^8$ are selected independently from H or $C_1$-$C_4$ alkyl;

X is $S(O)_r$, O, $NR^5$, $CH_2$;

A is $C_2$-$C_{10}$ alkyl, $C_3$-$C_{10}$ branched alkyl, $C_3$-$C_{10}$ alkenyl, or $C_3$-$C_{10}$ alkynyl;

Y is O, S, $H_2$, NH;

Z is $NHR^4$, $OR^4$, or $R^4$;

r is 0-2, or a pharmaceutically acceptable salt thereof.

These compounds are potent in vitro inhibitors of ACAT and are therefore potential antihypercholesterolemic agents.

International Application WO 91/09021 of Bridge et al., discloses compounds of the formula:

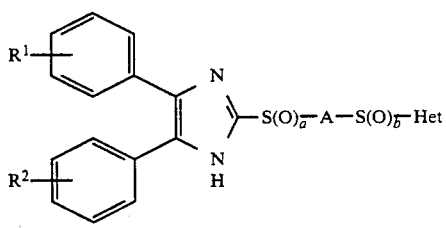

wherein:

A represents methylene or a group —CH$_2$—A'—CH$_2$—, wherein A' represents a direct bond, linear alkanediyl, alkenediyl or alkynediyl, hydroxymethylene, or optionally substituted phenylene;

$R^1$ and $R^2$ each represents hydrogen, halogen, alkyl, alkoxy, alkylthio, alkylamino, carboxy or alkoxycarbonyl;

a and b are 0, 1, or 2;

and Het represents a heterocyclic group containing from 5 to 7 ring atoms chosen from carbon, nitrogen, sulfur and oxygen atoms, and salts thereof.

These compounds are disclosed to be inhibitors of ACAT useful for the treatment of conditions such as atherosclerosis, hyperlipidemia, cholesterol ester shortage disease and atheroma in vein grafts.

International Application WO 91/10662 of Bridge et al., discloses compounds of the formula [DPIM]—S(O)$_p$—W-Y, wherein:

[DPIM] is:

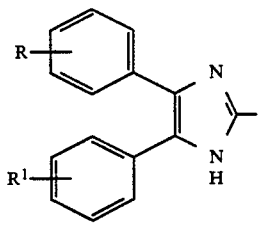

wherein R and $R^1$ each represents hydrogen, halogen, alkyl or alkoxy;

p is 0, 1, or 2;

W represents alkylene;

Y represents an optionally substituted 5- or 6-membered unsaturated ring containing 1 to 4 nitrogen atoms;

and pharmaceutically acceptable acid addition salts thereof.

Such compounds are disclosed to be inhibitors of ACAT.

International Application WO 91/13876 of Bridge et al., discloses compounds of the formula:

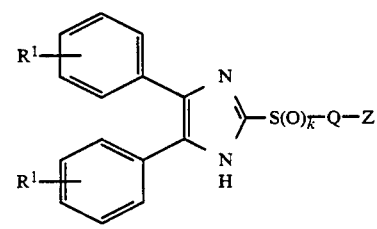

wherein $R^1$ is hydrogen or one or more substituents;

k is 0, 1, or 2;

Q is a straight or branched alkylene group;

Z is a hydrogen or a substituent group;

and pharmaceutically acceptable salts thereof.

Such compounds are disclosed to be inhibitors of ACAT.

U.S. Pat. No. 4,460,598, issued to Lautenschläger et al. on Jul. 17, 1984, discloses compounds of the formula:

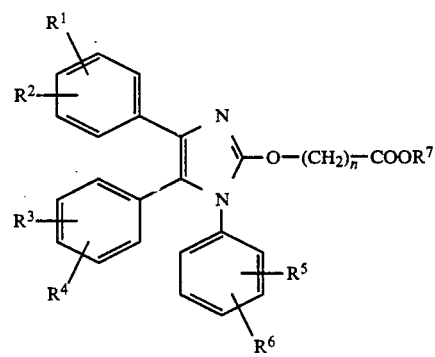

wherein $R^1$, $R^2$, $R^3$, $R^4$, $R^5$ and $R^6$ independently are H, F, Cl, Br, I, alkyl, alkoxy, or $CF_3$, with the proviso that one or several of $R^1$ and $R^2$, $R^3$ and $R^4$, or $R^5$ and $R^6$ taken together represent methylenedioxy;

$R^7$ is H, alkali metal ion, alkyl of 1 to 6 carbon atoms, or benzyl; and n is 0 to 10.

The synthesis and the use of these compounds in the treatment of thromboembolic, inflammatory and/or atherosclerotic diseases is disclosed.

U.S. Pat. No. 4,654,358, issued to Lautenschläger et al. on Mar. 31, 1987, discloses compounds of the formula:

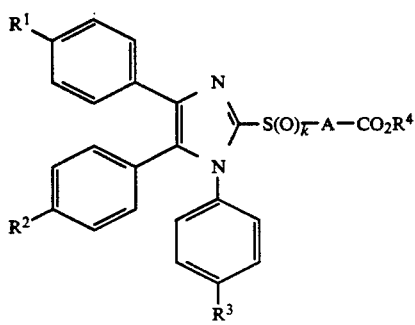

wherein k is 0, 1, or 2, $R^1$, $R^2$ and $R^3$ independently are H, F, Cl, $CH_3$, $CH_3O$, or $CF_3$;

$R^4$ is H, Na, K, $CH_3$, $CH_3CH_2$, $(CH_3)_2CH$, $CH_3(CH_2)_2$, or butyl;

A is $C(CH_3)_2$, $CH(CH_2)_mCH_3$, $(CH_2)_n$, or $(CH_2)_{n-2}CH(CH_3)$;

m is 0 to 8; and n is 2 to 10.

The synthesis and the use of these compounds in the treatment of inflammatory diseases, diseases of lipid metabolism, and/or hyperlipidemic diseases is disclosed. German Laid Open Application No. DE 3504679, Lautenschläger et al., published Aug. 14, 1986, discloses compounds of the formula:

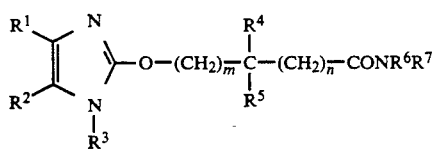

wherein $R^1$, $R^2$ and $R^3$ independently are H, alkyl of 1 to 6 carbon atoms, cycloalkyl of 1 to 6 carbon atoms, or

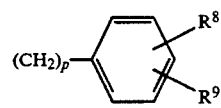

$R^4$ and $R^5$ independently are H, $C_6H_5$, or alkyl of 1 to 9 carbon atoms;

$R^6$ and $R^7$ independently are H, OH, saturated or unsaturated alkyl, cycloalkyl, or hydroxyalkyl of 1 to 10 carbon atoms,

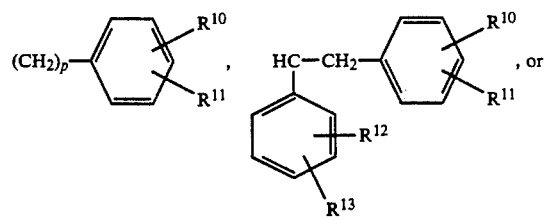

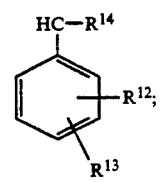

$R^8$, $R^9$, $R^{10}$, $R^{11}$, $R^{12}$ and $R^{13}$ independently are H, F, Cl, Br, $NO_2$, $CH_3CONH$, OH, alkyl of 1 to 3 carbon atoms, $CF_3$, and alkoxy of 1 to 3 carbon atoms, with the proviso that $R^8$ and $R^9$, $R^{10}$ and $R^{11}$, or $R^{12}$ and $R^{13}$ taken together represent methylenedioxy;

$R^{14}$ is alkyl of 1 to 2 carbon atoms;

m and n taken together represent a whole number from to 9;

p is 0 to 2;

s is 0 to 2; and t is 0 or 2.

The synthesis and the use of these compounds in the treatment of thromboembolic, inflammatory, atherosclerotic, and lipid metabolism diseases in general is disclosed.

German Laid Open Application No. DE 3504680, Lautenschläger et al., published Aug. 14, 1986, discloses compounds of the formula:

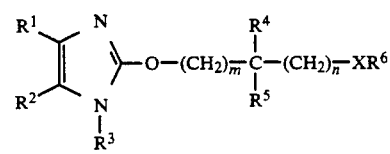

wherein $R^1$, $R^2$ and $R^3$ independently are H, alkyl of 1 to 6 carbon atoms, cycloalkyl of 1 to 6 carbon atoms, or

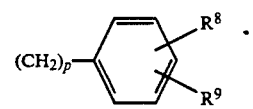

$R^1$ and $R^2$ can be taken together with the carbon atoms in the 4 and 5 position of the imidazole ring to represent a carbocyclic five- or six-membered aromatic or partially hydrogenated ring which may be substituted by $R^8$ or $R^9$;

$R^4$ and $R^5$ independently are H, $C_6H_5$, or alkyl of 1 to 9 carbon atoms;

$R^6$ is alkyl, cycloalkyl, or hydroxyalkyl of 1 to 20 carbon atoms, H, alkali metal if X is —COO—, 1-phenethyl, or

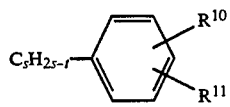

R[7] is H, OH if X is —CONR[7]—, or alkyl of 1 to 4 carbon atoms;

R[8], R[9], R[10] and R[11] are independently H, Cl, F, Br, NO$_2$, CH$_3$CONH, OH, alkyl of 1 to 3 carbon atoms, CF$_3$, or alkoxy of 1 to 3 carbons, or R[8] and R[9] or R[10] and R[11] taken together represent methylenedioxy;

X is a bond, O, OC(=O)O, C(=O)O, CONR[7], OC(=O), or OC(=O)NR[7];

m and n taken together represent a whole number from 0 to 9;

p is 0 to 2;

s is 0 to 2; and t is 0 or 2.

The synthesis and the use of these compounds in the treatment of thromboembolic, inflammatory, atherosclerotic, and lipid metabolism diseases in general is disclosed.

Durant et al., U.S. Pat. No. 4,228,291, issued Oct. 14, 1980, teaches compounds of the formula:

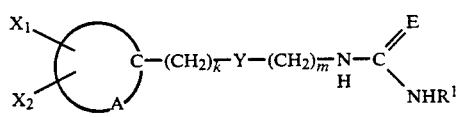

wherein:

A together with the carbon atom form an unsaturated heterocyclic nucleus which may be an imidazole, pyrazole, pyrimidine, pyrazine, pyridazine, thiazole, isothiazole, oxazole, isoxazole, triazole, thiadiazole, benzimidazole, or 5,6,7,8-tetrahydro-imidazol[1,5-a]pyridine ring;

X$_1$ is H, lower alkyl, hydroxyl, trifluoromethyl, benzyl, halogen, amino, or

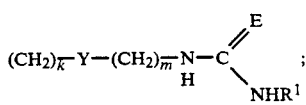

X$_2$ is H, or when X$_1$ is lower alkyl lower alkyl or halogen;

k is 0 to 2 and m is 2 or 3, provided that the sum of k and m is 3 or 4;

Y is O, S, or NH;

E is NR[2];

R[1] is H, lower alkyl or di-lower alkyl amino-lower alkyl;

and R[2] is H, nitro, or cyano.

The compounds are said to be antihistamines of the H$_2$ receptor blocking type, as well as having antiinflammatory activity.

White U.S. Pat. No. 4,413,130, Nov. 1, 1983, discloses histamine H$_2$ receptor antagonists of the formula:

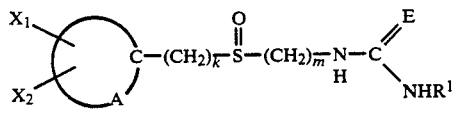

wherein

A together with the carbon atom form an unsaturated heterocyclic nucleus which may be an imidazole, pyridine, thiazole, isothiazole, oxazole, isoxazole, pyrazole, triazole, thiadiazole, pyrimidine, pyrazine or pyridazine;

X$_1$ and X$_2$ may be H, lower alkyl, trifluoromethyl, hydroxyl, halogen, amino, or X$_1$ and X$_2$ and at least two of the atoms comprising A may form a further ring;

k is 0 to 2 and m is 2 or 3, provided that the sum of k and m is 3 or 4;

E is O, S, or NR[2];

R[1] is H, lower alkyl, acyl, or dialkylamino-alkyl;

and R[2] is H, NO$_2$, CN, alkansulphonyl or arenesulphonyl.

There are no known literature references disclosing the imidazoles of this invention, their use as ACAT inhibitors, or their use to lower cholesterol or in the treatment of atherosclerosis.

DETAILED DESCRIPTION OF THE INVENTION

The present invention provides novel compounds of Formula (I), processes for their preparation, pharmaceutical compositions containing such heterocyclic compounds, and therapeutic methods for their use as antihypercholesterolemic and/or antiatherosclerotic agents.

This invention provides compounds of Formula (I):

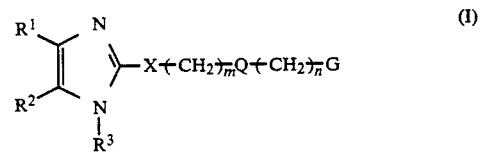

and stereoisomers and pharmaceutically acceptable salts thereof wherein:

X is S(O)$_p$, CH$_2$, or NR[4];

Q is O, S(O)$_q$, or

Y is O, S, or H$_2$;

Z is NHR[5], OR[5] or R[5];

G is selected from one of three heterocyclic groups:

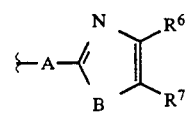

wherein:

A is CH$_2$, O, S(O)$_r$ or NR[8]; and

B is O, S, or NR[9];

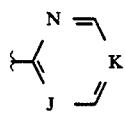

wherein:
J and K are independently N or CH; and

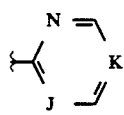

may be optionally substituted with 1-2 $R^{13}$;

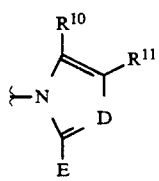

wherein:
D is N or $CR^{12}$;
E is $R^{13}$, halogen, $S(O)_sCH_3$, $NR^{14}R^{15}$, or $OR^{21}$;
$R^1$, $R^2$, $R^6$, $R^7$, $R^{10}$, $R^{11}$, $R^{12}$, $R^{13}$ and $R^{20}$ are selected independently from H, $C_1$-$C_8$ alkyl, $C_3$-$C_8$ branched alkyl, $C_3$-$C_7$ cycloalkyl, $C_4$-$C_{10}$ cycloalkylalkyl, $C_7$-$C_{14}$ aralkyl, pyridyl, thienyl, furanyl, or phenyl; each being optionally substituted with 1-3 groups independently selected from F, Cl, Br, $S(O)_tCH_3$, $NO_2$, $CF_3$, or $NR^{15}R^{16}$;
$R^3$ is H, $C_1$-$C_6$ alkyl, allyl, benzyl, or phenyl; each being optionally substituted with F, Cl, $CH_3$, $OCH_3$, or $CF_3$;
$R^4$, $R^8$, $R^9$, $R^{14}$, $R^{15}$, and $R^{16}$ are selected independently from H, $C_1$-$C_8$ alkyl, benzyl, or phenyl;
$R^5$ and $R^{21}$ are independently selected from $C_1$-$C_8$ alkyl, $C_3$-$C_8$ branched alkyl, $C_3$-$C_7$ cycloalkyl, $C_4$-$C_{10}$ cycloalkylalkyl, $C_7$-$C_{14}$ aralkyl, phenyl (phenyl being optionally substituted with 1-3 groups independently selected from $C_1$-$C_4$ alkyl, $C_3$-$C_8$ branched alkyl, F, Cl, $C_1$-$C_4$ alkoxy, or CN), pyridyl, pyrrolidyl, pyrimidyl, or imidazolyl;
$R^6$ and $R^7$ may also be taken together to form a six-membered aromatic ring, containing 0-2 nitrogen atoms;
$R^{10}$ and $R^{11}$ may also be taken together to form a six-membered aromatic ring, containing 0-2 nitrogen atoms;
$R^{12}$ and $R^{13}$ may also be taken together to form a six-membered aromatic ring, containing 0-2 nitrogen atoms;
n is 0-5;
m is 2-8;
p, q, r, s, and t are independently 0-2;
with the proviso that when $R^1$ and $R^2$ are phenyl and X is $S(O)_p$ and Q is $S(O)_q$ and G is

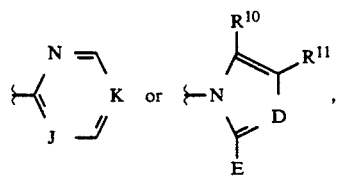

then n cannot be 0.

Preferred are compounds of Formula (I), wherein:
X is $S(O)_p$ or $NR_4$;
Q is O, $S(O)_q$ or

Y is O or $H_2$;
Z is $NHR^5$, $OR^5$, or $R^5$;
G is selected from one of three heterocyclic groups:

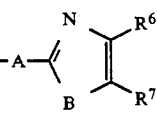

wherein:
A is $CH_2$, O, $S(O)_r$, or $NR^8$; and
B is O, S or $NR^9$;

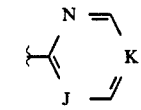

wherein:
J and K are independently N or CH; or

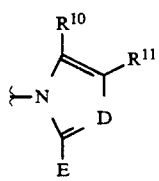

wherein:
D is N;
E is $R^{13}$, $C_1$-$C_4$ alkoxy, $S(O)_sCH_3$, or $NHR^{15}$;
$R^1$, $R^2$, $R^6$, $R^7$, $R^{10}$, $R^{11}$, $R^{12}$, and $R^{13}$ are selected independently from H, $C_1$-$C_8$ alkyl, $C_3$-$C_8$ branched alkyl, $C_3$-$C_7$ cycloalkyl, pyridyl, thienyl, furanyl, or phenyl; phenyl being optionally substituted with 1-3 groups independently selected from $C_1$-$C_4$ alkoxy, $C_1$-$C_4$ alkyl, $C_3$-$C_8$ branched alkyl, $CH_3S(O)_t$, F, or $NR^{15}R^{16}$;
$R^3$ is H, $CH_3$, or phenyl;
$R^4$, $R^8$, $R^9$, $R^{14}$, $R^{15}$, and $R^{16}$ are selected independently from H, $C_1$-$C_8$ alkyl, benzyl, or phenyl;
$R^5$ is independently selected from $C_1$-$C_8$ alkyl, $C_3$-$C_8$ branched alkyl, $C_3$-$C_7$ cycloalkyl, $C_4$-$C_{10}$ cycloalkylalkyl, $C_7$-$C_{14}$ aralkyl, phenyl (phenyl being optionally substituted with 1-3 groups independently selected from $C_1$-$C_4$ alkyl, $C_3$-$C_8$ branched alkyl, F, Cl, $C_1$–$C_4$ alkoxy, or CN), pyridyl, pyrrolidyl, pyrimidyl, or imidazolyl;

$R^6$ and $R^7$ may also be taken together to form a six-membered aromatic ring, containing 0–2 nitrogen atoms;

$R^{10}$ and $R^{11}$ may also be taken together to form a six-membered aromatic ring, containing 0–2 nitrogen atoms;

n is 0–5;
m is 2–8;
p, q, r, s, and t are independently 0–2.

More preferred are compounds of Formula (I), wherein:

X is $S(O)_p$;
Q is O or

Y is O;
Z is $NHR^5$ or $R^5$;
G is selected from one of two heterocyclic groups:

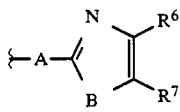

wherein:
A is $S(O)_r$ or $NR^8$; and
B is O, S or $NR^9$; or

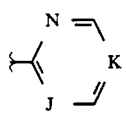

wherein:
K is CH, and
J is N or CH;

$R^1$, $R^2$, $R^6$, and $R^7$ are selected independently from H, $C_1$–$C_8$ alkyl, $C_3$–$C_8$ branched alkyl, $C_3$–$C_7$ cycloalkyl, or phenyl, phenyl being optionally substituted with 1–3 groups independently selected from $C_1$–$C_4$ alkoxy, $C_1$–$C_4$ alkyl, $C_3$–$C_8$ branched alkyl, $S(O)_tCH_3$, F, or $NR^{15}R^{16}$;

$R^3$ is H;
$R^8$, $R^9$, $R^{14}$, $R^{15}$, and $R^{16}$ are selected independently from H, $C_1$–$C_8$ alkyl, benzyl, or phenyl;

$R^5$ is independently selected from $C_1$–$C_8$ alkyl, $C_3$–$C_8$ branched alkyl, $C_3$–$C_7$ cycloalkyl, $C_4$–$C_{10}$ cycloalkylalkyl, $C_7$–$C_{14}$ aralkyl, phenyl (phenyl being optionally substituted with 1–3 groups independently selected from $C_1$–$C_4$ alkyl, $C_3$–$C_8$ branched alkyl, F, Cl, $C_1$–$C_4$ alkoxy, or CN), pyridyl, pyrrolidyl, pyrimidyl, or imidazolyl;

$R^6$ and $R^7$ may also be taken together to form a six-membered aromatic ring, containing 0–2 nitrogen atoms;
n is 0–5;
m is 2–8;
p, q, r, s, and t are independently 0–2.

Further preferred compounds of the present invention are compounds of Formula (I), wherein:

X is $S(O)_p$;
Q is

Y is O;
Z is $NHR^5$ or $R^5$;
G is selected from one of two heterocyclic groups:

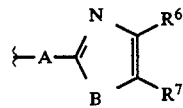

wherein:
A is $S(O)_r$, and
B is O or $NR_9$; or

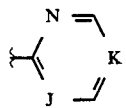

wherein:
J and K are CH;
$R^1$, $R^2$, $R^6$, and $R^7$ are selected independently from H or phenyl, phenyl being optionally substituted with 1–3 groups independently selected from $OCH_3$, $S(O)_tCH_3$, or $N(CH_3)_2$;

$R^6$ and $R^7$ may also be taken together to form a benzene ring;
n is 0–5;
m is 4–6;
p, r, and t are independently 0–2.

Specific compounds of interest are:
1,1-bis[5-(4,5-bis(4-methoxyphenyl)-1H-imidazol-2-ylthio)]pentyl-3-(2-methylethyl)-urea;
1-[5-(4,5-bis(4-methoxyphenyl)-1H-imidazol-2-ylthio)]-pentyl-1-[5-(4,5-diphenyl-1H-imidazol-2-ylthio)]pentyl-3-(2-methylethyl)-urea;
1-[5-(4,5-bis(4-dimethylaminophenyl)-1H-imidazol-2-ylthio)]pentyl-3-(2,4-difluorophenyl)-1-[5-(4,5-diphenyl-1H-imidazol-2-ylthio)]pentyl-urea;
1-[5-(4,5-bis(4-dimethylaminophenyl)-1H-imidazol-2-ylthio)]pentyl-3-(2-methylethyl)-urea;
N-(5-1H-benzimidazol-2-ylthio)pentyl-N-[5-(4,5- diphenyl-1H-imidazol-2-ylthio)]pentyl-benzamide;
1-[5-(4,5-bis(4-methoxyphenyl)-1H-imidazol-2-ylthio)]-pentyl-3-(2,4-difluorophenyl)-1-[2-(2-pyridyl)]ethyl-urea;
1-[5-(4,5-bis(4-methoxyphenyl)-1H-imidazol-2-ylthio)]-pentyl-3-(2-methylethyl)-1-[2-(2-pyridyl)]ethylurea;
1-[5-(4,5-bis(4-methoxyphenyl)-1H-imidazol-2-ylthio)]-pentyl-3-(2-methylethyl)-1-(2-pyridyl)methylurea;
1-[5-(4,5-bis(4-methoxyphenyl)-1H-imidazol-2-ylthio)]pentyl-3-(2,4-difluorophenyl)-1-(2-pyridyl)methyl-urea;
3-(2,4-difluorophenyl)-1-[5-(4,5-diphenyl-1H-imidazol-2-ylthio)]pentyl-1-(2-pyridyl)-urea.

The compounds described above are useful as antiatherosclerotic and antihypercholesterolemic agents in a mammal when administered as pharmaceutical compositions to a mammal in need of treatment with such antiatherosclerotic and antihypercholesterolemic agents. The present invention includes pharmaceutical compositions containing an effective ACAT-inhibiting or antiatherosclerotic amount of the above described compounds of Formula I. The present invention also includes methods of treating hypercholesterolemia or atherosclerosis in a mammal comprising administering to the mammal a therapeutically effective amount of a compound of Formula I described above.

The compounds herein described may have asymmetric centers. All chiral, diastereomeric, and racemic forms are included in the present invention. Many geometric isomers of olefins, C=N double bonds, and the like can also be present in the compounds described herein, and all such stable isomers are contemplated in the present invention.

When any variable (for example, $R^1$ through $R^{21}$) occurs more than one time in any constituent or structure herein, its definition on each occurrence is independent of its definition at every other occurrence. Also, combinations of substituents and/or variables are permissible only if such combinations result in stable compounds.

As used herein, "alkyl" is intended to include both branched and straight-chain saturated aliphatic hydrocarbon groups having the specified number of carbon atoms; "alkoxy" represents an alkyl group of indicated number of carbon atoms attached through an oxygen bridge; "cycloalkyl" is intended to include saturated ring groups, such as cyclopropyl, cyclobutyl, cyclopentyl, cyclohexyl, cycloheptyl and cyclooctyl; and "bicycloalkyl" is intended to include saturated bicyclic ring groups such as [3.3.0]bicyclooctane, [4.3.0]bicyclononane, [4.4.0]bicyclodecane (decalin), [2.2.2]bicyclooctane, and so forth. "Alkenyl" is intended to include hydrocarbon chains of either a straight or branched configuration and one or more unsaturated carbon-carbon bonds which may occur in any stable point along the chain, such as ethenyl, propenyl, and the like; and "alkynyl" is intended to include hydrocarbon chains of either a straight or branched configuration and one or more triple carbon-carbon bonds which may occur in any stable point along the chain, such as ethynyl, propynyl and the like. "Halo" as used herein refers to fluoro, chloro, bromo, and iodo; and "counterion" is used to represent a small, negatively charged species such as chloride, bromide, hydroxide, acetate, sulfate, and the like.

As used herein, "aryl" or "aromatic residue" is intended to mean phenyl or naphthyl; "carbocyclic" is intended to mean any stable 5- to 7- membered monocyclic or bicyclic or 7- to 14-membered bicyclic or tricyclic carbon ring, any of which may be saturated, partially unsaturated, or aromatic, for example, indanyl or tetrahydronaphthyl (tetralin).

As used herein, the term "heterocycle" is intended to mean a stable 5- to 7- membered monocyclic or bicyclic or 7- to 10-membered bicyclic heterocyclic ring which is either saturated or unsaturated, and which consists of carbon atoms and from 1 to 3 heteroatoms selected from the group consisting of N, O and S and wherein the nitrogen and sulfur heteroatoms may optionally be oxidized, and the nitrogen may optionally be quaternized, and including any bicyclic group in which any of the above-defined heterocyclic rings is fused to a benzene ring. The heterocyclic ring may be attached to its pendant group at any heteroatom or carbon atom which results in a stable structure. The heterocyclic rings described herein may be substituted on carbon or on a nitrogen atom if the resulting compound is stable. Examples of such heterocycles include, but are not limited to, pyridyl, pyrimidinyl, furanyl, thienyl, pyrrolyl, pyrazolyl, imidazolyl, tetrazolyl, benzofuranyl, benzothiophenyl, indolyl, indolenyl, quinolinyl, isoquinolinyl or benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl or octahydroisoquinolinyl. The term "substituted", as used herein, means that an one or more hydrogen on the designated atom is replaced with a selection from the indicated group, provided that the designated atom's normal valency is not exceeded, and that the substitution results in a stable compound.

By "stable compound" or "stable structure" is meant herein a compound that is sufficiently robust to survive isolation to a useful degree of purity from a reaction mixture, and formulation into an efficacious therapeutic agent.

As used herein, "pharmaceutically acceptable salts and prodrugs" refer to derivatives of the disclosed compounds that are modified by making acid or base salts, or by modifying functional groups present in the compounds in such a way that the modifications are cleaved, either in routine manipulation or in vivo, to the parent compounds. Examples include, but are not limited to, mineral or organic acid salts of basic residues such as amines; alkali or organic salts of acidic residues such as carboxylic acids; acetate, formate and benzoate derivatives of alcohols and amines; and the like.

Pharmaceutically acceptable salts of the compounds of the invention can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th, ed., Mack Publishing Company, Easton, Pa., 1985, p. 1418, the disclosure of which is hereby incorporated by reference.

SYNTHESIS

The novel compounds of Formula (I) may be prepared using the reactions and techniques described in this section. The reactions are performed in solvents appropriate to the reagents and materials employed and are suitable for the transformations being effected. Also, in the description of the synthetic methods provided below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the educt molecule must be compatible with the reagents and reactions proposed. Not all compounds of Formula (I) falling into a given class may be compatible with some of the reaction conditions required in some of the methods described. Such restrictions to the substituents which are compatible with the reaction conditions will be readily apparent to one skilled in the art and alternate methods must then be used.

The method of synthesis of compounds of Formula (I) will depend largely upon the choice of the groups Q and G. For example, Schemes I and II show routes for syntheses of compounds wherein Q is O or S(O)$_q$, G is chosen from Groups I (wherein A is O or S(O)$_r$) or III, and X is O or S(O)$_p$. Readily-available diglycols (compound 1) are converted to di-halogen ethers (compound 2) by standard means. Alcohols can be converted to chlorides by many reagents, including triphenylphosphine in carbon tetrachloride or hexachloroethylene, thionyl chloride or phosphorus oxychloride. Conversion to bromides is achieved by such reagents as phosphorus tribromide, carbon tetrabromide/triphenylphosphine or thionyl bromide. Iodides are prepared from alcohols by such reagents as triphenylphosphine/iodine or iodotrimethylsilane. Alternatively, the alcohol can be first converted to a toluenesulfonate ester (using toluenesulfonyl chloride and an amine base such as pyridine) or a similar group. This group can be displaced by treatment with an alkali iodide salt. The resulting haloethers (compound 2) can be allowed to react with an imidazole-containing compound (compound 3, X=O or S) to prepare compound 4. This transformation can be accomplished by the use of the imidazole and an inorganic base such as potassium carbonate in a solvent such as tetrahydrofuran at reflux temperature. Likewise, the salt of the imidazole, available from the reaction of compound 3 with an alkali hydride such as sodium hydride in a polar solvent such as dimethylformamide, may be used. (These conditions will be used in other transformations in this section, and will be referred to as "standard alkylation" conditions.) The reaction to prepare compound 4 is particularly successful when M is Cl, and then the amount of dialkylation is minimized. Halide 4 can be converted to compound 5 by the reaction conditions just described. Compound 6 can be prepared from compound 4 using the corresponding N—H heterocycle. It may be necessary to form the salt of the N—H heterocycle with a reagent such as sodium hydride, and then introduce compound 4.

Scheme I

HO—(CH$_2$)$_{\overline{m}}$—O—(CH$_2$)$_{\overline{n}}$—OH $\longrightarrow$ M—(CH$_2$)$_{\overline{m}}$—O—(CH$_2$)$_{\overline{n}}$—M 1  2

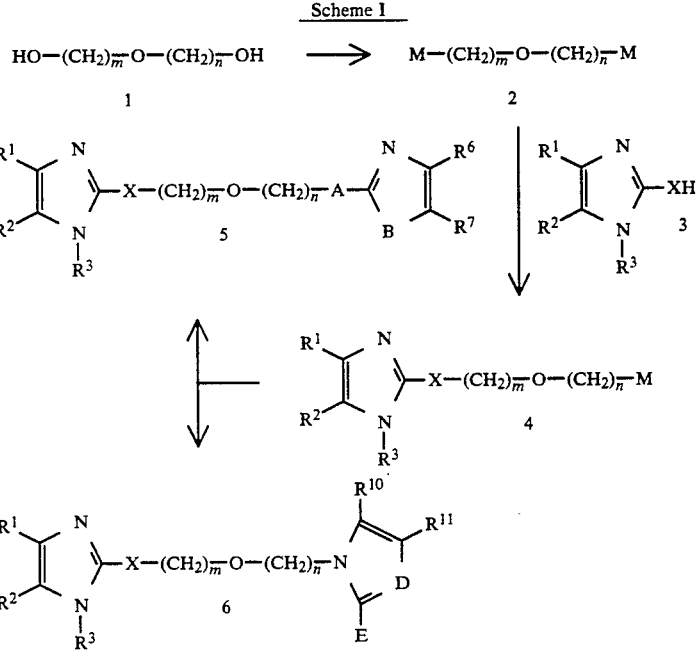

Scheme II

HO—(CH$_2$)$_{\overline{m}}$—S(O)$_{\overline{q}}$—(CH$_2$)$_{\overline{n}}$—OH $\longrightarrow$ M—(CH$_2$)$_{\overline{m}}$—S(O)$_{\overline{q}}$—(CH$_2$)$_{\overline{n}}$—M 7  8

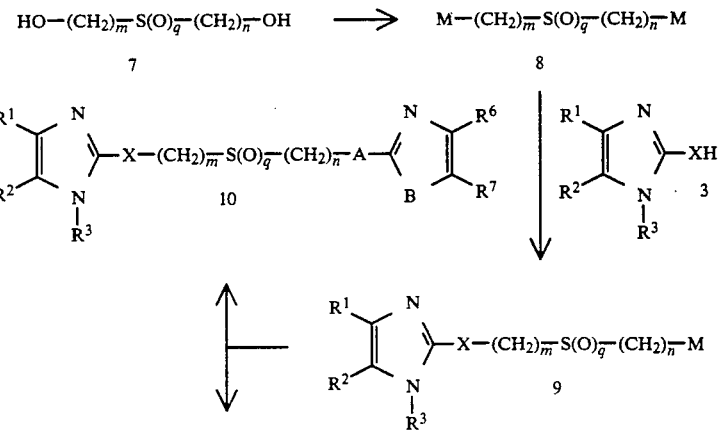

Scheme II

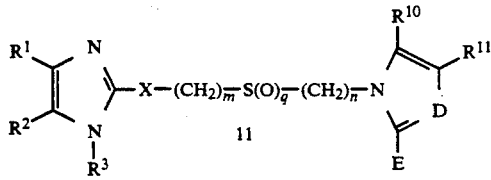

Scheme II presents a route similar to that of Scheme I, employing the sulfur-containing starting material 7. Alternatively, the process may be conducted in a stepwise manner, which is shown in Scheme III. Standard alkylation conditions employing an w-halo ester can be used to prepare ester 12 from imidazole 3. Reduction of the ester group to the alcohol in compound 13 may be achieved using a reagent such as lithium aluminum hydride. The hydroxyl group can be converted to the thiol group using a two-step sequence: the halide 14 is prepared from the acohol 13 as described above; the halide is converted to a thiol group by reagents such as a) thiolacetic acid/potassium carbonate, then sodium hydroxide, or b) thiourea, then sodium hydroxide. Alkylation of the thiol group of compound 15 using the standard alkylation conditions with halides 16 or 17 (both prepared analogously to halide 14) then will afford compounds 10 and 11.

Synthesis of all heterocyclic compounds mentioned in this section can be accomplished using standard chemistry. These methods will be readily familiar to those skilled in the art.

nate, and the like. Control of the extent of the oxidation may be achieved by control of stoichiometry, temperature and/or solvent.

In the cases where either a) X is $NR^4$; or b) G is chosen from Group I where A is $NR^8$, such 2-aminoheterocyclic compounds are often successfully prepared by the strategy shown in Scheme IV, employing 2-substituted heterocycles 18 and 22 (M in this case is halogen or methylsulfonyl). These compounds may be allowed to react with the amines 19 or 21, respectively (R is a group appropriately-substituted to allow eventual synthesis of the desired compound), using a variety of conditions which may include the use of organic bases such as trialkylamines, inorganic bases such as potassium carbonate, and/or high pressure (1 atm–8000 atm), in polar solvents such as dimethylformamide. The R groups may then be transformed as necessary to the desired substituents by the methods described in this section.

Scheme III

For compounds of Formula (I) with values of p, q, r, s and t that are 1 or 2, the corresponding sulfides may be oxidized to their sulfoxide or sulfone counterparts by the use of such reagents as m-chloroperbenzoic acid, potassium peroxomonosulfate, potassium permanga-

Scheme IV

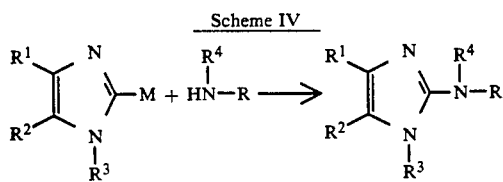

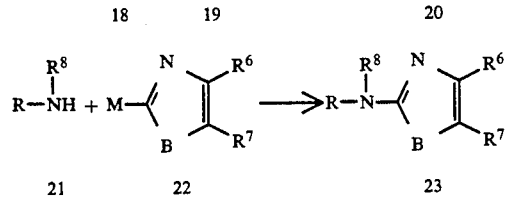

In the cases where either a) X is CH$_2$; or b) G is chosen from Group I wherein A is CH$_2$, such alkyl heterocyclic compounds are often successfully prepared by the strategy shown in Scheme V, employing 2-unsubstituted heterocycles 24 and 27. The corresponding lithio salts 25 and 28 can be prepared from compounds 24 and 27 in situ at low temperatures using strongly-basic reagents such as n-butyllithium/tetramethylethylenediamine. The lithio salts can be treated with an appropriately-substituted halide to afford the 2-alkyl imidazoles 26 and 29, respectively. As above, R may be chosen appropriately to yield the desired compound upon further elaboration.

In the case where Q is O and G is chosen from Group II, a possible synthetic route is shown in Scheme VI. The hydroxyalkyl heterocycle 30 is transformed into the ether compound 31 using a Williamson ether synthesis (sodium metal, followed by an appropriately-substituted halide) or a more modern variation. The R' protecting group in compound 31 is then removed by standard means. The hydroxyl group in compound 32 is transformed to the halogen group M in compound 33 by means discussed above. This halide compound is used in the standard alkylation reaction to afford the ether compound 34. A similarly-designed synthesis of sulfur-based compounds with Group II groups is outlined in Scheme VII. The hydroxyl group in compound 30 is transformed into a halogen group M in compound 35 by means discussed previously. The thiol-bearing compound 15 is then allowed to react with compound 35 using the standard alkylation conditions to afford 36.

Scheme V

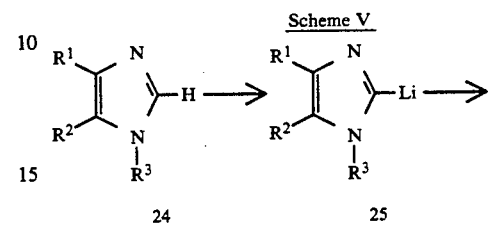

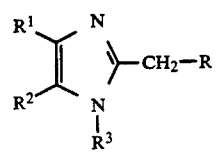

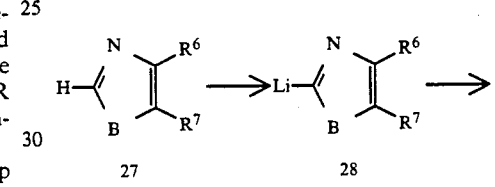

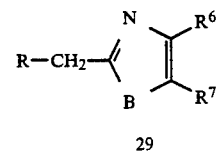

Scheme VI

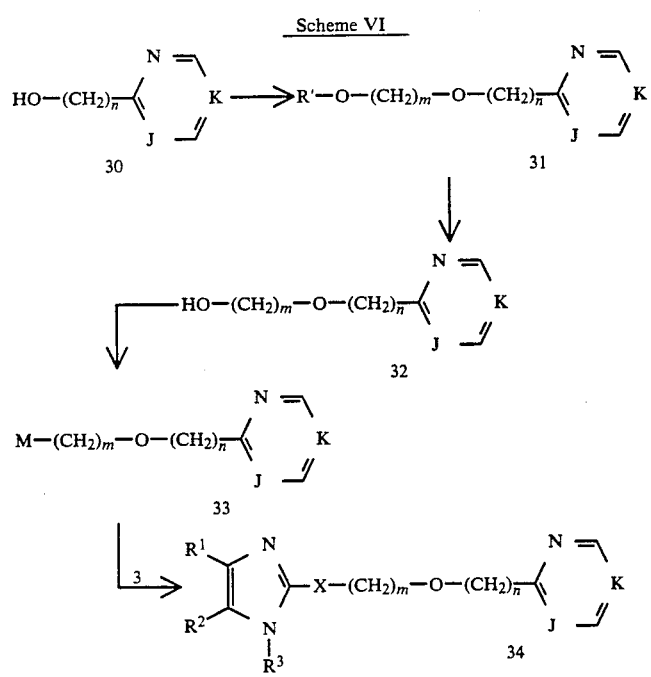

Scheme VII

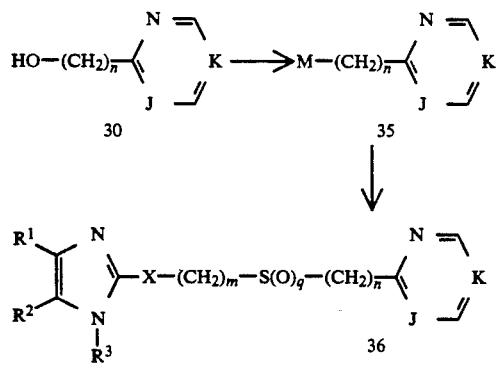

The synthesis of compounds of Formula (I) wherein Q is a nitrogen-based group can be accomplished by functionalizing the amine compound 37 (Scheme VIII) to the appropriate substitution pattern (compound 38). This transformation may be performed with the requisite isocyanate, chloroformate, acid chloride, activated urea or activated carboxylic acid derivative. Compound 38 with a guanidine structure (wherein Y is NH and Z is NHR$^5$) are prepared by the reaction of the secondary amine (compound 37) with an appropriately substituted S-methyl carbamidothioate salt (Rasmussen and Villani, Synthesis 1988, 460). Compound 38 wherein Y is H$_2$ is prepared by the reaction of the corresponding amide (wherein Y is O) with a reducing agent such as lithium aluminum hydride. The compound 38 wherein Y is S and Z is NHR$^5$ can be prepared in an analogous manner by the reaction of the secondary amine (compound 37) with the requisite isothiocyanate. Alternately, compound 38-thioureas or -thioamides (Y is S) can be prepared from the ureas or amides (Y is O) by the action of Lawesson's reagent (Pedersen, Scheibye, Nilsson and Lawesson, Bull. Soc. Chim. Belg. 1978, 87, 223) or diphosphorus pentasulfide.

Three possible means of construction of the requisite amine intermediate (compound 37) are shown in Schemes IX, X, and XI. The first route starts with the coupling of the readily-available aminoalkyl heterocyclic compound 39 with a carboxylic acid chloride bearing another halide atom (compound 40). This reaction can be performed using a base such as triethylamine. Haloamide 41 is then allowed to react with the imidazole 3 in the standard fashion to yield amide 42. The amide carbonyl group may be reduced using reagents such as lithium aluminum hydride to prepare the amine compound 37.

Scheme VIII

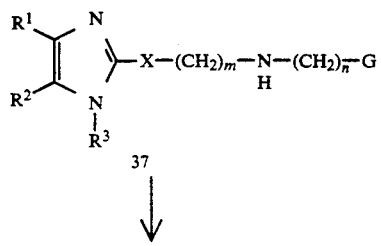

-continued
Scheme VIII

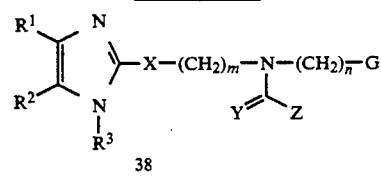

Scheme IX

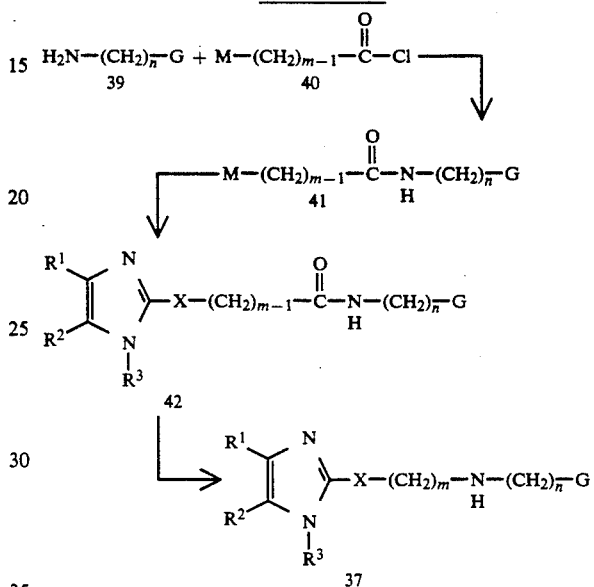

Scheme X

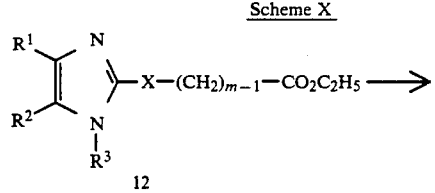

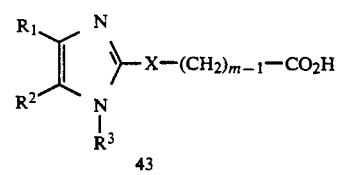

Alternatively, one may hydrolyze the ester compound 12 (Scheme X) to generate the carboxylic acid 43, using such conditions as sodium hydroxide in aqueous/alcoholic solvent. Compounds 43 and 39 may be coupled together to give amide 42. Examples of the coupling agents required for this reaction are disubstituted carbodiimides, N,N'-carbonyldiimidazole, diphenylphosphoryl azide, and the like. For example, the coupling can be carried out with a disubstituted carbodiimide such as dicyclohexylcarbodiimide. Nucleophilic hydroxy compounds such as 1-hydroxy-1H-benzotriazole, which form highly active esters, may be added to catalyze the reaction.

Finally, the same amide-based strategy may be employed, starting with a compound which bears a carboxylic acid group and the G group (compound 44, Scheme XI). The amide coupling reaction conditions, discussed above, may be performed using an aminoalcohol. Hydroxyamide compound 45 thus obtained may be converted to a haloamide (compound 46), which is used in the standard alkylation reaction with imidazole 3 to prepare the amide 47. Amide carbonyl reduction as before then generates the key amine intermediate.

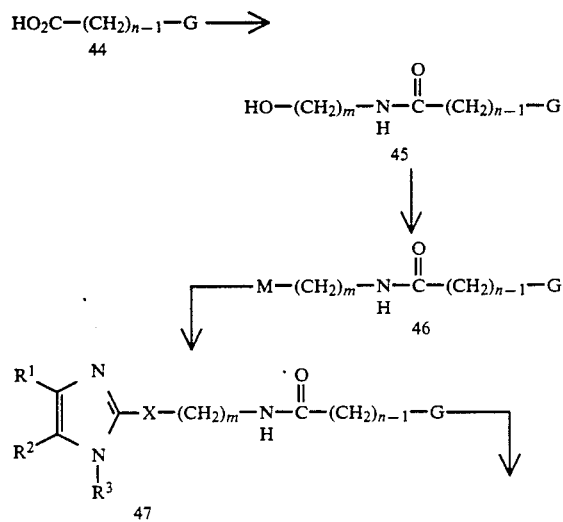

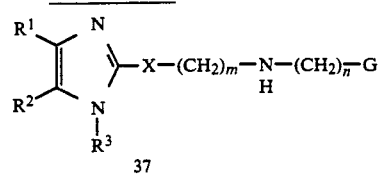

In the special case where G is identical in structure to the imidazole portion of the molecule of Formula (I), another synthetic variation may be used (Scheme XII). The haloacid chloride 40 can be coupled with the amino alcohol 48, using a base such as triethylamine, to afford compound 49. The hydroxyl group is converted to halide as described earlier to yield compound 50. A double alkylation reaction (using the standard conditions) employing two or more equivalents of compound 3, then affords the amide 51. Amide reduction, as before, generated the secondary amine compound 52, and amine functionalization, as before, affords the final product, compound 53.

Yet another strategy is shown in Scheme XIII. Standard alkylation conditions are used to convert compound 49 to amide compound 54. Carbonyl reduction reagents reduce compound 54 to amine 55, which can be selectively functionalized using the conditions discussed earlier. The hydroxyl group of compound 56 is converted to halide (compound 57), and standard alkylation conditions or other methods can be used to introduce the G group in the final product, compound 38.

Preparation of pharmaceutically-suitable salts of Formula (I) can be carried out in accordance with well-known techniques for forming salts. Physiologically-accetable salts include acid addition salts, e.g., hydrochloric, sulfuric, acetic, trifluoroacetic, succinic, citric and benzene sulfonic acid salts.

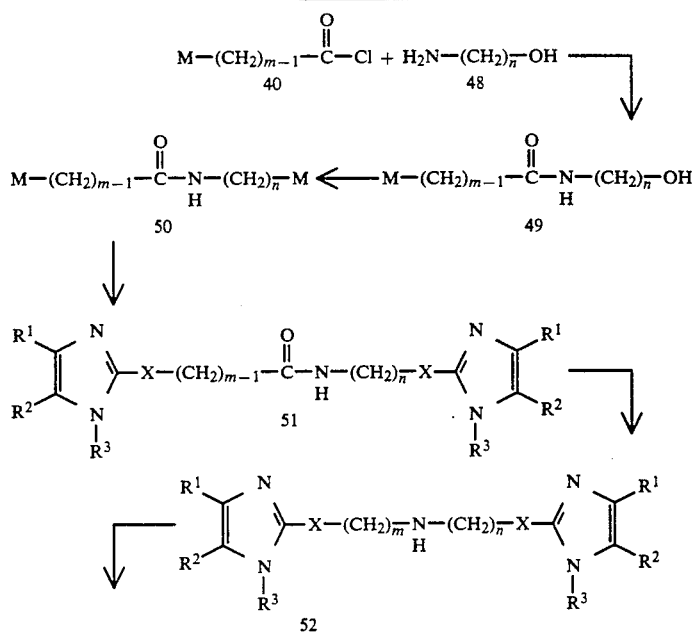

Scheme XII

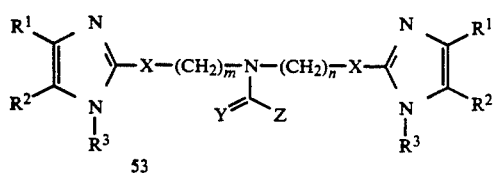

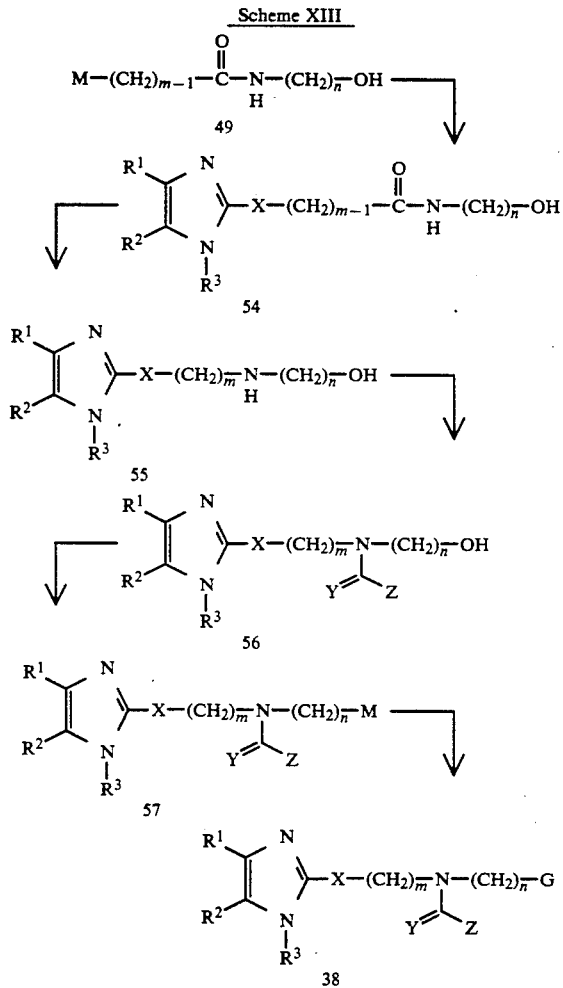

The compounds of this invention and their preparation can be further understood by the following examples, which exemplify but do not constitute a limit of the invention. In these examples, unless otherwise indicated, all temperatures are in degrees centigrade and parts and percentages are by weight.

The phrase "flash chromatography" refers to the method of column chromatographic separation described by Still et al., J. Org. Chem. 1978, 43, 2923.

Spectral data are reported in a format which should be familiar to those skilled in the art, and are consistent with the proposed structure in each case.

EXAMPLE 10

Preparation of
1-[5-(4,5-bis(4-dimethylaminophenyl)-1H-imidazol-2-ylthio)]pentyl-1-[5-(4,5-diphenyl-1H-imidazol-2-ylthio)]pentyl-3-(2-methylethyl)-urea Part A. A solution of 5-aminopentanol (30.0 g, 291 mmol) and triethylamine (50.0 mL, 359 mmol) in tetrahydrofuran (500 mL) was cooled to 0° C., and a solution of 5-bromovaleryl chloride (30.0 mL, 226 mmol) in tetrahydrofuran (200 mL) was added dropwise. After slow warming and stirring for 18 hours, the mixture was poured into water (1 L), and the phases were separated. The aqueous layer was extracted with methylene chloride (2×600 mL). The organic phases were combined, dried over anhydrous magnesium sulfate, filtered and evaporated. The oily product was purified by elution through a silica gel plug with ethyl acetate, and evaporation afforded the product, N-(5-hydroxypentyl)-5-bromopentanamide (47.3 g, 178 mmol, 79%).

Part B. The bromide compound prepared in Part A (26.4 g, 99.2 mmol), 4,5-diphenyl-2-mercapto-1H-imidazole (25.0 g, 99.1 mmol), potassium carbonate (16.4 g, 119 mmol) and tetra-n-butylammonium iodide (7.31 g, 19.8 mmol) was suspended in tetrahydrofuran (200 mL). The solution was heated to reflux for 18 hours, then cooled, and poured into water (400 mL). This mixture was extracted with methylene chloride (2×400 mL). The organic phases were combined, dried over anhydrous magnesium sulfate, filtered and evaporated. The residual oil was separated by flash chromatography (1:1 ethyl acetate-hexane) to afford the product, 5-(4,5-diphenyl-1H-imidazol-2-ylthio)-N-(5-hydroxypentyl)pentanamide, as a waxy solid (6.04 g, 13.8 mmol, 14%). $^1$H NMR (CD$_3$OD): 7.43–7.21 (10H, m); 3.52 (2H, t, J=6 Hz); 3.31 (1H, t, J=2 Hz); 3.13 (2H, t, J=6 Hz); 3.06 (2H, t, J=6 Hz); 2.20 (2H, t, J=7 Hz); 1.80–1.62 (4H, m); 1.58–1.41 (4H, m); 1.39–1.29 (2H, m).

Part C. A slurry of lithium aluminum hydride (1.70 g, 44.8 mmol) in dry tetrahydrofuran (100 mL) was cooled to 0° C., and the amide from Part B above (6.04 g, 13.8 mmol) was added as a solid portionwise over 5 minutes. The ice bath was removed, and the mixture was heated to gentle reflux for 18 hours. After being cooled to 0° C., the reaction was quenched by the careful, sequential addition of water (2 mL), aqueous sodium hydroxide (15%, 6 mL), and water (6 mL). The resulting mixture was filtered through celite, dried over anhydrous potassium carbonate, filtered and evaporated. The product, 5-(4,5-diphenyl-1H-imidazol-2-ylthio)-N-(5-hydroxypentyl)pentanamine, was obtained as a gummy oil (5.84 g, 13.8 mmol, 100%). $^1$H NMR (CDCl$_3$): 7.59–7.40 (4H, m); 7.35–7.20 (6H, m); 3.59 (2H, t, J=6.3 Hz); 3.07 (2H, t, J=7.0 Hz); 2.63–2.50 (4H, m); 1.78–1.30 (14H, m).

Part D. A solution of the amine prepared in Part C above (2.92 g, 6.89 mmol) in methylene chloride (50 mL) was cooled to 0° C., and a solution of isopropylisocyanate (0.70 mL, 7.1 mmol) in methylene chloride (20 mL) was added dropwise. The mixture was allowed to stir and slowly warm over 18 hours, then was evaporated. The residual oil was separated by flash chromatography (1:4 ethyl acetate-hexane) to afford the product, 1-[5-(4,5-diphenyl-1H-imidazol-2-ylthio)pentyl]-1-(5-hydroxypentyl)-3-(1-methylethyl)-urea, as a low-melting solid (3.00 g, 5.90 mmol, 86%). $^1$H NMR (CDCl$_3$): 11.34 (1H, br s); 7.60 (2H, br d, J=7 Hz); 7.48 (2H, br d, J=7 Hz); 7.38–7.20 (6H, m); 4.21 (1H, br d, J=6.6 Hz); 4.02 (1H, br s); 3.82 (1H, octet, J=6.6 Hz); 3.65 (2H, br t, J=7 Hz); 3.32 (2H, t, J=6.4 Hz); 3.12 (2H, t, J=7.5 Hz); 3.01 (2H, t, J=6.6 Hz); 1.81–1.36 (12H, m); 1.06 (6H, d, J=6.6 Hz).

Part E. A solution of the alcohol prepared in Part D above (2.97 g, 5.84 mmol) and carbon tetrabromide (2.71 g, 8.17 mmol) in methylene chloride (20 mL) was cooled to 0° C., and a solution of triphenylphosphine (2.14 g, 8.16 mmol) in methylene chloride (10 mL) was added dropwise. After stirring for 18 hours, the reaction mixture was evaporated, and the residual oil was separated by flash chromatography (1:3 ethyl acetatehexane) to afford the product, 1-bromopentyl-1-[5-(4,5-diphenyl-1H-imidazol-2-ylthio)pentyl]-3-(1-methylethyl)urea, as a low-melting solid (1.82 g, 3.18 mmol, 55%). $^1$H NMR (CDCl$_3$): 7.63–7.20 (10H, m); 4.12 (1H, br s); 3.92 (1H, octet, J=6.4 Hz); 3.41 (2H, t, J=6 Hz); 3.31 (2H, t, J=6 Hz); 3.11 (2H, t, J=7 Hz); 3.02 (2H, t, J=6 Hz); 1.95–1.85 (2H, m); 1.82–1.72 (2H, m); 1.61–1.40 (8H, m); 1.07 (6H, d, J=6.4 Hz).

Part F. A mixture of the bromide prepare in Part E above (1.82 g, 3.18 mmol), 4,5-bis(4- dimethylamino)-phenyl-2-mercapto-1H-imidazole (1.08 g, 3.19 mmol), potassium carbonate (0.57 g, 4.12 mmol) and tetra-n-butylammonium iodide (100 mg) in tetrahydrofuran (30 mL) was heated to reflux for 18 hours. The mixture was cooled and poured into 200 mL water. This was extracted with methylene chloride (2×200 mL), and the extracts were combined, dried over anhydrous magnesium sulfate, filtered and evaporated. The residue was separated by flash chromatography to afford the title product as a solid, which was recrystalized to purity from ether, mp 117°–119° C. $^1$H NMR (CDCl$_3$): 7.60–7.15 (14H, m); 6.63 (4H, d, J=8.8 Hz); 4.25 (1H, br d, J=7 Hz); 3.81 (1H, octet, J=7 Hz); 3.20–2.91 (8H, m); 2.92 (12H, s); 1.72–1.31 (12H, m); 1.04 (6H, d, J=6.6 Hz). Elemental analysis: calc. C 69.53, H 7.29, N 13.51; obs. C 69.29, H 7.24, N 13.57.

EXAMPLE 14

Preparation of 1,1-bis[5-(4,5-bis(4-methoxyphenyl)-1H-imidazol-2-ylthio)]pentyl-3-(2-methylethyl)-urea Part A. A solution of N-(5-hydroxypentyl)-5-bromopentanamide (4.07 g, 15.3 mmol) and carbon tetrabromide (7.61 g, 22.9 mmol) in methylene chloride (75 mL) was cooled to 0° C., and treated with a solution of triphenylphosphine (6.02 g, 22.9 mmol) in methylene chloride (30 mL) dropwise. After stirring for 12 hours, the reaction mixture was evaporated, and the residual oil was separated by flash chromatography (1:1 ethyl acetate-hexane) to afford the oily product, N-(5-bromopentyl)-5-bromopentanamide (1.69 g, 5.14 mmol, 34%). $^1$H NMR (CDCl$_3$): 5.96 (1H, br s); 3.40 (4H, t, J=6.6 Hz); 3.24 (2H, q, J=6.2 Hz); 2.20 (2H, t, J=7.0 Hz); 1.94–1.74 (6H, m); 1.58–1.42 (4H, m).

Part B. A solution of the dibromide prepared in Part A above (1.91 g, 5.80 mmol), 4,5-bis(4-methoxyphenyl)-2-mercapto-1H-imidazole (3.62 g, 11.6 mmol), potassium carbonate (2.08 g, 15.1 mmol) and tetra-n-butylammonium iodide (0.86 g, 2.32 mmol) in tetrahydrofuran (80 mL) was heated to reflux for 14 hours. After cooling, the mixture was poured into water (150 mL), and this was extracted with methylene chloride (150 mL). The aqueous phase was neutralized to pH 7 with aqueous hydrochloric acid (6N), then re-extracted with methylene chloride (150 mL). The extracts were combined, dried over anhydrous magnesium sulfate, filtered and evaporated. The residue was separated by flash chromatography (1:2 acetone-hexane) to afford the product, N-[5-(4,5-bis(4-methoxyphenyl)-1H-imidazol-2-ylthio)pentyl]-5-[4,5bis-(4-methoxyphenyl)-1H-imidazol-2-ylthio)pentyl]pentanamide, as a low-melting solid (4.06 g, 5.13 mmol, 88%). $^1$H NMR (CDCl$_3$): 7.41 (8H, d, J=8.8 Hz); 6.82 (4H, d, J=8.8 Hz); 6.80 (4H, d, J=8.8 Hz); 6.33 (1H, br t, J=6 Hz); 3.78 (12H, s); 3.11–2.94 (6H, m); 2.23 (2H, t, J=6.6 Hz); 1.90–1.30 (10H, m).

Part C. A solution of sodium bis(methoxyethoxy)aluminum hydride (3.30 mL, 3.40M in toluene, 11.3 mmol) in toluene (50 mL) was cooled to 0° C., and a solution of the amide prepared in Part B above (4.06 g, 5.13 mmol) in tetrahydrofuran (50 mL) was added dropwise over 30 minutes. The ice bath was removed, and the solution was heated to mild reflux for 90 minutes. The reaction mixture was allowed to cool, then was stirred for 12 hours. The reaction was quenched by the careful addition of water (10 mL). This mixture was poured into additional water (200 mL), and extracted with methylene chloride (200 mL). The extract was dried over anhydrous potassium carbonate, filtered and evaporated to afford the product, bis[5-(4,5-bis(4-methoxyphenyl)-1H-imidazol-2-ylthio)pentyl]-amine, which formed a solid foam upon vacuum pumping (4.00 g, 5.13 mmol, 100%). $^1$H NMR (CDCl$_3$): 7.42–7.15 (8H, m); 6.83–6.75 (8H, m); 3.80 (12H, m); 3.07–2.95 (6H, m); 2.56–2.50 (2H, m); 1.70–1.30 (12H, m).

Part D. A solution of the amine prepared in Part C above (4.00 g, 5.13 mmol) in methylene chloride (20 mL) was cooled to 0° C., and treated with a solution of isopropylisocyanate (0.60 mL, 6.17 mmol) in methylene chloride (10 mL) dropwise. After stirring 72 hours, the reaction mixture was evaporated, and the residual oil separated by flash chromatography (1:2 acetone-hexane) to afford the title product as a solid foam, after evaporation from ether solution and vacuum pumping, mp 97°–99° C. (2.20 g, 2.55 mmol, 50%). $^1$H NMR (CDCl$_3$): 7.40 (8H, br s); 6.80 (8H, d, J=8.7 Hz); 4.27 (1H, d, J=6 Hz); 3.81 (1H, heptet, J=6.6 Hz); 3.77 (12H, s); 3.16 (4H, t, J=6.7 Hz); 2.95 (4H, t, J=6.6 Hz); 1.75–1.62 (4H, m); 1.56–1.45 (4H, m); 1.42–1.32 (4H,m); 1.04 (6H, d, J=6.6 Hz). Elemental analysis: calc. C 66.79, H 6.77, N 9.74; obs. C 66.73, H 6.74, N 9.45.

EXAMPLE 21

Preparation of N-(5-1H-benzimidazol-2-ylthio)pentyl-N-[5-(4,5-diphenyl-1H-imidazol-2-ylthio)]pentyl-benzamide Part A. A solution of 5-(4,5-diphenyl-1H-imidazol-2-ylthio)-N-(5-hydroxypentyl)-pentanamine (8.10 g, 18.5 mmol) and triethylamine (10.0 mL, 71.7 mmol) in tetrahydrofuran (150 mL) was cooled to 0° C., and a solution of benzoyl chloride (7.00 mL, 60.3 mmol) in tetrahydrofuran (40 mL) was added dropwise. After stirring for 12 hours, the reaction mixture was poured into water (400 mL), and the phases were separated. The aqueous phase was extracted with methylene chloride (400 mL). The organic phases were washed with saturated brine (300 mL), then combined, dried over anhydrous magnesium sulfate, filtered and evaporated. The residue was separated by flash chromatography (1:3 ethyl acetate-hexane) to afford the product, N-(5-benzoyloxypentyl)-N-[5-(4,5-diphenyl-1H-imidazol-2-ylthio)pentyl]-benzamide, as a gummy viscous oil (6.62 g, 10.5 mmol, 57%). $^1$H NMR (CDCl$_3$): 11.32 (1H, br s); 8.00 (2H, br d, J=8 Hz); 7.60-7.20 (18H, m); 4.32 (0.7H, t, J=6.3 Hz); 4.23 (1.3H, t, J=6.3 Hz); 3.58 (1.3H, t, J=6.3 Hz); 3.46 (0.7H, t, J=6.3 Hz); 3.28-3.18 (2H, m); 3.06-2.96 (2H, m); 1.87-1.42 (8H, m); 1.30-1.20 (2H, m). Elemental analysis: calc. C 74.14, H 6.54, N 6.65; obs. C 73.79, H 6.40, N 6.35.

Part B. A solution of the ester/amide compound prepared in part A above (5.65 g, 8.94 mmol) in ethanolic sodium hydroxide (54 mL, 0.25M NaOH in 95:5 ethanol-water, 13.5 mmol) was stirred for 12 hours. The reaction mixture was evaporated, and the residue partitioned between water and methylene chloride (200 mL each). The organic phase was separated, dried over anhydrous magnesium sulfate, filtered and evaporated. The product was purified by flash chromatography (1:1 ethyl acetatehexane) to afford N-[5-(4,5-diphenyl-1H-imidazol-2-ylthio)pentyl]-N-(5-hydroxypentyl)-benzamide (4.71 g, 8.93 mmol, 100%). $^1$H NMR (CDCl$_3$): 8.04 (2H, d, J=8.5 Hz); 7.60-7.18 (13H, m); 3.58 (2H, t, J=6.6 Hz); 3.53 (2H, t, J=6.2 Hz); 3.45 (1H, br s); 3.20 (2H, t, J =7.3 Hz); 3.04 (2H, t, J=6.3 Hz); 1.89-1.40 (12H, m).

Part C. A solution of the alcohol prepared in Part B above (4.71 g, 8.93 mmol) and carbon tetrabromide (4.15 g, 12.5 mmol) in methylene chloride (30 mL) was cooled to 0° C., and treated with a solution of triphenylphosphine (3.28 g, 12.5 mmol) in methylene chloride (30 mL) dropwise. After stirring overnight, the solution was evaporated, and the residue was separated by flash chromatography (1:1 ethyl acetatehexane) to afford the product, N-(5-bromopentyl)-N-[5-(4,5-diphenyl-1H-imidazol-2-ylthio)pentyl]-benzamide, as a low-melting solid (3.71 g, 6.28 mmol, 70%). $^1$H NMR (CDCl$_3$): 11.08 (1H, br s); 7.61-7.20 (15H, m); 3.66-3.00 (8H, m); 1.98-1.40 (12H, m).

Part D. A solution of the bromide prepared in Part C above (1.85 g, 3.13 mmol), 2-mercaptobenzimidazole (0.47 g, 3.13 mmol), potassium carbonate (0.60 g, 4.34 mmol) and tetra-n-butylammonium iodide (0.29 g) in tetrahydrofuran (30 mL) was heated to reflux for 14 hours. The solution was cooled, and poured into water (200 mL). This was extracted with methylene chloride (2 ×150 mL), and the extracts were combined, dried over anhydrous magnesium sulfate, filtered and evaporated. The residual oil was separated by flash chromatography to afford the title product, which was obtained as a solid foam after repeated evaporation from ether solution and vacuum pumping, mp 75°-77° C. (1.84 g, 2.79 mmol, 89%). $^1$H NMR (CDCl$_3$): 11.42 (1H, br s); 10.89 (1H, br s); 7.62-7.09 (19H, m); 3.56-3.39 (2H, m); 3.24-3.07 (4H, m); 3.02-2.93 (2H, m); 1.90-1.14 (12H, m). Elemental analysis: calc. C 70.98, H 6.26, N 10.61; obs. C 71.01, H 6.25, N 10.01.

Compounds Example Number 1-70 listed in Table 1 (below) can be prepared by the procedures described in Examples 10, 14 and 21 employing the appropriately substituted starting materials. In Table 1, R6 and R7 may be taken together to form a ring, as, for example, in Examples 17-46 and 64-70.

EXAMPLE 75

Preparation of 1-[5-(4,5-bis(4-methoxyphenyl)-1H-imidazol-2-ylthio)]pentyl-3-(2,4-difluorophenyl)-1-(2-pyridyl)methyl-urea Part A. A solution of 2-(aminomethyl)pyridine (4.07 g, 37.6 mmol) and triethylamine (7.50 mL, 53.8 mmol) in tetrahydrofuran (100 mL) was cooled to 0° C., then treated with a solution of 5-bromovaleryl chloride (5.00 mL, 37.6 mmol) in tetrahydrofuran (20 mL) dropwise. After stirring for 12 hours, the mixture was poured into water (150 mL) and extracted with methylene chloride (2×150 mL). The extracts were combined, dried over anhydrous magnesium sulfate, filtered and evaporated to afford the oily product, N-(2-pyridylmethyl)-5-bromopentanamide (9.44 g, 34.8 mmol, 93%).

Part B. A solution of the bromide prepared above (5.37 g, 19.8 mmol), 4,5-bis(4-methoxyphenyl)-2-mercapto-1H-imidazole (6.19 g, 19.8 mmol), potassium carbonate (3.56 g, 25.7 mmol) and tetra-n-butylammonium iodide (1.46 g, 3.69 mmol) in tetrahydrofuran (80 mL) was heated to reflux for 14 hours. After cooling, the mixture was poured into water (150 mL), and extracted with methylene chloride (150 mL). The aqueous phase was neutralized to pH 7 with aqueous hydrochloric acid (6N), saturated with sodium chloride, and re-extracted with methylene chloride (150 mL). The extracts were combined, dried over anhydrous magnesium sulfate, filtered and evaporated. The oily residue was separated by flash chromatography (1:1 ethyl acetate-hexane, then 1:4 methanol-ethyl acetate) to afford the product, N-(2-pyridylmethyl)-5-[4,5-bis(4-methoxyphenyl)-1H-imidazol-2-ylthio]-pentanamide, as a gummy semisolid (8.17 g, 16.2 mmol, 82%). $^1$H NMR (CDCl$_3$): 8.46 (1H, dd, J=5.0, 0.8 Hz); 7.60 (1H, ddd, J=7.7, 6.7, 0.8 Hz); 7.43 (4H, d, J=8.8 Hz); 7.15 (1H, dd, J=6.7, 5.0 Hz); 7.07 (1H, d, J=7.7 Hz); 6.81 (4H, d, J=8.8 Hz); 4.28 (2H, d, J=5.1 Hz); 3.78 (6H, s); 2.94 (2H, t, J=6.4 Hz); 2.35 (2H, t, J=6.8 Hz); 1.98-1.87 (2H, m); 1.78-1.60 (2H, m).

Part C. A solution of sodium bis(methoxyethoxy)aluminum hydride (10.3 mL of 3.40M is toluene, 35.1 mmol) in toluene (50 mL) was cooled to 0° C., and a solution of the amide prepared in Part B above (8.03 g, 16.0 mmol) in tetrahydrofuran (50 mL) was added dropwise. After the addition was complete, the ice bath was removed, and the mixture was heated to mild reflux for 2 hours, then cooled to 0° C. The reaction was quenched by the careful addition of aqueous sodium hydroxide (5 mL of 2N), and the mixture was poured into water (200 mL). This was extracted with methylene chloride (200 mL), and the aqueous phase was saturated with sodium chloride and re-extracted with methylene chloride (200 mL). The extracts were combined, dried over anhydrous potassium carbonate, filtered and evaporated to afford the product, 2-[[5-(4,5-bis(4-methoxyphenyl)-1H-imidazol-2-ylthio)pentyl]aminomethyl]pyridine, as a gummy semisolid (7.60 g, 15.6 mmol, 97%). $^1$H NMR (CDCl$_3$): 8.59-8.48 (1H, m); 7.49 (4H, br s); 7.26-7.12 (2H, m); 6.79 (4H, s); 3.78 (6H, s); 3.39-3.29 (2H, m); 3.04 (2H, t, J=7 Hz); 2.43-2.36 (2H, m); 1.80-1.35 (6H, m).

Part D. A solution of the amine prepared in Part C above (3.80 g, 7.78 mmol) in methylene chloride (20 mL) was cooled to 0° C., and treated with a solution of 2,4-difluorophenylisocyanate (1.11 mL, 9.33 mmol) dropwise. After stirring for 14 hours, the solution was evaporated, and the residue was separated by column chromatography (yield 1.56 g, 2.42 mmol, 31%). The title product was purified further by HPLC separation. $^1$H NMR (CDCl$_3$): 10.92 (1H, br s); 8.68-8.60 (1H, m); 7.78-7.59 (2H, m); 7.49 (2H, d, J=8.4 Hz); 7.30 (2H, d, J=8.4 Hz); 7.29-7.20 (2H,m); 6.84 (4H, d, J=8.4 Hz); 6.80-6.55 (2H, m); 4.53 (2H, s); 3.80 (3H, s); 3.78 (3H, s); 3.53 (2H, t, J=6.6 Hz); 2.89 (2H, t, J=6.2 Hz); 1.80-1.30 (6H, m).

Compounds 71-130 in Table 2 (below) can be prepared by the procedure described in Example 75 employing the appropriately substituted starting materials.

EXAMPLE 135

Preparation of
1-[5-[4,5-bis(4-methoxyphenyl)-1H-imidazol-2-ylthio]-pentyl]-1-(3-1H-imidazol-1-yl)propyl-3-(1-methylethyl)-urea Part A. A suspension of 4,5-bis(4-methoxyphenyl)-2-mercapto-1H-imidazole (10.4 g, 33.2 mmol), ethyl 5-bromovalerate (5.00 mL, 31.6 mmol), potassium carbonate (5.50 g, 39.8 mmol), and tetra-n-butylammonium iodide (2 g) in tetrahydrofuran (100 mL) was heated to reflux for 20 hours. The mixture was cooled, and poured into water (400 mL). This was extracted with methylene chloride (2 ×400 mL), and the extracts were combined, dried over anhydrous magnesium sulfate, filtered and evaporated. The residual oil was purified by elution through a short plug of silica gel with ethyl acetate, and evaporation afforded ethyl 5-[4,5-bis(4-methoxyphenyl)-1H-imidazole-2-ylthio]pentanoate (14.4 g, 32.6 mmol, 98%) as a waxy, low-melting solid.

Part B. The ester prepared in Part A above (14.4 g, 32.6 mmol) was stirred in ethanolic sodium hydroxide (240 mL, 0.25N, 60 mmol, about 5% water added) at ambient temperature for 48 hours. The reaction mixture was evaporated, neutralized to pH 7 with small portions of 1N aqueous hydrochloric acid, and saturated with sodium chloride. This mixture was extracted with ethyl acetate (2×200 mL), and the extracts were combined, dried over anhydrous magnesium sulfate, filtered and evaporated to afford 5-[4,5-bis(4-methoxyphenyl)-1H-imidazole-2-ylthio]pentanoic acid as a waxy solid (12.1 g, 29.3 mmol, 90%).

Part C. The acid prepared in Part B above (7.65 g, 18.6 mmol) was taken up in tetrahydrofuran (50 mL), and cooled to 0° C. Solid 1-hydroxybenzo-1H-triazole hydrate (3.03 g, 22.4 mmol) was added in several portions, and the mixture was allowed to stir for 20 minutes. Then, 1-(3-aminopropyl)-1H-imidazole (3.00 mL, 25.1 mmol) was added by syringe. After stirring for 10 minutes, the solution was treated with small portions of dicyclohexylcarbo-diimide (4.62 g, 22.4 mmol) over 10 minutes. The reaction mixture was allowed to stir for 48 hours, then was filtered and evaporated. The residual oil was refiltered and separated by flash chromatography (1:9 methanol-methylene chloride) to afford, upon vacuum pumping, N-[3-(1H-imidazol-1-yl)propyl]-5-[4,5-bis(4-methoxyphenyl)-1H-imidazol-2-ylthio]pentanamide (7.81 g, 15.0 mmol, 81%) as a foam, with a low melting point. $^1$H NMR (CDCl$_3$): 7.46 (1H, s); 7.41 (4H, d, J=8.8 Hz); 6.97 (1H, s); 6.83 (1H, s); 6.80 (4H, d, J=8.8 Hz); 3.81 (2H, t, J=7.0 Hz); 3.78 (6H, s); 3.04 (2H, t, J=5.9 Hz); 2.97 (2H, t, J=7.0 Hz); 2.16 (2H, t, J=7.0 Hz); 1.88-1.58 (6H, m).

Part D. A solution of lithium aluminum hydride (20 mL of 1.0M in tetrahydrofuran, 20.0 mmol) was cooled to 0° C., and a solution of the amide prepared in Part C above (4.08 g, 7.85 mmol) in tetrahydrofuran (20 mL) was added dropwise. The solution was then warmed to reflux for 20 hours, then cooled back to 0° C. and quenched by sequential addition of 1.5 mL water—5 mL 15% aqueous sodium hydroxide—5 mL water. The mixture was filtered through a plug of celite with tetrahydrofuran washing, and the filtrate was dried over anhydrous potassium carbonate, refiltered and evaporated to afford 4,5-bis(4-methoxyphenyl)-2-[5-[3-(1H-imidazol-1-yl)propyl]amino]pentylthio-1H-imidazole (4.18 g crude weight) as an oil. $^1$H NMR (CDCl$_3$): 7.67 (1H, s); 7.46 (4H, d, J=8.8 Hz); 6.99 (1H, s); 6.89 (1H, s); 6.84 (4H, d, J=8.8 Hz); 4.05 (2H, t, J=6.6 Hz); 3.81 (6H, s); 3.08 (2H, t, J=6.7 Hz); 2.56 (2H, t, J=6.0 Hz); 2.46 (2H, t, J=6.4 Hz); 1.90-1.40 (8H, m).

Part E. A solution of the amine from Part D above (7.85 mmol) in methylene chloride (50 mL) was cooled to 0° C., and treated with a solution of isopropyl isocyanate (2.00 mL, 20. 4 mmol) in methylene chloride (20 mL) dropwise with stirring. The solution was stirred overnight, then evaporated. The residual oil was separated by flash chromatography to afford the title product as a solid, m.p. 68°-69° C. (2.10 g, 3.55 mmol, 45%). $^1$H NMR (CDCl$_3$): 7.50 (1H, s); 7.46 (4H, d, J=8.6 Hz); 7.06 (1H, s); 6.93 (1H, s); 6.83 (4H, d, J=8.6 Hz); 4.17 (1H, d, J=7.3 Hz); 3.94 (2H, t, J=6.4 Hz); 3.90 (1H, octet, J=6.6 Hz); 3.80 (6H, s); 3.15 (2H, t, J=7.3 Hz); 3.06 (2H, t, J=7.0 Hz); 2.98 (2H, t, J=7.0 Hz); 2.02-1.30 (8H, m); 1.09 (6H, d, J=6.6 Hz). High-resolution mass spectrum: calculated for $C_{32}H_{43}N_6O_3S$ 591.3117, observed 591.3112, difference 0.8 ppm.

Compounds 131-200 in Table 3 can be prepared by the procedure described in Example 135 employing the appropriately substituted starting materials.

EXAMPLE 201

Preparation of
bis[2-(4,5-diphenyl-1H-imidazol-2-ylthio)ethyl]-ether

A solution of 4,5-diphenyl-2-mercapto-1H-imidazole (2.63 g, 10.44 mmol), chloroethyl ether (0.6 mL, 5.22 mmol), potassium carbonate (1.59 g, 11.5 mmol) and tetra-n-butylammonium iodide (0.39 g, 1.04 mmol) in tetrahydrofuran (20 mL) was heated to reflux for 14 hours. The solution was cooled, then poured into water (100 mL). This was extracted with methylene chloride (2×100 mL), and the extracts were combined, dried over anhydrous magnesium sulfate, filtered and evaporated. The residue was separated by flash chromatography (3:7 ethyl acetate-hexane, then 1:1 ethyl acetate-hexane) to afford the title product, which was further purified by recrystallization from acetonitrile, mp 232°-234° C. (1.00 g, 1.74 mmol, 33%). $^1$H NMR (CDCl$_3$): 11.70 (2H, br s); 7.60-7.16 (20H, m); 3.80 (4H, t, J=5.7 Hz); 3.21 (4H, t, J=5.7 Hz). Elemental analysis: calc. C 71.05, H 5.26, N 9.75; obs. C 70.84, H 5.17, N 9.68.

Compounds 201-240 in Table 4 can be prepared by the procedure described in Example 201 employing the appropriately substituted starting materials.

EXAMPLE 251

Preparation of
4,5-diphenyl-2-[5-[2-(2-pyridyl)ethoxy]pentyl]thio-1H-imidazole

Sodium hydride (2.24 g of 50% w/w slurry in mineral oil, 46.7 mmol) was washed in hexane and dried under vacuum. Dimethylsulfoxide (30 mL) was added, followed by a solution of 2-(2-hydroxyethyl)pyridine (5.00 mL, 44.4 mmol) in dimethylsulfoxide (20 mL) dropwise. After stirring for 2 hours, the mixture was treated with 1H-bromo-5-chloropentane (6.00 mL, 45.5 mmol), and was heated to 80° C. for 18 hours. The resulting mixture was cooled, treated with 4,5-diphenyl-2-mercapto-1H-imidazole (7.00 g, 27.7 mmol), potassium carbonate (7.00 g, 50.6 mmol) and sodium iodide (1 g), and heated again to 80° C. for an additional 24 hours. The mixture was cooled, poured into 400 mL ethyl acetate, and washed with water (4×400 mL). The ethyl acetate layer was washed with saturated aqueous sodium chloride (200 mL), dried over anhydrous magnesium sulfate, filtered and evaporated. The residue was separated by flash chromatography, and the product was further purified by preparative thin-layer chromatography to afford the title compound as an oil (940 mg, 2.12 mmol, 8%). $^1$H NMR (CDCl$_3$): 11.53 (1H, br s); 8.48 (1H, dt, J=5.1, 0.9 Hz); 7.61-7.06 (13H, m); 3.70 (2H, t, J=6.6 Hz); 3.37 (2H, t, J=6.0 Hz); 2.97 (2H, t, J=7.3 Hz); 2.94 (2H, t, J=6.6 Hz); 1.68-1.30 (6H, m). High-resolution mass spectrum: calculated for C$_{27}$H$_{30}$N$_3$OS 444.2110, observed 444.2101, difference 1.9 ppm.

Compounds 241-310 in Table 5 can be prepared by the procedure described in Example 251 employing the appropriately substituted starting materials.

EXAMPLE 317

Preparation of
4,5-bis(4-methoxyphenyl)-2-[2-[2-(2-methyl-1H-imidazol-1-yl)ethoxy]ethyl]thio-1H-imidazole Part A. A mineral oil suspension of sodium hydride (0.91 g, 50%, 37.8 mmol) was washed with hexane and dried under vacuum, then suspended in dimethylsulfoxide (20 mL). The mixture was cooled to 0° C., and a solution of 2-methyl-1H-benzimidazole (5.00 g, 37.8 mmol) was added dropwise with stirring. The mixture was stirred for 5 hours with warming to ambient temperature, then was treated dropwise with a solution of chloroethyl ether (8.90 mL, 75.6 mmol). Sodium iodide (2.83 g, 18.9 mmol) was added, and the mixture was heated to 90° C. for 18 hours. After being cooled to ambient temperature, the reaction mixture was poured into 400 mL ethyl acetate, and washed with water (3×400 mL). The aqueous phases were back-extracted in sequence with ethyl acetate (400 mL). The organic phases were combined, dried over anhydrous magnesium sulfate, filtered and evaporated. The residual oil was separated by flash chromatography to afford the product, 1-[2-(2-chloroethoxy)ethyl]-2-methyl-1H-benzimidazole, as a white solid, m.p. 96°-98° C. $^1$H NMR (CDCl$_3$): 7.74-7.64 (1H, m); 7.31-7.20 (3H, m); 4.31 (2H, t, J=5.4 Hz); 3.81 (2H, t, J=5.4 Hz); 3.59 (2H, t, J=5.1 Hz); 3.51 (2H, t, J=5.1 Hz); 2.64 (3H, s).

Part B. A mixture of the chloride from Part A above (2.50 g, 10.5 mmol), 4,5-bis(4-methoxyphenyl)-2-mercapto-1H-imidazole (3.27 g, 10.5 mmol), potassium carbonate (1.88 g, 13.6 mmol), and tetra-n-butylammonium iodide (0.77 g, 2.09 mmol) in tetrahydrofuran (20 mL) was heated to reflux for 24 hours. The mixture was cooled, and poured into water (150 mL). This was extracted with methylene chloride (2×150 mL), and the extracts were combined, dried over anhydrous magnesium sulfate, filtered, and evaporated. The residue was separated by flash chromatography (1:1 acetone-hexane) to afford the title product as a solid, m.p. 77°-79° C. (4.66 g, 9.05 mmol, 86%). $^1$H NMR (CDCl$_3$): 10.20 (1H, br s); 7.55-7.09 (8H, m); 6.95-6.78 (4H, br); 4.27 (2H, t, J=5.1 Hz); 3.81 (6H, s); 3.78 (2H, t, J=5.1 Hz); 3.52 (2H, t, J=5.7 Hz0; 3.06 (2H, t, J=5.7 Hz); 2.64 (3H, s).

Compounds 311-360 in Table 6 can be prepared by the procedure in Example 317 employing appropriately substituted starting materials.

EXAMPLE 366

Preparation of bis
[3-(4,5-diphenyl-1H-imidazol-2-ylthio)propyl]-sulfide

Part A. A solution of phosphorus tribromide (0.90 mL, 9.13 mmol) in benzene (20 mL) was cooled in an ice bath to 0° C. Pyridine (0.20 mL) was slowly added dropwise by syringe, and the solution was allowed to stir for 5 minutes. Then, a solution of 3,3'-thiodipropanol (1.96 g, 13.1 mmol) and pyridine (0.10 mL, total volume of pyridine 0.30 mL, 3.26 mmol) in benzene (20 mL) was added dropwise over a period of 30 minutes. The mixture was allowed to stir for 20 hours, with gradual warming to ambient temperature. At this point, the presence of unreacted, undissolved thiodipropanol was observed. The reaction was evaporated, and the residue was taken up in chloroform (40 mL) and treated with excess phosphorous tribromide (0.90 mL, 9.13 mmol). This mixture was stirred for an additional 18 hours, then poured into ice water. This mixture was allowed to melt and warm to ambient temperature, then was extracted with ethyl acetate 92×150 mL). The extracts were combined, dried over anhydrous potassium carbonate, filtered and evaporated. The residual oil was then separated by flash chromatography (2:3 ethyl acetate-hexane) to afford the product, bis(3-bromopropyl)sulfide, as a colorless oil (1.06 g, 3.84 mmol, 29%). $^1$H NMR (CDCl$_3$): 3.53 (4H, t, J=6.4 Hz); 2.69 (4H, t, J=6.9 Hz); 2.13 (4H, pentet, J=6.6 Hz).

Part B. A solution of the dibromide prepared in Part A above (1.06 g, 3.84 mmol) 4,5-diphenyl-2-mercapto-1H-imidazole (1.94 g, 7.68 mmol), potassium carbonate (1.17 g, 8.45 mmol) and tetra-n-butylammonium iodide (0.57 g, 1.54 mmol) in tetrahydrofuran (30 mL) was heated to mild reflux for 18 hours. The mixture was cooled, and poured into water (150 mL). This was extracted with methylene chloride (150 mL). The aqueous phase was neutralized to pH 7 with aqueous hydrochloric acid solution (6N), saturated with sodium chloride, and re-extracted with methylene chloride (150 mL). The extracts were combined, dried over anhydrous magnesium sulfate, filtered and evaporated. The resulting solid was collected by filtration and washed with methylene chloride, then dried under vacuum to afford the title product, m.p. 208°-209° C. $^1$H NMR (d$^6$ DMSO): 12.58 (2H, br s); 7.50-7.17 (20 H, m); 3.14 (4H, t, J=6.8 Hz); 2.64 (4H, t, J=6.8 Hz); 1.92 (4H, pentet, J=6.8 Hz). Elemental analysis: calc. C 69.87, H 5.54, N 9.05; obs. C 69.13, H 5.49, N 8.72.

Compounds 361-400 in Table 7 can be prepared by the procedure described in Example 366 employing the appropriately substituted starting materials.

EXAMPLE 411

Preparation of
4,5-diphenyl-2-[5-(2-pyridylmethyl)thio]pentylthio-1H-imidazole

Part A. A suspension of 4,5-diphenyl-2-mercapto-1H-imidazole (5.75 g, 22.8 mmol), 1-bromo-5-chloropentane (3.00 mL, 22.8 mmol), potassium carbonate (3.78 g, 27.3 mmol) and tetra-n-butylammonium iodide (1.50 g) in tetrahydrofuran (50 mL) was heated to reflux for 20 hours. The reaction mixture was cooled, and treated with thiolacetic acid (2.00 mL, 28.0 mmol) and potassium carbonate (3.78 g, 27.3 mmol). The reaction mixture was then heated for an additional 20 hours, then cooled and poured into water (200 mL). This was extracted with methylene chloride (2×200 mL), and the extracts were combined, dried over anhydrous potassium carbonate, filtered and evaporated. The residual oil was separated by flash chromatography (1:4 ethyl acetate-hexane) to afford 4,5-diphenyl-2-(5-thiolacetyl)-pentylthio-1H-imidazole as an oil (1.80 g, 4.54 mmol). $^1$H NMR (CDCl$_3$): 9.66 (1H, br s); 7.60–7.20 (10H, m); 3.07 (2H, t, J=7.1 Hz); 2.86 (2H, t, J=7.1 Hz); 2.30 (3H, s); 1.79–1.42 (6H, m).

Part B. The thiolester compound prepared in Part A above (1.80 g, 4.54 mmol) was dissolved in absolute, degassed ethanol, and treated with aqueous sodium hydroxide solution (0.80 g of 50%, 10.0 mmol). The solution was stirred for 48 hours, then evaporated. The residue was partitioned between water and methylene chloride (200 mL each). The aqueous phase was extracted with an additional portion of methylene chloride, and the organic phases were combined, dried over anhydrous magnesium sulfate, filtered and evaporated. The slightly impure residue was used directly in the next step.

The residue from above (est. 3 mmol), 2-picolyl chloride hydro-chloride (1.37 g, 8.35 mmol) and potassium carbonate (2.81 g, 20.3 mmol) were dissolved in 1:1 tetrahydrofuran-dimethylformamide (20 mL). This mixture was heated to 70° C. for 20 hours, then cooled and poured into water (200 mL). This mixture was extracted with methylene chloride (2×200 mL), and the organic extracts were combined, dried over anhydrous magnesium sulfate, filtered and evaporated. Residual dimethylformamide was removed by short-path distillation under vacuum, and the remaining residue was separated by flash chromatography (1:1 ethyl acetate-hexane) to afford the title compound as an oil (710 mg, 1.59 mmol, 53%). $^1$NMR (CDCl$_3$): 10.16 (1H, br s); 8.46 (1H, dd, J=5.1, 0.7 Hz); 7.70–7.58 (3H, m); 7.40–7.10 (10H, m); 3.77 (2H, s); 3.07 (2H, t, J=7.0 Hz); 2.46 (2H, t, J=7.3 Hz); 1.77–1.48 (6H, m). High-resolution mass spectrum: for C$_{26}$H$_{28}$N$_3$S$_2$ calculated 446.1725, observed 446.1710, difference 3.3 ppm.

Compounds 401–470 in Table 8 can be prepared by the procedure described in Example 411 employing the appropriately substituted starting materials.

EXAMPLE 476

Preparation of
4,5-diphenyl-2-[3-[3-(2-methyl-1H-benzimidazol-1-yl)propylthio]propylthio]-1H-imidazole Part A. Sodium hydride (0.11 g of 50% mineral oil suspension, 4.64 mmol) was washed with hexane, and dried under vacuum, then suspended in dimethylsulfoxide and cooled to 0° C. A solution of 2-methyl-1H-benzimidazole (0.61 g, 4.64 mmol) in dimethylsulfoxide (5 mL) was added dropwise. The ice bath was removed, and the mixture was allowed to stir for 5 hours. A solution of bis(3-bromopropyl)sulfide (Example 366, Part A; 2.56 g, 9.27 mmol) in dimethylsulfoxide (5 mL), along with sodium iodide (0.35 g, 2.32 mmol), were added, and the resulting mixture was heated to 80° C. for 20 hours. It was then cooled to ambient temperature, and poured into 100 mL ethyl acetate. This was washed with water (4×100 mL), and the aqueous phases were back-extracted in sequence with ethyl acetate (100 mL). The organic phases were combined, dried over anhydrous magnesium sulfate, filtered and evaporated. The residue was separated by flash chromatography (1:1 ethyl acetate-hexane, then ethyl acetate, then acetone) to afford 1-[3-(3-bromopropyl)thiopropyl]-2-methyl-1H-benzimidazole as an oil (0.21 g, 0.64 mmol). $^1$NMR (CDCl$_3$): 7.74–7.23 (4H, m); 4.28 (2H, t, J=6 Hz); 3.52 (2H, t, J=6 Hz); 2.70 (2H, t, J=7 Hz); 2.66 (3H, s); 2.55 (2H, t, J=7 Hz); 2.19–2.02 (4H, m).

Part B. A solution of the bromide prepared in Part A above (0.21 g, 0.64 mmol), 4,5-diphenyl-2-mercapto-1H-imidazole (0.17 g, 0.64 mmol), potassium carbonate (0.12 g, 0.83 mmol) and tetra-n-butylammonium iodide (0.05 g) in tetrahydrofuran (10 mL) was heated to mild reflux for 20 hours, then cooled and poured into water (150 mL). This was extracted with methylene chloride (2×150 mL), and the extracts were combined, dried over anhydrous magnesium sulfate, filtered and evaporated. The residue was separated by flash chromatography (ethyl acetate) to afford the title product, slightly impure. This compound, an oil, was further purified by preparative thin-layer chromatography. $^1$H NMR (CDCl$_3$): 7.61–7.45 (5H, m); 7.34–7.18 (9H, m); 4.16 (2H, t, J=7.0 Hz); 3.12 (2H, t, J=7.0 Hz); 2.59 (2H, t, J=7.0 Hz); 2.54 (3H, s); 2.44 (2H, t, J=6.8 Hz); 2.03 (2H, pentet, J=7.0 Hz); 1.93 (2H, pentet, J=7.1 Hz). High-resolution n mass spectrum: for C$_{29}$H$_{31}$N$_4$S$_2$ calculated 499.1990, observed 499.1993, difference 0.6 ppm.

Compound Example Numbers 471–520 in Table 9 can be prepared by the procedure described in Example 471 employing the appropriately substituted starting materials.

Utility

The compounds of the invention are effective antiatherosclerotic agents that may act in a variety of ways. The compounds may act as inhibitors of the enzyme acyl CoA:cholesterol acyl transferase (ACAT). Inhibition of ACAT has a variety of antiatherosclerotic effects, including inhibiting esterification and transport of cholesterol across the intestinal wall. In addition, by inhibiting cholesterol ester formation, the compounds may be useful in preventing the formation of cholesterol ester rich macrophages (foam cells) in the arterial wall. Foam cells are a source of the large quantity of cholesterol ester found in atheromatous lesions, as compared to the surrounding undiseased tissue. Other compounds of the invention may act as inhibitors of cholesterol biosynthesis in the liver. Some compounds of the invention may act as both ACAT inhibitors and inhibitors of cholesterol biosynthesis.

The antiatherosclerotic and antihypercholesterolemic activity of the compounds of the present invention may be determined using the assays described below.

A. Assay of the Inhibition of Acyl-CoA: Cholesterol Acyltransferase (ACAT) in Hepatic Microsomes The ability of the compounds to inhibit ACAT, the enzyme responsible for the intracellular synthesis of cholesteryl esters, was tested as follows. Male Sprague Dawley rats weighing 150–300 g, were fed rat chow ad libitum. The animals were fasted for twenty-four hours prior to being sacrificed by decapitation. The livers were perfused in situ with 50 ml of cold 0.25 sucrose, excised, and homogenized in three volumes of 0.1M phosphate buffer, pH 7.4, that contained 0.5 mM EDTA (ethylenediamine-tetraacetic acid), 1.0 mM glutathione, 0.25M sucrose and 20mM leupeptin. Microsomes were obtained by differential centrifugation; the supernatant from an initial spin at 15,000×g for 15 minutes was centrifuged at 105,000×g for 1 hour to pellet the microsomes. The microsomes were suspended in homogenization buffer, reisolated by centrifugation, and stored at $-70°$ C. Microsomes were used within one month of preparation.

The control assay in a final volume of 200 µl consisted of 200 µg of microsomal protein, 75 µM $^{14}$C-oleoyl-CoA (10,000 dpm/nmol) in 0.1M phosphate, pH 7.4, that contained 1 mM glutathione. Compounds were added in 5 µl of DMSO (dimethyl sulfoxide) and additional controls were run with DMSO only. All components, except the oleoyl-CoA, were preincubated for 15 min. at 37° C. prior to the initiation of the reaction by the addition of oleoyl-CoA. The assay was terminated after 10 min by the addition of 4 ml of chloroform:methanol (2:1, v/v). 20,000 dpm of $^3$H-cholesteryl oleate and 10 µg of unlabeled cholesteryl oleate and oleic acid were added as an internal standard and carriers, respectively. After allowing 10 min. for lipid extraction, the samples were centrifuged at 1,000×g for 10 min. to separate the solvent layers. The chloroform layer containing the neutral lipids was spotted onto a Baker SI250-Pa silica gel TLC plate and the plate developed using a hexane:diethyl ether:acetic acid (170:30:1) v/v/v) mobile phase. The lipids were visualized by their interaction with iodine vapor and the cholesteryl ester spot was scraped into a scintillation vial and counted. The specific activity of ACAT in the control incubation averaged 260 pmol/min/mg microsomal protein. The data obtained are expressed as the concentration at which ACAT activity is inhibited by 50% ($IC_{50}$).

B. Assay of the Inhibition of Cholestrol Esterification in Mammalian Cells

The esterification of cholesterol was determined in the murine macrophage-like cell line J774.Al. Cells were seeded in 35 mm wells at a density of 300,000 cells per well in 2 mls of Dulbecco's Eagle Medium (DMEM) supplemented with 10% fetal bovine serum (FBS). Cells were incubated at 37° C. in an atmosphere of 5% $CO_2$ and 93% humidity. After 24 hours the media was changed to 0.68 mls 10% FBS-DMEM containing 34 µg of acetylated human low density lipoprotein (ac-LDL) to increase the intracellular concentration of cholesterol and promote esterification. At 41 hours, various inhibitors were added to the cells in DMSO (10 µ/ml maximum). At 43 hours, the cells were pulsed with 0.1 mM $^{14}$C-oleic acid (10,000 dpm/nmol) complexed with BSA (bovine serum albumin) to follow cholesterol ester formation. The experiment was terminated at 45 hours by washing the monolayers 3 times with 3 ml of Tris-buffered saline at 4° C. The lipids were extracted by incubating the monolayers with 1.5 ml of hexane:isopropanol (3:2, v/v) for 30 min. under gentle agitation. During this period, 10,000 dpm $^3$H-cholesteryl linoleate and 10 µg of cholesteryl oleate were added as an internal standard and carrier respectively. The organic solvent was removed and the cells were washed with an additional 1.0 ml of hexane:isopropanol which was combined with the original extract. The cells were allowed to dry overnight, digested with 1.5 ml of 0.2N sodium hydroxide for 1 hour and an aliquot of the solubilized protein used for protein determination using the Lowry method. The organic extract was taken to dryness, the residue resuspended in 100 µl of chloroform and the lipids separated on silica gel impregnated glass fiber plates using a hexane:diethylether:acetic acid (170:30:1, v/v/v) solvent system. Individual lipids were visualized with iodine and the cholesteryl ester spot cut out and transferred to scintillation vials to determine the amount of radioactivity. The conversion of oleic acid to cholesteryl ester in the control averaged 0.54 mmol/hour/mg protein and was increased upon the addition of ac-LDL to about 10.69±0.69 mmol/hour/mg protein. The data obtained are expressed as the concentration at which ACAT activity is inhibited by 50% ($IC_{50}$).

C. Assay of Antihypercholesterolemic Activity in Cholesterol-Fed Hamsters

Inhibiton of ACAT activity in the gut reduces the absorption of cholesterol in cholesterol-fed animals. Hamsters weighing approximately 100 g, were maintained on a diet supplemented with 0.8% cholesterol. The treatment group received 1–100 mg/kg/day, p.o., of the test compound dissolved in 500 µl of corn oil for a period of two weeks. The control group were pair-fed to the treatment group and were dosed with 500 µl of the corn oil vehicle. At sacrifice, the hamsters were anesthetized with $CO_2$ and exsanguinated via cardiac puncture. Total serum cholesterol was determined on a DuPont aca ® IV. The data obtained are expressed in terms of mg cholesterol per 100 ml of serum (mg %).

Using the assay methods described above, the compounds of this invention are found to exhibit an activity of about $IC_{50}<50$ micromolar, thereby demonstrating and confirming the activity of these compound as effective antihypercholesterolemic and/or antiatherosclerotic agents.

DOSAGE AND FORMULATION

The compounds of the present invention can be administered orally using any pharmaceutically acceptable dosage form known in the art for such administration. The active ingredient can be supplied in solid dosage forms such as dry powders, granules, tablets or capsules, or in liquid dosage forms, such as syrups or aqueous suspensions. The active ingredient can be administered alone, but is generally administered with a pharmaceutical carrier. A valuable treatise with respect to pharmaceutical dosage forms is *Remington's Pharmaceutical Sciences,* Mack Publishing.

In their therapeutic use as antihypercholesterolemic and/or anti- atherosclerotic agents, the compounds of the invention are administered to the patient at dosage levels of 1 to 28 g per day. For a normal male adult human of approximately 70 kg of body weight, this translates into a dosage of 14 to 400 mg per kilogram body weight per day. The dosage administered will, of course, vary depending upon known factors such as the age, health, and weight of the recipient; nature and extent of symptoms, kind of concurrent treatment, frequency of treatment, and the effect desired. Useful pharmaceutical dosage forms for administration of the compounds of this invention can be illustrated as follows:

Tablets: Tablets may be prepared by conventional procedures so that the dosage unit is 500 milligrams of active ingredient, 150 milligrams of lactose, 50 milligrams of cellulose and 10 milligrams of magnesium stearate.

Capsules: Capsules are prepared by conventional procedures so that the dosage unit is 500 milligrams of active ingredient, 100 milligrams of cellulose and 10 milligrams of magnesium stearate.

Syrup:

|  | Wt. % |
| --- | --- |
| Active Ingredient | 10 |
| Liquid Sugar | 50 |
| Sorbitol | 20 |
| Glycerine | 5 |
| Flavor, Colorant and Preservative | as required |
| Water | as required |

The final volume is brought up to 100% by the addition of distilled water.

Aqueous Suspension:

|  | Wt. % |
| --- | --- |
| Active Ingredient | 10 |
| Sodium Saccharin | 0.01 |
| Keltrol ® (Food Grade Xanthan Gum) | 0.2 |
| Liquid Sugar | 5 |
| Flavor, Colorant and Preservative | as required |
| Water | as required |

Xanthan gum is slowly added into distilled water before adding the active ingredient and the rest of the formulation ingredients. The final suspension is passed through a homogenizer to assure the elegance of the final products.

Resuspendable Powder:

|  | Wt. % |
| --- | --- |
| Active Ingredient | 50.0 |
| Lactose | 35.0 |
| Sugar | 10.0 |
| Acacia | 4.7 |
| Sodium Carboxylmethylcellulose | 0.3 |

Each ingredient is finely pulverized and then uniformly mixed together. Alternatively, the powder can be prepared as a suspension and then spray dried.

Sem-Solid Gel:

|  | Wt. % |
| --- | --- |
| Active Ingredient | 10 |
| Sodium Saccharin | 0.02 |
| Gelatin | 2 |
| Flavor, Colorant and Preservative | as required |
| Water | as required |

Gelatin is prepared in hot water. The finely pulverized active ingredient is suspended in the gelatin solution and then the rest of the ingredients are mixed in. The suspension is filled into a suitable packaging container and cooled down to form the gel.

Sem-Solid Paste:

|  | Wt. % |
| --- | --- |
| Active Ingredient | 10 |
| Gelcarin ® (Carrageenin gum) | 1 |
| Sodium Saccharin | 0.01 |
| Gelatin | 2 |
| Flavor, Colorant and Preservative | as required |
| Water | as required |

Gelcarin ® is dissolved in hot water (around 80° C.) and then the fine-powder active ingredient is suspended in this solution. Sodium saccharin and the rest of the formulation ingredients are added to the suspension while it is still warm. The suspension is homogenized and then filled into suitable containers.

Emulsifiable Paste:

|  | Wt. % |
| --- | --- |
| Active Ingredient | 30 |
| Tween ® 80 and Span ® 80 | 6 |
| Keltrol ® | 0.5 |
| Mineral Oil | 63.5 |

All the ingredients are carefully mixed together to make a homogenous paste.

The term "consisting essentially of" in the present disclosure is intended to have its customary meaning; namely, that all specified materials and conditions are very important in practicing the invention but that unspecified materials and conditions are not excluded so long as they do not prevent the benefits of the invention from being realized.

The foregoing disclosure includes all the information deemed essential to enable those of skill in the art to practice the claimed invention. Because the cited references may provide further useful information, however, these cited materials are hereby incorporated by reference.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

TABLE 1

$$R^1\text{-}C(=N)\text{-}C(R^2)(NR^3)\text{-}X\text{-}(CH_2)_m\text{-}N\text{-}(CH_2)_n\text{-}A\text{-}C(=N)\text{-}C(R^6)=C(R^7)\text{-}B$$
(with Y=Z substituent on middle N)

| Ex. No. | R¹ | R² | R³ | X | m | n | Y | Z | A | B | R⁶ | R⁷ | m.p. |
|---|---|---|---|---|---|---|---|---|---|---|---|---|---|
| 1 | Ph | Ph | H | S | 5 | 5 | O | NH-2,4-C₆H₄F₂ | S | NH | Ph | Ph | — |
| 2 | Ph | Ph | H | S | 5 | 5 | O | NH-iPr | S | NH | Ph | Ph | — |
| 3 | Ph | Ph | H | S | 5 | 5 | O | CH₂-cC₆H₁₁ | S | NH | Ph | Ph | — |
| 4 | Ph | Ph | H | S | 5 | 5 | O | OCH₂Ph | S | NH | Ph | Ph | 86–88 |
| 5 | Ph | Ph | H | S | 5 | 5 | O | NH-2,4-C₆H₄F₂ | S | NH | 4-CH₃O—C₆H₄ | 4-CH₃O—C₆H₄ | — |
| 6 | Ph | Ph | H | S | 5 | 5 | O | NH-iPr | S | NH | 4-CH₃O—C₆H₄ | 4-CH₃O—C₆H₄ | — |
| 7 | Ph | Ph | H | S | 5 | 5 | O | CH₂-cC₆H₁₁ | S | NH | 4-CH₃O—C₆H₄ | 4-CH₃O—C₆H₄ | — |
| 8 | Ph | Ph | H | S | 5 | 5 | O | OCH₂Ph | S | NH | 4-CH₃O—C₆H₄ | 4-CH₃O—C₆H₄ | 96–98 |
| 9 | Ph | Ph | H | S | 5 | 5 | O | NH-2,4-C₆H₄F₂ | S | NH | 4-(CH₃)₂N—C₆H₄ | 4-(CH₃)₂N—C₆H₄ | 117–119 |
| 10 | Ph | Ph | H | S | 5 | 5 | O | NH-iPr | S | NH | 4-(CH₃)₂N—C₆H₄ | 4-(CH₃)₂N—C₆H₄ | — |
| 11 | Ph | Ph | H | S | 5 | 5 | O | CH₂-cC₆H₁₁ | S | NH | 4-(CH₃)₂N—C₆H₄ | 4-(CH₃)₂N—C₆H₄ | — |
| 12 | Ph | Ph | H | S | 5 | 5 | O | OCH₂Ph | S | NH | 4-(CH₃)₂N—C₆H₄ | 4-(CH₃)₂N—C₆H₄ | 97–99 |
| 13 | 4-CH₃O—C₆H₄ | 4-CH₃O—C₆H₄ | H | S | 5 | 5 | O | NH-2,4-C₆H₄F₂ | S | NH | 4-CH₃O—C₆H₄ | 4-CH₃O—C₆H₄ | — |
| 14 | 4-CH₃O—C₆H₄ | 4-CH₃O—C₆H₄ | H | S | 5 | 5 | O | NH-iPr | S | NH | 4-CH₃O—C₆H₄ | 4-CH₃O—C₆H₄ | — |
| 15 | 4-CH₃O—C₆H₄ | 4-CH₃O—C₆H₄ | H | S | 5 | 5 | O | CH₂-cC₆H₁₁ | S | NH | 4-CH₃O—C₆H₄ | 4-CH₃O—C₆H₄ | — |
| 16 | 4-CH₃O—C₆H₄ | 4-CH₃O—C₆H₄ | H | S | 5 | 5 | O | OCH₂Ph | S | NH | 4-CH₃O—C₆H₄ | 4-CH₃O—C₆H₄ | — |
| 17 | Ph | Ph | H | S | 5 | 5 | O | NH-2,4-C₆H₄F₂ | S | NH | —(C₄H₄)— | —(C₄H₄)— | — |
| 18 | Ph | Ph | H | S | 5 | 5 | O | NH-iPr | S | NH | —(C₄H₄)— | —(C₄H₄)— | — |
| 19 | Ph | Ph | H | S | 5 | 5 | O | CH₂-cC₆H₁₁ | S | NH | —(C₄H₄)— | —(C₄H₄)— | — |
| 20 | Ph | Ph | H | S | 5 | 5 | O | OCH₂Ph | S | NH | —(C₄H₄)— | —(C₄H₄)— | — |
| 21 | Ph | Ph | H | S | 5 | 5 | O | Ph | S | NH | —(C₄H₄)— | —(C₄H₄)— | 75–77 |
| 22 | 4-CH₃O—C₆H₄ | 4-CH₃O—C₆H₄ | H | S | 5 | 5 | O | NH-2,4-C₆H₄F₂ | S | NH | —(C₄H₄)— | —(C₄H₄)— | — |
| 23 | 4-CH₃O—C₆H₄ | 4-CH₃O—C₆H₄ | H | S | 5 | 5 | O | NH-iPr | S | NH | —(C₄H₄)— | —(C₄H₄)— | — |
| 24 | 4-CH₃O—C₆H₄ | 4-CH₃O—C₆H₄ | H | S | 5 | 5 | O | CH₂-cC₆H₁₁ | S | NH | —(C₄H₄)— | —(C₄H₄)— | — |
| 25 | 4-CH₃O—C₆H₄ | 4-CH₃O—C₆H₄ | H | S | 5 | 5 | O | OCH₂Ph | S | NH | —(C₄H₄)— | —(C₄H₄)— | — |
| 26 | 4-CH₃O—C₆H₄ | 4-CH₃O—C₆H₄ | H | S | 5 | 5 | O | Ph | S | NH | —(C₄H₄)— | —(C₄H₄)— | — |
| 27 | Ph | Ph | H | S | 5 | 5 | O | NH-2,4-C₆H₄F₂ | NH | O | —(C₄H₄)— | —(C₄H₄)— | — |
| 28 | Ph | Ph | H | S | 5 | 5 | O | NH-iPr | NH | O | —(C₄H₄)— | —(C₄H₄)— | — |
| 29 | Ph | Ph | H | S | 5 | 5 | O | CH₂-cC₆H₁₁ | NH | O | —(C₄H₄)— | —(C₄H₄)— | — |
| 30 | Ph | Ph | H | S | 5 | 5 | O | OCH₂Ph | NH | O | —(C₄H₄)— | —(C₄H₄)— | — |
| 31 | Ph | Ph | H | S | 5 | 5 | O | Ph | NH | O | —(C₄H₄)— | —(C₄H₄)— | — |
| 32 | Ph | Ph | H | S | 5 | 5 | O | NH-2,4-C₆H₄F₂ | S | S | —(C₄H₄)— | —(C₄H₄)— | — |
| 33 | Ph | Ph | H | S | 5 | 5 | O | NH-iPr | S | S | —(C₄H₄)— | —(C₄H₄)— | — |
| 34 | Ph | Ph | H | S | 5 | 5 | O | CH₂-cC₆H₁₁ | S | S | —(C₄H₄)— | —(C₄H₄)— | — |
| 35 | Ph | Ph | H | S | 5 | 5 | O | OCH₂Ph | S | S | —(C₄H₄)— | —(C₄H₄)— | — |
| 36 | Ph | Ph | H | S | 5 | 5 | O | Ph | S | S | —(C₄H₄)— | —(C₄H₄)— | — |
| 37 | Ph | Ph | H | S | 5 | 5 | O | NH-2,4-C₆H₄F₂ | S | O | —(C₄H₄)— | —(C₄H₄)— | — |
| 38 | Ph | Ph | H | S | 5 | 5 | O | NH-iPr | S | O | —(C₄H₄)— | —(C₄H₄)— | — |
| 39 | Ph | Ph | H | S | 5 | 5 | O | CH₂-cC₆H₁₁ | S | O | —(C₄H₄)— | —(C₄H₄)— | — |
| 40 | Ph | Ph | H | S | 5 | 5 | O | OCH₂Ph | S | O | —(C₄H₄)— | —(C₄H₄)— | — |
| 41 | Ph | Ph | H | S | 5 | 5 | O | Ph | S | O | —(C₄H₄)— | —(C₄H₄)— | — |
| 42 | Ph | Ph | H | S | 8 | 3 | O | NH-2,4-C₆H₄F₂ | S | O | —(C₄H₄)— | —(C₄H₄)— | — |
| 43 | Ph | Ph | H | S | 8 | 3 | O | NH-iPr | S | O | —(C₄H₄)— | —(C₄H₄)— | — |

TABLE 1-continued

| Ex. No. | R¹ | R² | R³ | X | m | n | Y | Z | A | B | R⁶ | R⁷ | m.p. |
|---|---|---|---|---|---|---|---|---|---|---|---|---|---|
| 44 | Ph | Ph | H | S | 8 | 3 | O | $CH_2$-$cC_6H_{11}$ | S | O | | | — |
| 45 | Ph | Ph | H | S | 8 | 3 | O | $OCH_2Ph$ | S | O | | | — |
| 46 | Ph | Ph | H | S | 8 | 3 | O | Ph | S | O | | | — |
| 47 | Ph | Ph | H | S | 5 | 5 | O | NH-2,4-$C_6H_4F_2$ | S | NH | iPr | iPr | — |
| 48 | Ph | Ph | H | S | 5 | 5 | O | NH-iPr | S | NH | iPr | iPr | — |
| 49 | Ph | Ph | H | S | 5 | 5 | O | $CH_2$-$cC_6H_{11}$ | S | NH | iPr | iPr | — |
| 50 | Ph | Ph | H | S | 5 | 5 | O | $OCH_2Ph$ | S | NH | iPr | iPr | — |
| 51 | Ph | Ph | Me | $SO_2$ | 5 | 5 | O | NH-2,4-$C_6H_4F_2$ | $SO_2$ | NH | Ph | Ph | — |
| 52 | Ph | Ph | H | S | 5 | 5 | O | NH-2,4-$C_6H_4F_2$ | S | N—Me | Ph | Ph | — |
| 53 | Ph | Ph | H | S | 5 | 5 | O | NH-2,4-$C_6H_4F_2$ | S | N | Ph | Ph | — |
| 54 | Ph | Ph | H | S | 2 | 5 | $H_2$ | Ph | S | NH | | | — |
| 55 | Ph | Ph | H | S | 5 | 5 | O | Ph | S | NH | | —($C_4H_4$)— | — |
| 56 | Ph | Ph | H | S | 5 | 5 | O | NH-iPr | S | NH | | —($C_4H_4$)— | — |
| 57 | Ph | Ph | H | S | 5 | 5 | O | NH-iPr | S | NH | 4-$CH_3S$-$C_6H_4$ | 4-$CH_3S$-$C_6H_4$ | — |
| 58 | Ph | Ph | H | S | 5 | 5 | O | NH-iPr | S | NH | $cC_6H_{11}$ | Ph | — |
| 59 | Ph | Ph | H | S | 5 | 5 | O | NH-iPr | S | NH | 4-$CH_3S$-$C_6H_4$ | iPr | — |
| 60 | Ph | Ph | H | S | 5 | 5 | O | NH-iPr | S | NH | 4-$CH_3S$-$C_6H_4$ | Ph | — |
| 61 | Ph | iPr | H | S | 5 | 5 | O | NH-iPr | S | NH | iPr | iPr | — |
| 62 | Ph | Ph | Ph | S | 5 | 5 | O | NH-4-Cl-$C_6H_4$ | S | NH | iPr | iPr | — |
| 63 | Ph | Ph | H | S | 5 | 5 | O | NH-iPr | S | N—Ph | Ph | Ph | — |
| 64 | Ph | Ph | H | S | 5 | 5 | O | NH-2,4-$C_6H_4F_2$ | S | NH | Ph | Ph | — |
| 65 | Ph | Ph | H | S | 5 | 5 | O | NH-iPr | S | NH | —(N=CH—N=CH)— | | — |
| 66 | Ph | Ph | H | S | 5 | 5 | O | $CH_2$-$cC_6H_{11}$ | S | NH | —(N=CH—N=CH)— | | — |
| 67 | Ph | Ph | H | S | 5 | 5 | O | $OCH_2Ph$ | S | NH | —(N=CH—N=CH)— | | — |
| 68 | Ph | Ph | H | S | 5 | 5 | O | NH-2,4-$C_6H_4F_2$ | S | NH | —(N=CH—CH=CH)— | | — |
| 69 | Ph | Ph | H | S | 5 | 5 | O | NH-iPr | S | NH | —(N=CH—CH=CH)— | | — |
| 70 | Ph | Ph | H | S | 5 | 5 | O | $CH_2$-$cC_6H_{11}$ | S | NH | —(N=CH—CH=CH)— | | — |

TABLE 2

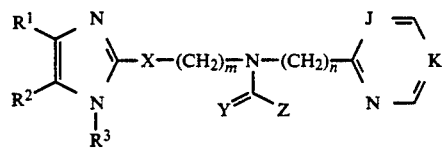

| Ex. No. | $R^1$ | $R^2$ | $R^3$ | X | m | n | Y | Z | J | K | m.p. |
|---|---|---|---|---|---|---|---|---|---|---|---|
| 71 | Ph | Ph | H | S | 5 | 1 | O | NH-2,4-$C_6H_3F_2$ | CH | CH | — |
| 72 | Ph | Ph | H | S | 5 | 1 | O | NH-iPr | CH | CH | — |
| 73 | Ph | Ph | H | S | 5 | 1 | O | $CH_2$-c$C_6H_{11}$ | CH | CH | — |
| 74 | Ph | Ph | H | S | 5 | 1 | O | $OCH_2C_6H_5$ | CH | CH | — |
| 75 | 4-MeO—$C_6H_4$ | 4-MeO—$C_6H_4$ | H | S | 5 | 1 | O | NH-2,4-$C_6H_3F_2$ | CH | CH | oil[a] |
| 76 | 4-MeO—$C_6H_4$ | 4-MeO—$C_6H_4$ | H | S | 5 | 1 | O | NH-iPr | CH | CH | oil[b] |
| 77 | 4-MeO—$C_6H_4$ | 4-MeO—$C_6H_4$ | H | S | 5 | 1 | O | $CH_2$-c$C_6H_{11}$ | CH | CH | — |
| 78 | 4-MeO—$C_6H_4$ | 4-MeO—$C_6H_4$ | H | S | 5 | 1 | O | $OCH_2C_6H_5$ | CH | CH | — |
| 79 | 4-$Me_2$N—$C_6H_4$ | 4-$Me_2$N—$C_6H_4$ | H | S | 5 | 1 | O | NH-2,4-$C_6H_3F_2$ | CH | CH | — |
| 80 | 4-$Me_2$N—$C_6H_4$ | 4-$Me_2$N—$C_6H_4$ | H | S | 5 | 1 | O | NH-iPr | CH | CH | — |
| 81 | 4-$Me_2$N—$C_6H_4$ | 4-$Me_2$N—$C_6H_4$ | H | S | 5 | 1 | O | $CH_2$-c$C_6H_{11}$ | CH | CH | — |
| 82 | 4-$Me_2$N—$C_6H_4$ | 4-$Me_2$N—$C_6H_4$ | H | S | 5 | 1 | O | $OCH_2C_6H_5$ | CH | CH | — |
| 83 | Ph | Ph | H | S | 5 | 2 | O | NH-2,4-$C_6H_3F_2$ | CH | CH | oil[c] |
| 84 | Ph | Ph | H | S | 5 | 2 | O | NH-iPr | CH | CH | oil[d] |
| 85 | Ph | Ph | H | S | 5 | 2 | O | $CH_2$-c$C_6H_{11}$ | CH | CH | — |
| 86 | Ph | Ph | H | S | 5 | 2 | O | $OCH_2C_6H_5$ | CH | CH | — |
| 87 | 4-MeO—$C_6H_4$ | 4-MeO—$C_6H_4$ | H | S | 5 | 2 | O | NH-2,4-$C_6H_3F_2$ | CH | CH | oil[e] |
| 88 | 4-MeO—$C_6H_4$ | 4-MeO—$C_6H_4$ | H | S | 5 | 2 | O | NH-iPr | CH | CH | oil[f] |
| 89 | 4-MeO—$C_6H_4$ | 4-MeO—$C_6H_4$ | H | S | 5 | 2 | O | $CH_2$-c$C_6H_{11}$ | CH | CH | — |
| 90 | 4-MeO—$C_6H_4$ | 4-MeO—$C_6H_4$ | H | S | 5 | 2 | O | $OCH_2C_6H_5$ | CH | CH | — |
| 91 | 4-$Me_2$N—$C_6H_4$ | 4-$Me_2$N—$C_6H_4$ | H | S | 5 | 2 | O | NH-2,4-$C_6H_3F_2$ | CH | CH | — |
| 92 | 4-$Me_2$N—$C_6H_4$ | 4-$Me_2$N—$C_6H_4$ | H | S | 5 | 2 | O | NH-iPr | CH | CH | — |
| 93 | 4-$Me_2$N—$C_6H_4$ | 4-$Me_2$N—$C_6H_4$ | H | S | 5 | 2 | O | $CH_2$-c$C_6H_{11}$ | CH | CH | — |
| 94 | 4-$Me_2$N—$C_6H_4$ | 4-$Me_2$N—$C_6H_4$ | H | S | 5 | 2 | O | $OCH_2C_6H_5$ | CH | CH | — |
| 95 | Ph | Ph | H | S | 5 | 0 | O | NH-2,4-$C_6H_3F_2$ | CH | CH | oil[g] |
| 96 | Ph | Ph | H | S | 5 | 0 | O | NH-iPr | CH | CH | oil[h] |
| 97 | 4-MeO—$C_6H_4$ | 4-MeO—$C_6H_4$ | H | S | 5 | 0 | O | NH-2,4-$C_6H_3F_2$ | CH | CH | — |
| 98 | 4-MeO—$C_6H_4$ | 4-MeO—$C_6H_4$ | H | S | 5 | 0 | O | NH-iPr | CH | CH | — |
| 99 | 4-$Me_2$N—$C_6H_4$ | 4-$Me_2$N—$C_6H_4$ | H | S | 5 | 0 | O | NH-2,4-$C_6H_3F_2$ | CH | CH | — |
| 100 | 4-$Me_2$N—$C_6H_4$ | 4-$Me_2$N—$C_6H_4$ | H | S | 5 | 0 | O | NH-iPr | CH | CH | — |
| 101 | Ph | Ph | H | S | 5 | 3 | O | NH-2,4-$C_6H_3F_2$ | CH | CH | — |
| 102 | Ph | Ph | H | S | 5 | 3 | O | NH-iPr | CH | CH | — |
| 103 | 4-MeO—$C_6H_4$ | 4-MeO—$C_6H_4$ | H | S | 5 | 3 | O | NH-2,4-$C_6H_3F_2$ | CH | CH | — |
| 104 | 4-MeO—$C_6H_4$ | 4-MeO—$C_6H_4$ | H | S | 5 | 3 | O | NH-iPr | CH | CH | — |
| 105 | 4-$Me_2$N—$C_6H_4$ | 4-$Me_2$N—$C_6H_4$ | H | S | 5 | 3 | O | NH-2,4-$C_6H_3F_2$ | CH | CH | — |
| 106 | 4-$Me_2$N—$C_6H_4$ | 4-$Me_2$N—$C_6H_4$ | H | S | 5 | 3 | O | NH-iPr | CH | CH | — |
| 107 | Ph | Ph | H | S | 8 | 1 | O | NH-2,4-$C_6H_3F_2$ | CH | CH | — |
| 108 | Ph | Ph | H | S | 8 | 1 | O | NH-iPr | CH | CH | — |
| 109 | 4-MeO—$C_6H_4$ | 4-MeO—$C_6H_4$ | H | S | 8 | 1 | O | NH-2,4-$C_6H_3F_2$ | CH | CH | — |
| 110 | 4-MeO—$C_6H_4$ | 4-MeO—$C_6H_4$ | H | S | 8 | 1 | O | NH-iPr | CH | CH | — |
| 111 | Ph | Ph | H | S | 5 | 2 | O | NH-2,4-$C_6H_3F_2$ | N | CH | — |
| 112 | Ph | Ph | H | S | 5 | 2 | O | NH-iPr | N | CH | — |
| 113 | 4-MeO—$C_6H_4$ | 4-MeO—$C_6H_4$ | H | S | 5 | 2 | O | NH-2,4-$C_6H_3F_2$ | N | CH | — |
| 114 | 4-MeO—$C_6H_4$ | 4-MeO—$C_6H_4$ | H | S | 5 | 2 | O | NH-iPr | N | CH | — |
| 115 | Ph | Ph | H | S | 5 | 2 | O | NH-2,4-$C_6H_3F_2$ | $CH_2$ | N | — |
| 116 | Ph | Ph | H | S | 5 | 2 | O | NH-iPr | $CH_2$ | N | — |
| 117 | 4-MeO—$C_6H_4$ | 4-MeO—$C_6H_4$ | H | S | 5 | 2 | O | NH-2,4-$C_6H_3F_2$ | $CH_2$ | N | — |
| 118 | 4-MeO—$C_6H_4$ | 4-MeO—$C_6H_4$ | H | S | 5 | 2 | O | NH-iPr | $CH_2$ | N | — |
| 119 | Ph | Ph | H | S | 5 | 1 | S | NH-2,4-$C_6H_3F_2$ | CH | CH | — |
| 120 | Ph | Ph | H | $SO_2$ | 5 | 1 | O | NH-iPr | CH | CH | — |
| 121 | 4-MeO—$C_6H_4$ | 4-MeO—$C_6H_4$ | H | NH | 5 | 1 | O | NH-2,4-$C_6H_3F_2$ | CH | CH | — |
| 122 | 4-MeO—$C_6H_4$ | 4-MeO—$C_6H_4$ | H | $NCH_3$ | 5 | 1 | O | NH-iPr | CH | CH | — |
| 123 | Ph | Ph | Me | S | 5 | 1 | O | NH-2,4-$C_6H_3F_2$ | CH | CH | — |
| 124 | Ph | Ph | Ph | S | 5 | 1 | O | NH-iPr | CH | CH | — |
| 125 | 4-MeO—$C_6H_4$ | iPr | H | S | 5 | 1 | O | NH-2,4-$C_6H_3F_2$ | CH | CH | — |
| 126 | 4-MeS—$C_6H_4$ | 4-MeS—$C_6H_4$ | H | S | 5 | 1 | O | NH-iPr | CH | CH | — |
| 127 | 4-MeS—$C_6H_4$ | c$C_6H_{11}$ | H | S | 5 | 1 | O | NH-iPr | CH | CH | — |
| 128 | iPr | iPr | H | S | 5 | 1 | O | NH-iPr | CH | CH | — |
| 129 | Ph | Ph | H | S | 5 | 1 | $H_2$ | $C_3H_7$ | CH | CH | — |

TABLE 2-continued

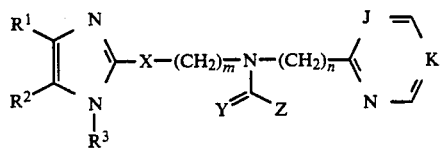

| Ex. No. | R¹ | R² | R³ | X | m | n | Y | Z | J | K | m.p. |
|---|---|---|---|---|---|---|---|---|---|---|---|
| 130 | Ph | Ph | H | S | 5 | 1 | O | NH-2,4-$C_6H_3F_2$ | N | N | — |

[a] $^1$H NMR ($CDCl_3$): 10.92(1H, br s); 8.68–8.60(1H, m); 7.78–7.59(2H, m); 7.49(2H, d, J=8.4Hz); 7.30(2H, d, J=8.4Hz); 7.29–7.20(2H, m); 6.84(4H, d, J=8.4Hz); 6.80–6.55(2H, m); 4.53(2H, s); 3.80(3H, s); 3.78(3H, s); 3.53(2H, t, J=6.6Hz); 2.89(2H, t, J=6.2Hz); 1.80–1.30(6H, m).

[b] $^1$H NMR ($CDCl_3$): 11.66(1H, br s); 8.51(1H, d, J=4.7Hz); 7.68(1H, td, J=7.7, 1.5Hz); 7.57–7.32(6H, m); 6.81(4H, d, J=8.4Hz); 6.12(1H, br d, J=6.2Hz); 4.39(2H, s); 3.79(6H, s); 3.79–3.70(1H, m); 3.49–3.39(2H, m); 2.93(2H, t, J=6.4Hz); 1.78–1.65(2H, m); 1.63–1.54(2H, m); 1.47–1.35(2H, m); 1.05(6H, d, J=6.6Hz).

[c] $^1$H NMR ($CDCl_3$): 8.87(1H, br s); 8.55(1H, d, J=3.7Hz); 7.67–7.58(2H, m); 7.44(4H, br); 7.30–7.17(8H, m); 6.77–6.68(1H, m); 6.61–6.54(1H, m); 3.87(2H, t, J=6.2Hz); 3.39(2H, t, J=6.9Hz); 3.15(2H, t, J=6.2Hz); 2.96(2H, t, J=6.6Hz); 1.80–1.45(6H, m).

[d] $^1$H NMR ($CDCl_3$): 8.52(1H, d, J=4.7Hz); 7.72–7.50(6H, m); 7.31–7.10(7H, m); 5.72(1H, br d, J=7.0Hz); 3.74(1H, m, J=7.0Hz); 3.61(2H, t, J=6.6Hz); 3.37(2H, t, J=6.6Hz); 3.05–2.96(4H, m); 1.81–1.32(6H, m); 1.01(6H, d, J=7.0Hz).

[e] $^1$H NMR ($CDCl_3$): 10.76(1H, br s); 8.82(1H, br s); 8.55(1H, d, J=4.4Hz); 7.69–7.59(2H, m); 7.57–7.42(4H, br); 7.25–7.14(2H, m); 6.79(4H, d, J=8.4Hz); 6.78–6.69(1H, m); 6.60(1H, td, J=7.2, 1.9Hz); 3.88(2H, t, J=6.3Hz); 3.79(6H, s); 3.40(2H, t, J=7.0Hz); 3.16(2H, t, J=6.2Hz); 2.97(2H, t, J=6.6Hz); 1.82–1.60(4H, m); 1.56–1.42(2H, m).

[f] $^1$H NMR ($CDCl_3$): 8.52(1H, d, J=4.5Hz); 7.62(1H, td, J=6.0, 2.0Hz); 7.46(4H, d, J=8.8Hz); 7.19–7.10(2H, m); 6.82(4H, d, J=8.8Hz); 5.73(1H, br d, J=5Hz); 4.03(1H, m, J=6.2Hz); 3.80(6H, s); 3.61(2H, t, J=6.6Hz); 3.37(2H, t, J=6.6Hz); 3.03(2H, t, J=6.6Hz); 2.96(2H, t, J=6.6Hz); 1.79–1.69(2H, m); 1.65–1.56(2H, m); 1.53–1.42(2H, m); 1.20(6H, d, H=6.2 Hz).

[g] $^1$H NMR ($CDCl_3$): 11.3(1H, s); 10.2–10.1(1H, m); 8.3–8.2(1H, m); 7.7–7.6(3H, m); 7.55–7.5(2H, m); 7.4–7.2(6H, m); 7.0–6.9(2H, m); 4.1–4.0(2H, m); 3.1–3.0(2H, m); 1.9–1.5(7H, m); 1.2–1.1(6H, m).

[h] $^1$H NMR ($CDCl_3$): 13.15(1H, s); 10.25(1H, s); 8.6–8.5(1H, m); 8.05–7.95(1H, m); 7.8–7.7(1H, m); 7.6(2H, d, J=7.0Hz); 7.4–7.15(8H, m); 7.1–7.0(2H, m); 6.85–6.75(1H, m); 6.7–6.6(1H, m); 4.1(2H, t, J=7.0Hz); 3.1(2H, t, J=6.6Hz); 1.9–1.5(6H, m).

TABLE 3

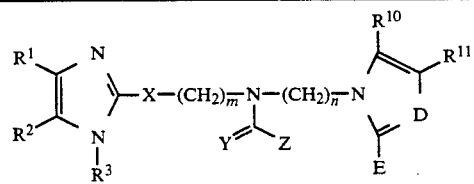

| Ex. No. | R¹ | R² | R³ | X | m | n | Y | Z | R¹⁰ | R¹¹ | D | E | m.p. |
|---|---|---|---|---|---|---|---|---|---|---|---|---|---|
| 131 | Ph | Ph | H | S | 5 | 3 | O | NH-iPr | H | H | N | H | — |
| 132 | Ph | Ph | H | S | 5 | 3 | O | NH-2,4-$C_6H_3F_2$ | H | H | N | H | — |
| 133 | Ph | Ph | H | S | 5 | 3 | O | $CH_2$-c$C_6H_{11}$ | H | H | N | H | — |
| 134 | Ph | Ph | H | S | 5 | 3 | O | O$CH_2$Ph | H | H | N | H | — |
| 135 | 4-MeO—$C_6H_4$ | 4-MeO—$C_6H_4$ | H | S | 5 | 3 | O | NH-iPr | H | H | N | H | 68–69 |
| 136 | 4-MeO—$C_6H_4$ | 4-MeO—$C_6H_4$ | H | S | 5 | 3 | O | NH-2,4-$C_6H_3F_2$ | H | H | N | H | — |
| 137 | 4-MeO—$C_6H_4$ | 4-MeO—$C_6H_4$ | H | S | 5 | 3 | O | $CH_2$-c$C_6H_{11}$ | H | H | N | H | — |
| 138 | 4-MeO—$C_6H_4$ | 4-MeO—$C_6H_4$ | H | S | 5 | 3 | O | O$CH_2$Ph | H | H | N | H | — |
| 139 | 4-$Me_2$N—$C_6H_4$ | 4-$Me_2$N—$C_6H_4$ | H | S | 5 | 3 | O | NH-iPr | H | H | N | H | — |
| 140 | 4-$Me_2$N—$C_6H_4$ | 4-$Me_2$N—$C_6H_4$ | H | S | 5 | 3 | O | NH-2,4-$C_6H_3F_2$ | H | H | N | H | — |
| 141 | 4-$Me_2$N—$C_6H_4$ | 4-$Me_2$N—$C_6H_4$ | H | S | 5 | 3 | O | $CH_2$-c$C_6H_{11}$ | H | H | N | H | — |
| 142 | 4-$Me_2$N—$C_6H_4$ | 4-$Me_2$N—$C_6H_4$ | H | S | 5 | 3 | O | O$CH_2$Ph | H | H | N | H | — |
| 143 | Ph | Ph | H | S | 5 | 5 | O | NH-iPr | —($C_4H_4$)— | | N | $CH_3$ | — |
| 144 | Ph | Ph | H | S | 5 | 5 | O | NH-2,4-$C_6H_3F_2$ | —($C_4H_4$)— | | N | $CH_3$ | — |
| 145 | Ph | Ph | H | S | 5 | 5 | O | $CH_2$-c$C_6H_{11}$ | —($C_4H_4$)— | | N | $CH_3$ | — |
| 146 | Ph | Ph | H | S | 5 | 5 | O | O$CH_2$Ph | —($C_4H_4$)— | | N | $CH_3$ | — |
| 147 | 4-MeO—$C_6H_4$ | 4-MeO—$C_6H_4$ | H | S | 5 | 5 | O | NH-iPr | —($C_4H_4$)— | | N | $CH_3$ | — |
| 148 | 4-MeO—$C_6H_4$ | 4-MeO—$C_6H_4$ | H | S | 5 | 5 | O | NH-2,4-$C_6H_3F_2$ | —($C_4H_4$)— | | N | $CH_3$ | — |
| 149 | 4-MeO—$C_6H_4$ | 4-MeO—$C_6H_4$ | H | S | 5 | 5 | O | $CH_2$-c$C_6H_{11}$ | —($C_4H_4$)— | | N | $CH_3$ | — |
| 150 | 4-MeO—$C_6H_4$ | 4-MeO—$C_6H_4$ | H | S | 5 | 5 | O | O$CH_2$Ph | —($C_4H_4$)— | | N | $CH_3$ | — |
| 151 | 4-$Me_2$N—$C_6H_4$ | 4-$Me_2$N—$C_6H_4$ | H | S | 5 | 5 | O | NH-iPr | —($C_4H_4$)— | | N | $CH_3$ | — |
| 152 | 4-$Me_2$N—$C_6H_4$ | 4-$Me_2$N—$C_6H_4$ | H | S | 5 | 5 | O | NH-2,4-$C_6H_3F_2$ | —($C_4H_4$)— | | N | $CH_3$ | — |
| 153 | 4-$Me_2$N—$C_6H_4$ | 4-$Me_2$N—$C_6H_4$ | H | S | 5 | 5 | O | $CH_2$-c$C_6H_{11}$ | —($C_4H_4$)— | | N | $CH_3$ | — |
| 154 | 4-$Me_2$N—$C_6H_4$ | 4-$Me_2$N—$C_6H_4$ | H | S | 5 | 5 | O | O$CH_2$Ph | —($C_4H_4$)— | | N | $CH_3$ | — |
| 155 | Ph | Ph | H | S | 5 | 5 | O | NH-iPr | —(N—CH)$_2$— | | N | H | — |
| 156 | Ph | Ph | H | S | 5 | 5 | O | NH-2,4-$C_6H_3F_2$ | —(N—CH)$_2$— | | N | H | — |
| 157 | Ph | Ph | H | S | 5 | 5 | O | $CH_2$-c$C_6H_{11}$ | —(N—CH)$_2$— | | N | H | — |
| 158 | Ph | Ph | H | S | 5 | 5 | O | O$CH_2$Ph | —(N—CH)$_2$— | | N | H | — |
| 159 | 4-MeO—$C_6H_4$ | 4-MeO—$C_6H_4$ | H | S | 5 | 5 | O | NH-iPr | —(N—CH)$_2$— | | N | H | — |
| 160 | 4-MeO—$C_6H_4$ | 4-MeO—$C_6H_4$ | H | S | 5 | 5 | O | NH-2,4-$C_6H_3F_2$ | —(N—CH)$_2$— | | N | H | — |
| 161 | 4-MeO—$C_6H_4$ | 4-MeO—$C_6H_4$ | H | S | 5 | 5 | O | $CH_2$-c$C_6H_{11}$ | —(N—CH)$_2$— | | N | H | — |
| 162 | 4-MeO—$C_6H_4$ | 4-MeO—$C_6H_4$ | H | S | 5 | 5 | O | O$CH_2$Ph | —(N—CH)$_2$— | | N | H | — |
| 163 | 4-$Me_2$N—$C_6H_4$ | 4-$Me_2$N—$C_6H_4$ | H | S | 5 | 5 | O | NH-iPr | —(N—CH)$_2$— | | N | H | — |
| 164 | 4-$Me_2$N—$C_6H_4$ | 4-$Me_2$N—$C_6H_4$ | H | S | 5 | 5 | O | NH-2,4-$C_6H_3F_2$ | —(N—CH)$_2$— | | N | H | — |
| 165 | 4-$Me_2$N—$C_6H_4$ | 4-$Me_2$N—$C_6H_4$ | H | S | 5 | 5 | O | $CH_2$-c$C_6H_{11}$ | —(N—CH)$_2$— | | N | H | — |
| 166 | 4-$Me_2$N—$C_6H_4$ | 4-$Me_2$N—$C_6H_4$ | H | S | 5 | 5 | O | O$CH_2$Ph | —(N—CH)$_2$— | | N | H | — |
| 167 | Ph | Ph | H | S | 3 | 5 | O | NH-iPr | Ph | Ph | N | $SCH_3$ | — |

TABLE 3-continued

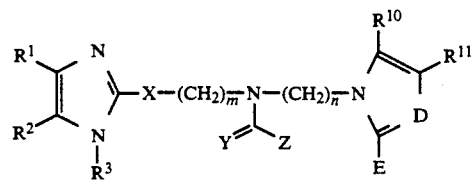

| Ex. No. | R¹ | R² | R³ | X | m | n | Y | Z | R¹⁰ | R¹¹ | D | E | m.p. |
|---|---|---|---|---|---|---|---|---|---|---|---|---|---|
| 168 | Ph | Ph | H | S | 3 | 8 | O | NH-iPr | H | H | N | H | — |
| 169 | Ph | Ph | H | S | 5 | 3 | S | NH-iPr | H | H | N | H | — |
| 170 | Ph | Ph | Me | S | 5 | 3 | O | NH-iPr | H | H | N | H | — |
| 171 | Ph | Ph | H | SO₂ | 5 | 3 | O | NH-iPr | H | H | N | H | — |
| 172 | Ph | Ph | H | S | 3 | 8 | O | NH-iPr | H | H | N | H | — |
| 173 | Ph | cC₆H₁₁ | H | S | 5 | 3 | O | NH-iPr | H | H | N | H | — |
| 174 | 4-MeS—C₆H₄ | Ph | H | S | 5 | 3 | O | NH-iPr | H | H | N | H | — |
| 175 | Ph | Ph | H | S | 5 | 3 | O | NH-iPr | —(C₄H₄)— | | CH | H | — |
| 176 | 4-MeO—C₆H₄ | 4-MeO—C₆H₄ | H | S | 5 | 3 | O | NH-iPr | —(C₄H₄)— | | CH | H | — |
| 177 | 4-Me₂N—C₆H₄ | 4-Me₂N—C₆H₄ | H | S | 5 | 3 | O | NH-iPr | —(C₄H₄)— | | CH | H | — |
| 178 | 4-MeS—C₆H₄ | 4-MeS—C₆H₄ | H | S | 5 | 3 | O | NH-iPr | —(C₄H₄)— | | CH | H | — |
| 179 | Ph | Ph | H | NH | 5 | 3 | O | NH-iPr | H | H | N | H | — |
| 180 | Ph | Ph | H | NMe | 5 | 3 | O | NH-iPr | H | H | N | H | — |
| 181 | Ph | Ph | H | SO₂ | 5 | 3 | H₂ | CH2-cC₆H₁₁ | H | H | N | H | — |
| 182 | Ph | Ph | H | S | 5 | 3 | O | NH-iPr | —(C₄H₄)— | | —(C₄H₄)— | | — |
| 183 | Ph | Ph | H | S | 5 | 3 | O | NH-2,4-C₆H₃F₂ | —(C₄H₄)— | | —(C₄H₄)— | | — |
| 184 | Ph | Ph | H | S | 5 | 3 | O | CH₂-cC₆H₁₁ | —(C₄H₄)— | | —(C₄H₄)— | | — |
| 185 | Ph | Ph | H | S | 5 | 3 | O | OCH₂Ph | —(C₄H₄)— | | —(C₄H₄)— | | — |
| 186 | 4-MeO—C₆H₄ | 4-MeO—C₆H₄ | H | S | 5 | 3 | O | NH-iPr | —(C₄H₄)— | | —(C₄H₄)— | | — |
| 187 | 4-MeO—C₆H₄ | 4-MeO—C₆H₄ | H | S | 5 | 3 | O | NH-2,4-C₆H₃F₂ | —(C₄H₄)— | | —(C₄H₄)— | | — |
| 188 | 4-MeO—C₆H₄ | 4-MeO—C₆H₄ | H | S | 5 | 3 | O | CH₂-cC₆H₁₁ | —(C₄H₄)— | | —(C₄H₄)— | | — |
| 189 | 4-MeO—C₆H₄ | 4-MeO—C₆H₄ | H | S | 5 | 3 | O | OCH₂Ph | —(C₄H₄)— | | —(C₄H₄)— | | — |
| 190 | 4-Me₂N—C₆H₄ | 4-Me₂N—C₆H₄ | H | S | 5 | 3 | O | NH-iPr | —(C₄H₄)— | | —(C₄H₄)— | | — |
| 191 | 4-Me₂N—C₆H₄ | 4-Me₂N—C₆H₄ | H | S | 5 | 3 | O | NH-2,4-C₆H₃F₂ | —(C₄H₄)— | | —(C₄H₄)— | | — |
| 192 | 4-Me₂N—C₆H₄ | 4-Me₂N—C₆H₄ | H | S | 5 | 3 | O | CH₂-cC₆H₁₁ | —(C₄H₄)— | | —(C₄H₄)— | | — |
| 193 | 4-Me₂N—C₆H₄ | 4-Me₂N—C₆H₄ | H | S | 5 | 3 | O | OCH₂Ph | —(C₄H₄)— | | —(C₄H₄)— | | — |
| 194 | 3-Cl—C₆H₄ | 3-Cl—C₆H₄ | H | S | 5 | 3 | O | NH-iPr | H | H | N | H | — |
| 195 | 3-Cl—C₆H₄ | 3-Cl—C₆H₄ | H | S | 5 | 3 | O | NH-2,4-C₆H₃F₂ | H | H | N | H | — |
| 196 | 3-Cl—C₆H₄ | 3-Cl—C₆H₄ | H | S | 5 | 3 | O | CH₂-cC₆H₁₁ | H | H | N | H | — |
| 197 | 3-Cl—C₆H₄ | 3-Cl—C₆H₄ | H | S | 5 | 3 | O | OCH₂Ph | H | H | N | H | — |
| 198 | 3-Cl—C₆H₄ | 3-Cl—C₆H₄ | H | S | 5 | 3 | O | NH-2-pyridyl | H | H | N | H | — |
| 199 | 3-Cl—C₆H₄ | 3-Cl—C₆H₄ | H | S | 5 | 3 | O | NH-4-C₆H₄NO₂ | H | H | N | H | — |
| 200 | 3-Cl—C₆H₄ | 3-Cl—C₆H₄ | H | S | 5 | 3 | O | NHPh | H | H | N | H | — |

TABLE 4

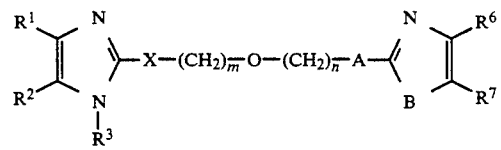

| Ex. No. | R¹ | R² | R³ | X | m | n | A | B | R⁶ | R⁷ | m.p. |
|---|---|---|---|---|---|---|---|---|---|---|---|
| 201 | Ph | Ph | H | S | 2 | 2 | S | NH | Ph | Ph | 232–234 |
| 202 | 4-MeO—C₆H₄ | 4-MeO—C₆H₄ | H | S | 2 | 2 | S | NH | 4-MeO—C₆H₄ | 4-MeO—C₆H₄ | — |
| 203 | 4-Me₂N—C₆H₄ | 4-Me₂N—C₆H₄ | H | S | 2 | 2 | S | NH | 4-Me₂N—C₆H₄ | 4-Me₂N—C₆H₄ | 137–139 |
| 204 | 4-MeO—C₆H₄ | 4-MeO—C₆H₄ | H | S | 2 | 2 | S | NH | Ph | Ph | 91–93 |
| 205 | 4-Me₂N—C₆H₄ | 4-Me₂N—C₆H₄ | H | S | 2 | 2 | S | NH | Ph | Ph | — |
| 206 | Ph | Ph | H | S | 3 | 3 | S | NH | Ph | Ph | — |
| 207 | 4-MeO—C₆H₄ | 4-MeO—C₆H₄ | H | S | 3 | 3 | S | NH | 4-MeO—C₆H₄ | 4-MeO—C₆H₄ | — |
| 208 | 4-Me₂N—C₆H₄ | 4-Me₂N—C₆H₄ | H | S | 3 | 3 | S | NH | 4-Me₂N—C₆H₄ | 4-Me₂N—C₆H₄ | — |
| 209 | 4-MeO—C₆H₄ | 4-MeO—C₆H₄ | H | S | 3 | 3 | S | NH | Ph | Ph | — |
| 210 | 4-Me₂N—C₆H₄ | 4-Me₂N—C₆H₄ | H | S | 3 | 3 | S | NH | Ph | Ph | — |
| 211 | Ph | Ph | H | S | 5 | 2 | S | NH | Ph | Ph | — |
| 212 | 4-MeO—C₆H₄ | 4-MeO—C₆H₄ | H | S | 5 | 2 | S | NH | 4-MeO—C₆H₄ | 4-MeO—C₆H₄ | — |
| 213 | 4-Me₂N—C₆H₄ | 4-Me₂N—C₆H₄ | H | S | 5 | 2 | S | NH | 4-Me₂N—C₆H₄ | 4-Me₂N—C₆H₄ | — |
| 214 | 4-MeO—C₆H₄ | 4-MeO—C₆H₄ | H | S | 5 | 2 | S | NH | Ph | Ph | — |
| 215 | 4-Me₂N—C₆H₄ | 4-Me₂N—C₆H₄ | H | S | 5 | 2 | S | NH | Ph | Ph | — |
| 216 | Ph | Ph | H | S | 2 | 2 | S | NH | —(C₄H₄)— | | — |
| 217 | 4-MeO—C₆H₄ | 4-MeO—C₆H₄ | H | S | 2 | 2 | S | NH | —(C₄H₄)— | | — |
| 218 | 4-Me₂N—C₆H₄ | 4-Me₂N—C₆H₄ | H | S | 2 | 2 | S | NH | —(C₄H₄)— | | — |
| 219 | 4-MeO—C₆H₄ | 4-MeO—C₆H₄ | H | S | 5 | 5 | S | NH | —(C₄H₄)— | | — |
| 220 | 4-Me₂N—C₆H₄ | 4-Me₂N—C₆H₄ | H | S | 5 | 5 | S | NH | —(C₄H₄)— | | — |
| 221 | Ph | Ph | H | S | 2 | 2 | S | O | —(C₄H₄)— | | — |
| 222 | 4-MeO—C₆H₄ | 4-MeO—C₆H₄ | H | S | 2 | 2 | S | O | —(C₄H₄)— | | — |
| 223 | 4-Me₂N—C₆H₄ | 4-Me₂N—C₆H₄ | H | S | 2 | 2 | S | O | —(C₄H₄)— | | — |

TABLE 4-continued $$R^1, R^2 \text{ with } N, N-R^3 \text{ ring} - X-(CH_2)_m-O-(CH_2)_n-A - \text{ring with } N, B, R^6, R^7$$

| Ex. No. | $R^1$ | $R^2$ | $R^3$ | X | m | n | A | B | $R^6$ | $R^7$ | m.p. |
|---|---|---|---|---|---|---|---|---|---|---|---|
| 224 | 4-MeO—C$_6$H$_4$ | 4-MeO—C$_6$H$_4$ | H | S | 5 | 5 | S | O | —(C$_4$H$_4$)— | | — |
| 225 | 4-Me$_2$N—C$_6$H$_4$ | 4-Me$_2$N—C$_6$H$_4$ | H | S | 5 | 5 | S | O | —(C$_4$H$_4$)— | | — |
| 226 | Ph | Ph | H | S | 2 | 2 | S | NH | —(CH—N—CH—N)— | | — |
| 227 | 4-MeO—C$_6$H$_4$ | 4-MeO—C$_6$H$_4$ | H | S | 2 | 2 | S | NH | —(CH—N—CH—N)— | | — |
| 228 | 4-Me$_2$N—C$_6$H$_4$ | 4-Me$_2$N—C$_6$H$_4$ | H | S | 2 | 2 | S | NH | —(CH—N—CH—N)— | | — |
| 229 | 4-MeO—C$_6$H$_4$ | 4-MeO—C$_6$H$_4$ | H | S | 5 | 5 | S | NH | —(CH—N—CH—N)— | | — |
| 230 | 4-Me$_2$N—C$_6$H$_4$ | 4-Me$_2$N—C$_6$H$_4$ | H | S | 5 | 5 | S | NH | —(CH—N—CH—N)— | | — |
| 231 | Ph | Ph | H | SO | 2 | 2 | SO | NH | Ph | Ph | — |
| 232 | 4-MeO—C$_6$H$_4$ | 4-MeO—C$_6$H$_4$ | H | SO | 2 | 2 | SO | NH | 4-MeO—C$_6$H$_4$ | 4-MeO—C$_6$H$_4$ | — |
| 233 | 4-Me$_2$N—C$_6$H$_4$ | 4-Me$_2$N—C$_6$H$_4$ | H | SO | 2 | 2 | SO | NH | 4-Me$_2$N—C$_6$H$_4$ | 4-Me$_2$N—C$_6$H$_4$ | — |
| 234 | 4-MeO—C$_6$H$_4$ | 4-MeO—C$_6$H$_4$ | H | SO | 2 | 2 | SO | NH | Ph | Ph | — |
| 235 | 4-Me$_2$N—C$_6$H$_4$ | 4-Me$_2$N—C$_6$H$_4$ | H | SO | 2 | 2 | SO | NH | Ph | Ph | — |
| 236 | Ph | Ph | H | SO$_2$ | 2 | 2 | SO$_2$ | NH | Ph | Ph | — |
| 237 | 4-MeO—C$_6$H$_4$ | 4-MeO—C$_6$H$_4$ | H | SO$_2$ | 2 | 2 | SO$_2$ | NH | 4-MeO—C$_6$H$_4$ | 4-MeO—C$_6$H$_4$ | — |
| 238 | 4-Me$_2$N—C$_6$H$_4$ | 4-Me$_2$N—C$_6$H$_4$ | H | SO$_2$ | 2 | 2 | SO$_2$ | NH | 4-Me$_2$N—C$_6$H$_4$ | 4-Me$_2$N—C$_6$H$_4$ | — |
| 239 | 4-MeO—C$_6$H$_4$ | 4-MeO—C$_6$H$_4$ | H | SO$_2$ | 2 | 2 | SO$_2$ | NH | Ph | Ph | — |
| 240 | 4-Me$_2$N—C$_6$H$_4$ | 4-Me$_2$N—C$_6$H$_4$ | H | SO$_2$ | 2 | 2 | SO$_2$ | NH | Ph | Ph | — |

TABLE 5

$$R^1, R^2 \text{ with } N, N-R^3 \text{ ring} - X-(CH_2)_m-O-(CH_2)_n- \text{ ring with } J, K, N$$

| Ex. No. | $R^1$ | $R^2$ | $R^3$ | X | m | n | J | K | m.p. |
|---|---|---|---|---|---|---|---|---|---|
| 241 | Ph | Ph | H | S | 2 | 2 | CH | CH | — |
| 242 | 4-CH$_3$O—C$_6$H$_4$ | 4-CH$_3$O—C$_6$H$_4$ | H | S | 2 | 2 | CH | CH | — |
| 243 | 4-CH$_3$S—C$_6$H$_4$ | 4-CH$_3$S—C$_6$H$_4$ | H | S | 2 | 2 | CH | CH | — |
| 244 | 4-(CH$_3$)$_2$N—C$_6$H$_4$ | 4-(CH$_3$)$_2$N—C$_6$H$_4$ | H | S | 2 | 2 | CH | CH | — |
| 245 | 4-CH$_3$S—C$_6$H$_4$ | Ph | H | S | 2 | 2 | CH | CH | — |
| 246 | 4-CH$_3$O—C$_6$H$_4$ | cC$_6$H$_{11}$ | H | S | 2 | 2 | CH | CH | — |
| 247 | iPr | iPr | H | S | 2 | 2 | CH | CH | — |
| 248 | Ph | Ph | CH$_3$ | S | 2 | 2 | CH | CH | — |
| 249 | Ph | Ph | Ph | S | 2 | 2 | CH | CH | — |
| 250 | Ph | Ph | H | NCH$_3$ | 2 | 2 | CH | CH | — |
| 251 | Ph | Ph | H | S | 5 | 2 | CH | CH | oil$^a$ |
| 252 | 4-CH$_3$O—C$_6$H$_4$ | 4-CH$_3$O—C$_6$H$_4$ | H | S | 5 | 2 | CH | CH | — |
| 253 | 4-CH$_3$S—C$_6$H$_4$ | 4-CH$_3$S—C$_6$H$_4$ | H | S | 5 | 2 | CH | CH | — |
| 254 | 4-(CH$_3$)$_2$N—C$_6$H$_4$ | 4-(CH$_3$)$_2$N—C$_6$H$_4$ | H | S | 5 | 2 | CH | CH | — |
| 255 | 4-CH$_3$S—C$_6$H$_4$ | Ph | H | S | 5 | 2 | CH | CH | — |
| 256 | 4-CH$_3$O—C$_6$H$_4$ | cC$_6$H$_{11}$ | H | S | 5 | 2 | CH | CH | — |
| 257 | iPr | iPr | H | S | 5 | 2 | CH | CH | — |
| 258 | Ph | Ph | CH$_3$ | S | 5 | 2 | CH | CH | — |
| 259 | Ph | Ph | Ph | S | 5 | 2 | CH | CH | — |
| 260 | Ph | Ph | H | NCH$_3$ | 5 | 2 | CH | CH | — |
| 261 | Ph | Ph | H | S | 3 | 5 | N | CH | — |
| 262 | 4-CH$_3$O—C$_6$H$_4$ | 4-CH$_3$O—C$_6$H$_4$ | H | S | 3 | 5 | N | CH | — |
| 263 | 4-CH$_3$S—C$_6$H$_4$ | 4-CH$_3$S—C$_6$H$_4$ | H | S | 3 | 5 | N | CH | — |
| 264 | 4-(CH$_3$)$_2$N—C$_6$H$_4$ | 4-(CH$_3$)$_2$N—C$_6$H$_4$ | H | S | 3 | 5 | N | CH | — |
| 265 | 4-CH$_3$S—C$_6$H$_4$ | Ph | H | S | 3 | 5 | N | CH | — |
| 266 | 4-CH$_3$O—C$_6$H$_4$ | cC$_6$H$_{11}$ | H | S | 3 | 5 | N | CH | — |
| 267 | iPr | iPr | H | S | 3 | 5 | N | CH | — |
| 268 | Ph | Ph | CH$_3$ | S | 3 | 5 | N | CH | — |
| 269 | Ph | Ph | Ph | S | 3 | 5 | N | CH | — |
| 270 | Ph | Ph | H | NCH$_3$ | 3 | 5 | N | CH | — |
| 271 | Ph | Ph | H | S | 3 | 5 | CH | N | — |
| 272 | 4-CH$_3$O—C$_6$H$_4$ | 4-CH$_3$O—C$_6$H$_4$ | H | S | 3 | 5 | CH | N | — |
| 273 | 4-CH$_3$S—C$_6$H$_4$ | 4-CH$_3$S—C$_6$H$_4$ | H | S | 3 | 5 | CH | N | — |
| 274 | 4-(CH$_3$)$_2$N—C$_6$H$_4$ | 4-(CH$_3$)$_2$N—C$_6$H$_4$ | H | S | 3 | 5 | CH | N | — |
| 275 | 4-CH$_3$S—C$_6$H$_4$ | Ph | H | S | 3 | 5 | CH | N | — |
| 276 | 4-CH$_3$O—C$_6$H$_4$ | cC$_6$H$_{11}$ | H | S | 3 | 5 | CH | N | — |
| 277 | iPr | iPr | H | S | 3 | 5 | CH | N | — |
| 278 | Ph | Ph | CH$_3$ | S | 3 | 5 | CH | N | — |
| 279 | Ph | Ph | Ph | S | 3 | 5 | CH | N | — |
| 280 | Ph | Ph | H | NCH$_3$ | 3 | 5 | CH | N | — |

TABLE 5-continued

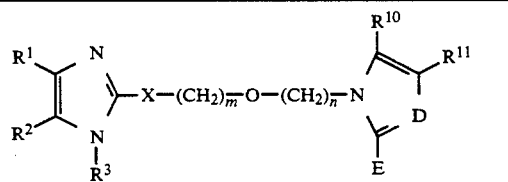

| Ex. No. | R¹ | R² | R³ | X | m | n | J | K | m.p. |
|---|---|---|---|---|---|---|---|---|---|
| 281 | Ph | Ph | H | S | 4 | 4 | C-Ph | N | — |
| 282 | 4-CH₃O—C₆H₄ | 4-CH₃O—C₆H₄ | H | S | 4 | 4 | C-Ph | N | — |
| 283 | 4-CH₃S—C₆H₄ | 4-CH₃S—C₆H₄ | H | S | 4 | 4 | C-Ph | N | — |
| 284 | 4-(CH₃)₂N—C₆H₄ | 4-(CH₃)₂N—C₆H₄ | H | S | 4 | 4 | C-Ph | N | — |
| 285 | 4-CH₃S—C₆H₄ | Ph | H | S | 4 | 4 | C-Ph | N | — |
| 286 | 4-CH₃O—C₆H₄ | cC₆H₁₁ | H | S | 4 | 4 | C-Ph | N | — |
| 287 | iPr | iPr | H | S | 4 | 4 | C-Ph | N | — |
| 288 | Ph | Ph | CH₃ | S | 4 | 4 | C-Ph | N | — |
| 289 | Ph | Ph | Ph | S | 4 | 4 | C-Ph | N | — |
| 290 | Ph | Ph | H | NCH₃ | 4 | 4 | C-Ph | N | — |
| 291 | Ph | Ph | H | S | 5 | 2 | C—CH₃ | C—CH₃ | — |
| 292 | 4-CH₃O—C₆H₄ | 4-CH₃O—C₆H₄ | H | S | 5 | 2 | C—CH₃ | C—CH₃ | — |
| 293 | 4-CH₃S—C₆H₄ | 4-CH₃S—C₆H₄ | H | S | 5 | 2 | C—CH₃ | C—CH₃ | — |
| 294 | 4-(CH₃)₂N—C₆H₄ | 4-(CH₃)₂N—C₆H₄ | H | S | 5 | 2 | C—CH₃ | C—CH₃ | — |
| 295 | 4-CH₃S—C₆H₄ | Ph | H | S | 5 | 2 | C—CH₃ | C—CH₃ | — |
| 296 | 4-CH₃O—C₆H₄ | cC₆H₁₁ | H | S | 5 | 2 | C—CH₃ | C—CH₃ | — |
| 297 | iPr | iPr | H | S | 5 | 2 | C—CH₃ | C—CH₃ | — |
| 298 | Ph | Ph | CH₃ | S | 5 | 2 | C—CH₃ | C—CH₃ | — |
| 299 | Ph | Ph | Ph | S | 5 | 2 | C—CH₃ | C—CH₃ | — |
| 300 | Ph | Ph | H | NCH₃ | 5 | 2 | C—CH₃ | C—CH₃ | — |
| 301 | Ph | Ph | H | SO₂ | 5 | 2 | CH | CH | — |
| 302 | 4-CH₃O—C₆H₄ | 4-CH₃O—C₆H₄ | H | SO₂ | 5 | 2 | CH | CH | — |
| 303 | 4-CH₃S—C₆H₄ | 4-CH₃S—C₆H₄ | H | SO₂ | 5 | 2 | CH | CH | — |
| 304 | 4-(CH₃)₂N—C₆H₄ | 4-(CH₃)₂N—C₆H₄ | H | SO₂ | 5 | 2 | CH | CH | — |
| 305 | 4-CH₃S—C₆H₄ | Ph | H | SO₂ | 5 | 2 | CH | CH | — |
| 306 | 4-CH₃O—C₆H₄ | cC₆H₁₁ | H | SO₂ | 5 | 2 | CH | CH | — |
| 307 | iPr | iPr | H | SO₂ | 5 | 2 | CH | CH | — |
| 308 | Ph | Ph | CH₃ | SO₂ | 5 | 2 | CH | CH | — |
| 309 | Ph | Ph | Ph | SO₂ | 5 | 2 | CH | CH | — |
| 310 | Ph | Ph | H | NC₂H₅ | 5 | 2 | CH | CH | — |

[a]¹H NMR (CDCl₃): 11.53(1H, br s); 8.48(1H, dt, J=5.1, 0.9Hz); 7.61-7.06(13H, m); 3.70(2H, t, J=6.6Hz); 3.37(2H, t, J=6.0Hz); 2.97(2H, t, J=7.3Hz); 2.94(2H, t, J=6.6Hz); 1.68-1.30(6H, m).

TABLE 6

| Ex. No. | R¹ | R² | R³ | X | m | n | R¹⁰ | R¹¹ | D | E | m.p. |
|---|---|---|---|---|---|---|---|---|---|---|---|
| 311 | Ph | Ph | H | S | 2 | 2 | —(C₄H₄)— | | N | iPr | — |
| 312 | 4-MeO—C₆H₄ | 4-MeO—C₆H₄ | H | S | 2 | 2 | —(C₄H₄)— | | N | iPr | — |
| 313 | 4-Me₂N—C₆H₄ | 4-Me₂N—C₆H₄ | H | S | 2 | 2 | —(C₄H₄)— | | N | iPr | — |
| 314 | 4-MeS—C₆H₄ | 4-MeS—C₆H₄ | H | S | 2 | 2 | —(C₄H₄)— | | H | iPr | — |
| 315 | 4-MeS—C₆H₄ | iPr | H | S | 2 | 2 | —(C₄H₄)— | | N | iPr | — |
| 316 | Ph | Ph | H | S | 2 | 2 | —(C₄H₄)— | | N | CH₃ | — |
| 317 | 4-MeO—C₆H₄ | 4-MeO—C₆H₄ | H | S | 2 | 2 | —(C₄H₄)— | | N | CH₃ | 77-79 |
| 318 | 4-Me₂N—C₆H₄ | 4-Me₂N—C₆H₄ | H | S | 2 | 2 | —(C₄H₄)— | | N | CH₃ | — |
| 319 | 4-MeS—C₆H₄ | 4-MeS—C₆H₄ | H | S | 2 | 2 | —(C₄H₄)— | | N | CH₃ | — |
| 320 | 4-MeS—C₆H₄ | iPr | H | S | 2 | 2 | —(C₄H₄)— | | N | CH₃ | — |
| 321 | Ph | Ph | H | S | 2 | 2 | —(C₄H₄)— | | N | SCH₃ | — |
| 322 | 4-MeO—C₆H₄ | 4-MeO—C₆H₄ | H | S | 2 | 2 | —(C₄H₄)— | | N | SCH₃ | — |
| 323 | 4-Me₂N—C₆H₄ | 4-Me₂N—C₆H₄ | H | S | 2 | 2 | —(C₄H₄)— | | N | SCH₃ | — |
| 324 | 4-MeS—C₆H₄ | 4-MeS—C₆H₄ | H | S | 2 | 2 | —(C₄H₄)— | | N | SCH₃ | — |
| 325 | 4-MeS—C₆H₄ | iPr | H | S | 2 | 2 | —(C₄H₄)— | | N | SCH₃ | — |
| 326 | Ph | Ph | H | S | 2 | 2 | —(N—CH—N—CH)— | | N | H | — |
| 327 | 4-MeO—C₆H₄ | 4-MeO—C₆H₄ | H | S | 2 | 2 | —(N—CH—N—CH)— | | N | H | — |
| 328 | 4-Me₂N—C₆H₄ | 4-Me₂N—C₆H₄ | H | S | 2 | 2 | —(N—CH—N—CH)— | | N | H | — |
| 329 | 4-MeS—C₆H₄ | 4-MeS—C₆H₄ | H | S | 2 | 2 | —(N—CH—N—CH)— | | N | H | — |
| 330 | 4-MeS—C₆H₄ | iPr | H | S | 2 | 2 | —(N—CH—N—CH)— | | N | H | — |
| 331 | Ph | Ph | H | S | 5 | 2 | —(C₄H₄)— | | N | CH₃ | — |
| 332 | 4-MeO—C₆H₄ | 4-MeO—C₆H₄ | H | S | 5 | 2 | —(C₄H₄)— | | N | CH₃ | — |
| 333 | 4-Me₂N—C₆H₄ | 4-Me₂N—C₆H₄ | H | S | 5 | 2 | —(C₄H₄)— | | N | CH₃ | — |
| 334 | 4-MeS—C₆H₄ | 4-MeS—C₆H₄ | H | S | 5 | 2 | —(C₄H₄)— | | N | CH₃ | — |

TABLE 6-continued $$\underset{R^3}{\overset{R^1}{\underset{R^2}{\bigvee}}}\underset{N}{\overset{N}{\bigvee}}-X-(CH_2)_m-O-(CH_2)_n-N\underset{E}{\overset{R^{10}}{\underset{D}{\bigvee}}}R^{11}$$

| Ex. No. | R¹ | R² | R³ | X | m | n | R¹⁰ | R¹¹ | D | E | m.p. |
|---|---|---|---|---|---|---|---|---|---|---|---|
| 335 | 4-MeS—C₆H₄ | iPr | H | S | 5 | 2 | —(C₄H₄)— | | N | CH₃ | — |
| 336 | Ph | Ph | H | S | 2 | 5 | —(C₄H₄)— | | N | CH₃ | — |
| 337 | 4-MeO—C₆H₄ | 4-MeO—C₆H₄ | H | S | 2 | 5 | —(C₄H₄)— | | N | CH₃ | — |
| 338 | 4-Me₂N—C₆H₄ | 4-Me₂N—C₆H₄ | H | S | 2 | 5 | —(C₄H₄)— | | N | CH₃ | — |
| 339 | 4-MeS—C₆H₄ | 4-MeS—C₆H₄ | H | S | 2 | 5 | —(C₄H₄)— | | N | CH₃ | — |
| 340 | 4-MeS—C₆H₄ | iPr | H | S | 2 | 5 | —(C₄H₄)— | | N | CH₃ | — |
| 341 | Ph | Ph | H | S | 2 | 2 | —(C₄H₄)— | | CH | CH₃ | — |
| 342 | 4-MeO—C₆H₄ | 4-MeO—C₆H₄ | H | S | 2 | 2 | —(C₄H₄)— | | CH | CH₃ | — |
| 343 | 4-Me₂N—C₆H₄ | 4-Me₂N—C₆H₄ | H | S | 2 | 2 | —(C₄H₄)— | | CH | CH₃ | — |
| 344 | 4-MeS—C₆H₄ | 4-MeS—C₆H₄ | H | S | 2 | 2 | —(C₄H₄)— | | CH | CH₃ | — |
| 345 | 4-MeS—C₆H₄ | iPr | H | S | 2 | 2 | —(C₄H₄)— | | CH | CH₃ | — |
| 346 | Ph | Ph | H | S | 2 | 2 | Ph | Ph | N | SCH₃ | — |
| 347 | 4-MeO—C₆H₄ | 4-MeO—C₆H₄ | H | S | 2 | 2 | Ph | Ph | N | SCH₃ | — |
| 348 | 4-Me₂N—C₆H₄ | 4-Me₂N—C₆H₄ | H | S | 2 | 2 | Ph | Ph | N | SCH₃ | — |
| 349 | 4-MeS—C₆H₄ | 4-MeS—C₆H₄ | H | S | 2 | 2 | Ph | Ph | N | SCH₃ | — |
| 350 | 4-MeS—C₆H₄ | iPr | H | S | 2 | 2 | Ph | Ph | N | SCH₃ | — |
| 351 | Ph | Ph | H | SO₂ | 2 | 2 | —(C₄H₄)— | | N | CH₃ | — |
| 352 | 4-MeO—C₆H₄ | 4-MeO—C₆H₄ | H | SO₂ | 2 | 2 | —(C₄H₄)— | | N | CH₃ | — |
| 353 | 4-Me₂N—C₆H₄ | 4-Me₂N—C₆H₄ | H | SO₂ | 2 | 2 | —(C₄H₄)— | | N | CH₃ | — |
| 354 | 4-MeS—C₆H₄ | 4-MeS—C₆H₄ | H | SO₂ | 2 | 2 | —(C₄H₄)— | | N | CH₃ | — |
| 355 | 4-MeS—C₆H₄ | iPr | H | SO₂ | 2 | 2 | —(C₄H₄)— | | N | CH₃ | — |
| 356 | Ph | Ph | H | CH₂ | 2 | 2 | —(C₄H₄)— | | N | CH₃ | — |
| 357 | 4-MeO—C₆H₄ | 4-MeO—C₆H₄ | H | NH | 2 | 2 | —(C₄H₄)— | | N | CH₃ | — |
| 358 | 4-Me₂N—C₆H₄ | 4-Me₂N—C₆H₄ | H | N—Me | 2 | 2 | —(C₄H₄)— | | N | CH₃ | — |
| 359 | 4-MeS—C₆H₄ | 4-MeS—C₆H₄ | CH₃ | S | 2 | 2 | —(C₄H₄)— | | N | CH₃ | — |
| 360 | 4-MeS—C₆H₄ | iPr | Ph | S | 2 | 2 | —(C₄H₄)— | | N | CH₃ | — |

TABLE 7

$$\underset{R^3}{\overset{R^1}{\underset{R^2}{\bigvee}}}\underset{N}{\overset{N}{\bigvee}}-X-(CH_2)_m-S(O)_q-(CH_2)_n-A\underset{B}{\overset{N}{\bigvee}}\underset{R^7}{\overset{R^6}{\bigvee}}$$

| Ex. No. | R¹ | R² | R³ | X | m | q | n | A | B | R⁶ | R⁷ | m.p. |
|---|---|---|---|---|---|---|---|---|---|---|---|---|
| 361 | Ph | Ph | H | S | 2 | 0 | 2 | S | NH | Ph | Ph | — |
| 362 | 4-MeO—C₆H₄ | 4-MeO—C₆H₄ | H | S | 2 | 0 | 2 | S | NH | 4-MeO—C₆H₄ | 4-MeO—C₆H₄ | — |
| 363 | 4-Me₂N—C₆H₄ | 4-Me₂N—C₆H₄ | H | S | 2 | 0 | 2 | S | NH | 4-Me₂N—C₆H₄ | 4-Me₂N—C₆H₄ | — |
| 364 | 4-MeO—C₆H₄ | 4-MeO—C₆H₄ | H | S | 2 | 0 | 2 | S | NH | Ph | Ph | — |
| 365 | 4-Me₂N—C₆H₄ | 4-Me₂N—C₆H₄ | H | S | 2 | 0 | 2 | S | NH | Ph | Ph | — |
| 366 | Ph | Ph | H | S | 3 | 0 | 3 | S | NH | Ph | Ph | 208–209 |
| 367 | 4-MeO—C₆H₄ | 4-MeO—C₆H₄ | H | S | 3 | 0 | 3 | S | NH | 4-MeO—C₆H₄ | 4-MeO—C₆H₄ | — |
| 368 | 4-Me₂N—C₆H₄ | 4-Me₂N—C₆H₄ | H | S | 3 | 0 | 3 | S | NH | 4-Me₂N—C₆H₄ | 4-Me₂N—C₆H₄ | — |
| 369 | 4-MeO—C₆H₄ | 4-MeO—C₆H₄ | H | S | 3 | 0 | 3 | S | NH | Ph | Ph | — |
| 370 | 4-Me₂N—C₆H₄ | 4-Me₂N—C₆H₄ | H | S | 3 | 0 | 3 | S | NH | Ph | Ph | — |
| 371 | Ph | Ph | H | S | 5 | 0 | 2 | S | NH | Ph | Ph | — |
| 372 | 4-MeO—C₆H₄ | 4-MeO—C₆H₄ | H | S | 5 | 0 | 2 | S | NH | 4-MeO—C₆H₄ | 4-MeO—C₆H₄ | — |
| 373 | 4-Me₂N—C₆H₄ | 4-Me₂N—C₆H₄ | H | S | 5 | 0 | 2 | S | NH | 4-Me₂N—C₆H₄ | 4-Me₂N—C₆H₄ | — |
| 374 | 4-MeO—C₆H₄ | 4-MeO—C₆H₄ | H | S | 5 | 0 | 2 | S | NH | Ph | Ph | — |
| 375 | 4-Me₂N—C₆H₄ | 4-Me₂N—C₆H₄ | H | S | 5 | 0 | 2 | S | NH | Ph | Ph | — |
| 376 | Ph | Ph | H | S | 2 | 0 | 2 | S | NH | —(C₄H₄)— | | — |
| 377 | 4-MeO—C₆H₄ | 4-MeO—C₆H₄ | H | S | 2 | 0 | 2 | S | NH | —(C₄H₄)— | | — |
| 378 | 4-Me₂N—C₆H₄ | 4-Me₂N—C₆H₄ | H | S | 2 | 0 | 2 | S | NH | —(C₄H₄)— | | — |
| 379 | 4-MeO—C₆H₄ | 4-MeO—C₆H₄ | H | S | 5 | 0 | 5 | S | NH | —(C₄H₄)— | | — |
| 380 | 4-Me₂N—C₆H₄ | 4-Me₂N—C₆H₄ | H | S | 5 | 0 | 5 | S | NH | —(C₄H₄)— | | — |
| 381 | Ph | Ph | H | S | 2 | 0 | 2 | S | O | —(C₄H₄)— | | — |
| 382 | 4-MeO—C₆H₄ | 4-MeO—C₆H₄ | H | S | 2 | 0 | 2 | S | O | —(C₄H₄)— | | — |
| 383 | 4-Me₂N—C₆H₄ | 4-Me₂N—C₆H₄ | H | S | 2 | 0 | 2 | S | O | —(C₄H₄)— | | — |
| 384 | 4-MeO—C₆H₄ | 4-MeO—C₆H₄ | H | S | 5 | 0 | 5 | S | O | —(C₄H₄)— | | — |
| 385 | 4-Me₂N—C₆H₄ | 4-Me₂N—C₆H₄ | H | S | 5 | 0 | 5 | S | O | —(C₄H₄)— | | — |
| 386 | Ph | Ph | H | S | 2 | 0 | 2 | S | NH | —(NCH)₂— | | — |
| 387 | 4-MeO—C₆H₄ | 4-MeO—C₆H₄ | H | S | 2 | 0 | 2 | S | NH | —(NCH)₂— | | — |
| 388 | 4-Me₂N—C₆H₄ | 4-Me₂N—C₆H₄ | H | S | 2 | 0 | 2 | S | NH | —(NCH)₂— | | — |
| 389 | 4-MeO—C₆H₄ | 4-MeO—C₆H₄ | H | S | 5 | 0 | 5 | S | NH | —(NCH)₂— | | — |
| 390 | 4-Me₂N—C₆H₄ | 4-Me₂N—C₆H₄ | H | S | 5 | 0 | 5 | S | NH | —(NCH)₂— | | — |

TABLE 7-continued

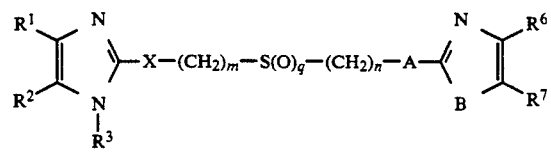

| Ex. No. | R¹ | R² | R³ | X | m | q | n | A | B | R⁶ | R⁷ | m.p. |
|---|---|---|---|---|---|---|---|---|---|---|---|---|
| 391 | Ph | Ph | H | SO | 2 | 1 | 2 | SO | NH | Ph | Ph | — |
| 392 | 4-MeO—C₆H₄ | 4-MeO—C₆H₄ | H | SO | 2 | 1 | 2 | SO | NH | 4-MeO—C₆H₄ | 4-MeO—C₆H₄ | — |
| 393 | 4-Me₂N—C₆H₄ | 4-Me₂N—C₆H₄ | H | SO | 2 | 1 | 2 | SO | NH | 4-Me₂N—C₆H₄ | 4-Me₂N—C₆H₄ | — |
| 394 | 4-MeO—C₆H₄ | 4-MeO—C₆H₄ | H | SO | 2 | 1 | 2 | SO | NH | Ph | Ph | — |
| 395 | 4-Me₂N—C₆H₄ | 4-Me₂N—C₆H₄ | H | SO | 2 | 1 | 2 | SO | NH | Ph | Ph | — |
| 396 | Ph | Ph | H | SO₂ | 2 | 2 | 2 | SO₂ | NH | Ph | Ph | — |
| 397 | 4-MeO—C₆H₄ | 4-MeO—C₆H₄ | H | SO₂ | 2 | 2 | 2 | SO₂ | NH | 4-MeO—C₆H₄ | 4-MeO—C₆H₄ | — |
| 398 | 4-Me₂N—C₆H₄ | 4-Me₂N—C₆H₄ | H | SO₂ | 2 | 2 | 2 | SO₂ | NH | 4-Me₂N—C₆H₄ | 4-Me₂N—C₆H₄ | — |
| 399 | 4-MeO—C₆H₄ | 4-MeO—C₆H₄ | H | SO₂ | 2 | 2 | 2 | SO₂ | NH | Ph | Ph | — |
| 400 | 4-Me₂N—C₆H₄ | 4-Me₂N—C₆H₄ | H | SO₂ | 2 | 2 | 2 | SO₂ | NH | Ph | Ph | — |

TABLE 8

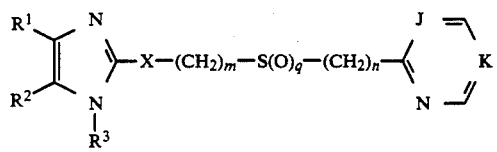

| Ex. No. | R¹ | R² | R³ | X | m | q | n | J | K | m.p. |
|---|---|---|---|---|---|---|---|---|---|---|
| 401 | Ph | Ph | H | S | 2 | 0 | 2 | CH | CH | — |
| 402 | 4-CH₃O—C₆H₄ | 4-CH₃O—C₆H₄ | H | S | 2 | 0 | 2 | CH | CH | — |
| 403 | 4-CH₃S—C₆H₄ | 4-CH₃S—C₆H₄ | H | S | 2 | 0 | 2 | CH | CH | — |
| 404 | 4-(CH₃)₂N—C₆H₄ | 4-(CH₃)₂N—C₆H₄ | H | S | 2 | 0 | 2 | CH | CH | — |
| 405 | 4-CH₃S—C₆H₄ | Ph | H | S | 2 | 0 | 2 | CH | CH | — |
| 406 | 4-CH₃O—C₆H₄ | cC₆H₁₁ | H | S | 2 | 0 | 2 | CH | CH | — |
| 407 | iPr | iPr | H | S | 2 | 0 | 2 | CH | CH | — |
| 408 | Ph | Ph | CH₃ | S | 2 | 0 | 2 | CH | CH | — |
| 409 | Ph | Ph | Ph | S | 2 | 0 | 2 | CH | CH | — |
| 410 | Ph | Ph | H | NCH₃ | 2 | 0 | 2 | CH | CH | — |
| 411 | Ph | Ph | H | S | 5 | 0 | 1 | CH | CH | oil$^a$ |
| 412 | 4-CH₃O—C₆H₄ | 4-CH₃O—C₆H₄ | H | S | 5 | 0 | 1 | CH | CH | — |
| 413 | 4-CH₃S—C₆H₄ | 4-CH₃S—C₆H₄ | H | S | 5 | 0 | 1 | CH | CH | — |
| 414 | 4-(CH₃)₂N—C₆H₄ | 4-(CH₃)₂N—C₆H₄ | H | S | 5 | 0 | 1 | CH | CH | — |
| 415 | 4-CH₃S—C₆H₄ | Ph | H | S | 5 | 0 | 1 | CH | CH | — |
| 416 | 4-CH₃O—C₆H₄ | cC₆H₁₁ | H | S | 5 | 0 | 1 | CH | CH | — |
| 417 | iPr | iPr | H | S | 5 | 0 | 1 | CH | CH | — |
| 418 | Ph | Ph | CH₃ | S | 5 | 0 | 1 | CH | CH | — |
| 419 | Ph | Ph | Ph | S | 5 | 0 | 1 | CH | CH | — |
| 420 | Ph | Ph | H | NCH₃ | 5 | 0 | 1 | CH | CH | — |
| 421 | Ph | Ph | H | S | 3 | 0 | 5 | N | CH | — |
| 422 | 4-CH₃O—C₆H₄ | 4-CH₃O—C₆H₄ | H | S | 3 | 0 | 5 | N | CH | — |
| 423 | 4-CH₃S—C₆H₄ | 4-CH₃S—C₆H₄ | H | S | 3 | 0 | 5 | N | CH | — |
| 424 | 4-(CH₃)₂N—C₆H₄ | 4-(CH₃)₂N—C₆H₄ | H | S | 3 | 0 | 5 | N | CH | — |
| 425 | 4-CH₃S—C₆H₄ | Ph | H | S | 3 | 0 | 5 | N | CH | — |
| 426 | 4-CH₃O—C₆H₄ | cC₆H₁₁ | H | S | 3 | 0 | 5 | N | CH | — |
| 427 | iPr | iPr | H | S | 3 | 0 | 5 | N | CH | — |
| 428 | Ph | Ph | CH₃ | S | 3 | 0 | 5 | N | CH | — |
| 429 | Ph | Ph | Ph | S | 3 | 0 | 5 | N | CH | — |
| 430 | Ph | Ph | H | NCH₃ | 3 | 0 | 5 | N | CH | — |
| 431 | Ph | Ph | H | S | 3 | 0 | 5 | CH | N | — |
| 432 | 4-CH₃O—C₆H₄ | 4-CH₃O—C₆H₄ | H | S | 3 | 0 | 5 | CH | N | — |
| 433 | 4-CH₃S—C₆H₄ | 4-CH₃S—C₆H₄ | H | S | 3 | 0 | 5 | CH | N | — |
| 434 | 4-(CH₃)₂N—C₆H₄ | 4-(CH₃)₂N—C₆H₄ | H | S | 3 | 0 | 5 | CH | N | — |
| 435 | 4-CH₃S—C₆H₄ | Ph | H | S | 3 | 0 | 5 | CH | N | — |
| 436 | 4-CH₃O—C₆H₄ | cC₆H₁₁ | H | S | 3 | 0 | 5 | CH | N | — |
| 437 | iPr | iPr | H | S | 3 | 0 | 5 | CH | N | — |
| 438 | Ph | Ph | CH₃ | S | 3 | 0 | 5 | CH | N | — |
| 439 | Ph | Ph | Ph | S | 3 | 0 | 5 | CH | N | — |
| 440 | Ph | Ph | H | NCH₃ | 3 | 0 | 5 | CH | N | — |
| 441 | Ph | Ph | H | S | 4 | 0 | 4 | C—Ph | N | — |
| 442 | 4-CH₃O—C₆H₄ | 4-CH₃O—C₆H₄ | H | S | 4 | 0 | 4 | C—Ph | N | — |
| 443 | 4-CH₃S—C₆H₄ | 4-CH₃S—C₆H₄ | H | S | 4 | 0 | 4 | C—Ph | N | — |
| 444 | 4-(CH₃)₂N—C₆H₄ | 4-(CH₃)₂N—C₆H₄ | H | S | 4 | 0 | 4 | C—Ph | N | — |
| 445 | 4-CH₃S—C₆H₄ | Ph | H | S | 4 | 0 | 4 | C—Ph | N | — |
| 446 | 4-CH₃O—C₆H₄ | cC₆H₁₁ | H | S | 4 | 0 | 4 | C—Ph | N | — |
| 447 | iPr | iPr | H | S | 4 | 0 | 4 | C—Ph | N | — |
| 448 | Ph | Ph | CH₃ | S | 4 | 0 | 4 | C—Ph | N | — |

TABLE 8-continued $$R^1\text{-...-N=...-X-(CH}_2)_m\text{-S(O)}_q\text{-(CH}_2)_n\text{-...-J...K...N}$$

| Ex. No. | R¹ | R² | R³ | X | m | q | n | J | K | m.p. |
|---|---|---|---|---|---|---|---|---|---|---|
| 449 | Ph | Ph | Ph | S | 4 | 0 | 4 | C—Ph | N | — |
| 450 | Ph | Ph | H | NCH₃ | 4 | 0 | 4 | C—Ph | N | — |
| 451 | Ph | Ph | H | S | 5 | 0 | 2 | C—CH₃ | C—CH₃ | — |
| 452 | 4-CH₃O—C₆H₄ | 4-CH₃O—C₆H₄ | H | S | 5 | 0 | 2 | C—CH₃ | C—CH₃ | — |
| 453 | 4-CH₃S—C₆H₄ | 4-CH₃S—C₆H₄ | H | S | 5 | 0 | 2 | C—CH₃ | C—CH₃ | — |
| 454 | 4-(CH₃)₂N—C₆H₄ | 4-(CH₃)₂N—C₆H₄ | H | S | 5 | 0 | 2 | C—CH₃ | C—CH₃ | — |
| 455 | 4-CH₃S—C₆H₄ | Ph | H | S | 5 | 0 | 2 | C—CH₃ | C—CH₃ | — |
| 456 | 4-CH₃O—C₆H₄ | cC₆H₁₁ | H | S | 5 | 0 | 2 | C—CH₃ | C—CH₃ | — |
| 457 | iPr | iPr | H | S | 5 | 0 | 2 | C—CH₃ | C—CH₃ | — |
| 458 | Ph | Ph | CH₃ | S | 5 | 0 | 2 | C—CH₃ | C—CH₃ | — |
| 459 | Ph | Ph | Ph | S | 5 | 0 | 2 | C—CH₃ | C—CH₃ | — |
| 460 | Ph | Ph | H | NCH₃ | 5 | 0 | 2 | C—CH₃ | C—CH₃ | — |
| 461 | Ph | Ph | H | SO₂ | 5 | 2 | 2 | CH | CH | — |
| 462 | 4-CH₃O—C₆H₄ | 4-CH₃O—C₆H₄ | H | SO₂ | 5 | 2 | 2 | CH | CH | — |
| 463 | 4-CH₃S—C₆H₄ | 4-CH₃S—C₆H₄ | H | SO₂ | 5 | 2 | 2 | CH | CH | — |
| 464 | 4-(CH₃)₂N—C₆H₄ | 4-(CH₃)₂N—C₆H₄ | H | SO₂ | 5 | 2 | 2 | CH | CH | — |
| 465 | 4-CH₃S—C₆H₄ | Ph | H | SO₂ | 5 | 2 | 2 | CH | CH | — |
| 466 | 4-CH₃O—C₆H₄ | cC₆H₁₁ | H | SO₂ | 5 | 2 | 2 | CH | CH | — |
| 467 | iPr | iPr | H | SO₂ | 5 | 2 | 2 | CH | CH | — |
| 468 | Ph | Ph | CH₃ | SO₂ | 5 | 2 | 2 | CH | CH | — |
| 469 | Ph | Ph | Ph | SO₂ | 5 | 2 | 2 | CH | CH | — |
| 470 | Ph | Ph | H | NC₂H₅ | 5 | 2 | 2 | CH | CH | — |

[a] ¹H NMR (CDCl₃): 10.16(1H, br s); 8.46(1H, dd, J=5.1, 0.7Hz); 7.70–7.58(3H, m); 7.40–7.10(10H, m); 3.77(2H, s); 3.07(2H, t, J=7.0Hz); 2.46(2H, t, J=7.3Hz); 1.77–1.48(6H, m).

TABLE 9

| Ex. No. | R¹ | R² | R³ | X | m | q | n | R¹⁰ R¹¹ | D | E | m.p. |
|---|---|---|---|---|---|---|---|---|---|---|---|
| 471 | Ph | Ph | H | S | 2 | 0 | 2 | —(C₄H₄)— | N | iPr | — |
| 472 | 4-MeO—C₆H₄ | 4-MeO—C₆H₄ | H | S | 2 | 0 | 2 | —(C₄H₄)— | N | iPr | — |
| 473 | 4-Me₂N—C₆H₄ | 4-Me₂N—C₆H₄ | H | S | 2 | 0 | 2 | —(C₄H₄)— | N | iPr | — |
| 474 | 4-MeS—C₆H₄ | 4-MeS—C₆H₄ | H | S | 2 | 0 | 2 | —(C₄H₄)— | N | iPr | — |
| 475 | 4-MeS—C₆H₄ | iPr | H | S | 2 | 0 | 2 | —(C₄H₄)— | N | iPr | — |
| 476 | Ph | Ph | H | S | 3 | 0 | 3 | —(C₄H₄)— | N | CH₃ | oil[a] |
| 477 | 4-MeO—C₆H₄ | 4-MeO—C₆H₄ | H | S | 3 | 0 | 3 | —(C₄H₄)— | N | CH₃ | — |
| 478 | 4-Me₂N—C₆H₄ | 4-Me₂N—C₆H₄ | H | S | 3 | 0 | 3 | —(C₄H₄)— | N | CH₃ | — |
| 479 | 4-MeS—C₆H₄ | 4-MeS—C₆H₄ | H | S | 3 | 0 | 3 | —(C₄H₄)— | N | CH₃ | — |
| 480 | 4-MeS—C₆H₄ | iPr | H | S | 3 | 0 | 3 | —(C₄H₄)— | N | CH₃ | — |
| 481 | Ph | Ph | H | S | 2 | 0 | 2 | —(C₄H₄)— | N | SCH₃ | — |
| 482 | 4-MeO—C₆H₄ | 4-MeO—C₆H₄ | H | S | 2 | 0 | 2 | —(C₄H₄)— | N | SCH₃ | — |
| 483 | 4-Me₂N—C₆H₄ | 4-Me₂N—C₆H₄ | H | S | 2 | 0 | 2 | —(C₄H₄)— | N | SCH₃ | — |
| 484 | 4-MeS—C₆H₄ | 4-MeS—C₆H₄ | H | S | 2 | 0 | 2 | —(C₄H₄)— | N | SCH₃ | — |
| 485 | 4-MeS—C₆H₄ | iPr | H | S | 2 | 0 | 2 | —(C₄H₄)— | N | SCH₃ | — |
| 486 | Ph | Ph | H | S | 2 | 0 | 2 | —(NCH)₂— | N | H | — |
| 487 | 4-MeO—C₆H₄ | 4-MeO—C₆H₄ | H | S | 2 | 0 | 2 | —(NCH)₂— | N | H | — |
| 488 | 4-Me₂N—C₆H₄ | 4-Me₂N—C₆H₄ | H | S | 2 | 0 | 2 | —(NCH)₂— | N | H | — |
| 489 | 4-MeS—C₆H₄ | 4-MeS—C₆H₄ | H | S | 2 | 0 | 2 | —(NCH)₂— | N | H | — |
| 490 | 4-MeS—C₆H₄ | iPr | H | S | 2 | 0 | 2 | —(NCH)₂— | N | H | — |
| 491 | Ph | Ph | H | S | 5 | 0 | 2 | —(C₄H₄)— | N | CH₃ | — |
| 492 | 4-MeO—C₆H₄ | 4-MeO—C₆H₄ | H | S | 5 | 0 | 2 | —(C₄H₄)— | N | CH₃ | — |
| 493 | 4-Me₂N—C₆H₄ | 4-Me₂N—C₆H₄ | H | S | 5 | 0 | 2 | —(C₄H₄)— | N | CH₃ | — |
| 494 | 4-MeS—C₆H₄ | 4-MeS—C₆H₄ | H | S | 5 | 0 | 2 | —(C₄H₄)— | N | CH₃ | — |
| 495 | 4-MeS—C₆H₄ | iPr | H | S | 5 | 0 | 2 | —(C₄H₄)— | N | CH₃ | — |
| 496 | Ph | Ph | H | S | 2 | 0 | 5 | —(C₄H₄)— | N | CH₃ | — |
| 497 | 4-MeO—C₆H₄ | 4-MeO—C₆H₄ | H | S | 2 | 0 | 5 | —(C₄H₄)— | N | CH₃ | — |
| 498 | 4-Me₂N—C₆H₄ | 4-Me₂N—C₆H₄ | H | S | 2 | 0 | 5 | —(C₄H₄)— | N | CH₃ | — |
| 499 | 4-MeS—C₆H₄ | 4-MeS—C₆H₄ | H | S | 2 | 0 | 5 | —(C₄H₄)— | N | CH₃ | — |
| 500 | 4-MeS—C₆H₄ | iPr | H | S | 2 | 0 | 5 | —(C₄H₄)— | N | CH₃ | — |
| 501 | Ph | Ph | H | S | 2 | 0 | 2 | —(C₄H₄)— | CH | CH₃ | — |
| 502 | 4-MeO—C₆H₄ | 4-MeO—C₆H₄ | H | S | 2 | 0 | 2 | —(C₄H₄)— | CH | CH₃ | — |
| 503 | 4-Me₂N—C₆H₄ | 4-Me₂N—C₆H₄ | H | S | 2 | 0 | 2 | —(C₄H₄)— | CH | CH₃ | — |

TABLE 9-continued

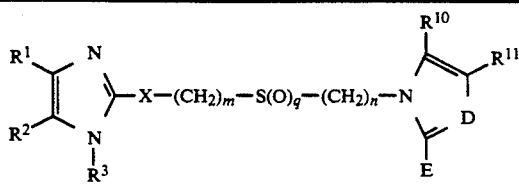

| Ex. No. | R¹ | R² | R³ | X | m | q | n | R¹⁰ | R¹¹ | D | E | m.p. |
|---|---|---|---|---|---|---|---|---|---|---|---|---|
| 504 | 4-MeS—C₆H₄ | 4-MeS—C₆H₄ | H | S | 2 | 0 | 2 | —(C₄H₄)— | | CH | CH₃ | — |
| 505 | 4-MeS—C₆H₄ | iPr | H | S | 2 | 0 | 2 | —(C₄H₄)— | | CH | CH₃ | — |
| 506 | Ph | Ph | H | S | 2 | 0 | 2 | Ph | Ph | N | SCH₃ | — |
| 507 | 4-MeO—C₆H₄ | 4-MeO—C₆H₄ | H | S | 2 | 0 | 2 | Ph | Ph | N | SCH₃ | — |
| 508 | 4-Me₂N—C₆H₄ | 4-Me₂N—C₆H₄ | H | S | 2 | 0 | 2 | Ph | Ph | N | SCH₃ | — |
| 509 | 4-MeS—C₆H₄ | 4-MeS—C₆H₄ | H | S | 2 | 0 | 2 | Ph | Ph | N | SCH₃ | — |
| 510 | 4-MeS—C₆H₄ | iPr | H | S | 2 | 0 | 2 | Ph | Ph | N | SCH₃ | — |
| 511 | Ph | Ph | H | SO₂ | 2 | 2 | 2 | —(C₄H₄)— | | N | CH₃ | — |
| 512 | 4-MeO—C₆H₄ | 4-MeO—C₆H₄ | H | SO₂ | 2 | 2 | 2 | —(C₄H₄)— | | N | CH₃ | — |
| 513 | 4-Me₂N—C₆H₄ | 4-Me₂N—C₆H₄ | H | SO₂ | 2 | 2 | 2 | —(C₄H₄)— | | N | CH₃ | — |
| 514 | 4-MeS—C₆H₄ | 4-MeS—C₆H₄ | H | SO₂ | 2 | 2 | 2 | —(C₄H₄)— | | N | CH₃ | — |
| 515 | 4-MeS—C₆H₄ | iPr | H | SO₂ | 2 | 2 | 2 | —(C₄H₄)— | | N | CH₃ | — |
| 516 | Ph | Ph | H | CH₂ | 2 | 2 | 2 | —(C₄H₄)— | | N | CH₃ | — |
| 517 | 4-MeO—C₆H₄ | 4-MeO—C₆H₄ | H | NH | 2 | 0 | 2 | —(C₄H₄)— | | N | CH₃ | — |
| 518 | 4-Me₂N—C₆H₄ | 4-Me₂N—C₆H₄ | H | N—Me | 2 | 0 | 2 | —(C₄H₄)— | | N | CH₃ | — |
| 519 | 4-MeS—C₆H₄ | 4-MeS—C₆H₄ | Me | S | 2 | 0 | 2 | —(C₄H₄)— | | N | CH₃ | — |
| 520 | 4-MeS—C₆H₄ | iPr | Ph | S | 2 | 0 | 2 | —(C₄H₄)— | | N | CH₃ | — |

[a]¹H NMR (CDCl₃): 7.61-7.45(5H, m); 7.34-7.18(9H, m); 4.16(2H, t, J=7.0Hz); 3.12(2H, t, J=7.0Hz); 2.59(2H, t, J=7.0Hz); 2.54(3H, s); 2.44(2H, t, J=6.8Hz); 2.03(2H, pentet, J=7.0Hz); 1.93(2H, pentet, J=7.1Hz).

What is claimed is:

1. A compound of the formula:

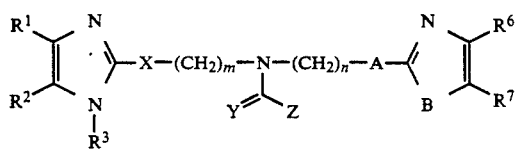

or stereosiomers and pharmaceutically acceptable salts thereof wherein:

X is $S(O)_p$, $CH_2$ or $NR^4$;
A is $CH_2$, O, S, $S(O)_r$ or $NR^8$;
B is $NR^9$;
Y is O, S or $H_2$;
Z is $NHR^5$, $OR^5$ or $R^5$
$R^1$, $R^2$, $R^6$ and $R^7$ are selected independently from H, $C_1$-$C_8$ alkyl, $C_3$-$C_8$ branched alkyl, $C_3$-$C_7$ cycloalkyl, thienyl, furanyl, or phenyl optionally substituted with 1-3 groups independently selected from $C_1$-$C_4$ alkoxy, $C_1$-$C_4$ alkyl, $CH_3S(O)_t$, F, or $NR^{15}R^{16}$;
$R^3$ is H, and $C_1$-$C_6$ alkyl, allyl, benzyl, or phenyl, each being optionally substituted with F, Cl, $CH_3$, $OCH_3$, or $CF_3$;
$R^5$ is $C_1$-$C_8$ alkenyl, $C_1$-$C_8$ alkynyl, $C_3$-$C_7$ cycloalkyl, $C_4$-$C_{10}$ cycloalkyl, $C_7$-$C_{14}$ aralkyl, phenyl optionally substituted with 1-3 groups independently selected from $C_1$-$C_4$ alkyl, $C_3$-$C_8$ branched alkyl, F, Cl, $C_1$-$C_4$ alkoxy, or CN, pyrrolidyl, or imidazolyl;
$R^4$, $R^8$, $R^9$, $R^{15}$, and $R^{16}$ are selected independently from H, $C_1$-$C_8$ alkyl, benzyl, or phenyl;
m is 2-8;
n is 0-5; and
p, r and t are independently 0-2.

2. The compound of claim 1 which is:
1,1-bis[5-(4,5-bis(4-methoxyphenyl)-1H-imidazol-2-ylthio)]-pentyl-3-(2-methyl ethyl)-urea.

3. A compound of claim 1, and stereosiomers and pharmaceutically acceptable salts thereof, selected from the group consisting of:
1,1-bis[5-(4,5-bis(4-methoxyphenyl)-1H-imidazol-2-ylthio)]pentyl-3-(2-methylethyl)-urea;
1-[5-(4,5-bis(4-methoxyphenyl)-1H-imidazol-2-ylthio)]-pentyl-1-[5-(4,5-diphenyl-1H-imidazol-2-ylthio)]-pentyl-3-(2-methylethyl)-urea;
1-[5-(4,5-bis(4-dimethylaminophenyl)-1H-imidazol-2-ylthio)]pentyl-3(2,4-difluorophenyl)-1-[5-(4,5-diphenyl-1H-imidazol-2-ylthio)]pentyl-urea;
1-[5-(4,5-bis(4-dimethylaminophenyl)-1H-imidazol-2-ylthio)]pentyl-1-[5-(4,5-diphenyl-1H-imidazol-2-ylthio)]-pentyl-3-(2-methylethyl)-urea;
N-(5-1H-benzimidazol-2-ylthio)pentyl-N-[5-(4,5-diphenyl-1H-imidazol-2-ylthio)]pentyl-benzamide.

4. A pharmaceutical composition comprising an effective ACAT-inhibiting or antiatherosclerotic amount of a compound of claim 1 and a pharmaceutically acceptable carrier.

5. A pharmaceutical composition comprising an effective ACAT-inhibiting or antiatherosclerotic amount of a compound of claim 2 and a pharmaceutically acceptable carrier.

6. A pharmaceutical composition comprising an effective ACAT-inhibiting or antiatherosclerotic amount of a compound of claim 3 and a pharmaceutically acceptable carrier.

7. A method of treating hypercholesterolemia or atherosclerosis in a mammal comprising administering to the mammal a therapeutically effective amount of a compound of claim 1.

8. A method of treating hypercholesterolemia or atherosclerosis in a mammal comprising administering to the mammal a therapeutically effective amount of a compound of claim 2.

9. A method of treating hypercholesterolemia or atherosclerosis in a mammal comprising administering to the mammal a therapeutically effective amount of a compound of claim 3.